United States Patent
Lin et al.

(10) Patent No.: US 10,472,422 B2
(45) Date of Patent: Nov. 12, 2019

(54) TETRAVALENT ANTI-PSGL-1 ANTIBODIES AND USES THEREOF

(71) Applicants: BioAlliance C.V., Amsterdam (NL); AbGenomics International Inc., Dover, DE (US)

(72) Inventors: Rong-Hwa Lin, Palo Alto, CA (US); Shih-Yao Lin, Taipei (TW); Yu-Ying Tsai, Taipei (TW)

(73) Assignees: ABGENOMICS INTERNATIONAL INC., Dover, DE (US); BIOALLIANCE C.V., Amsterdam (NL)

( * ) Notice: Subject to any disclaimer, the term of this patent is extended or adjusted under 35 U.S.C. 154(b) by 2 days.

(21) Appl. No.: 15/400,888

(22) Filed: Jan. 6, 2017

(65) Prior Publication Data

US 2017/0198052 A1    Jul. 13, 2017

Related U.S. Application Data

(60) Provisional application No. 62/276,806, filed on Jan. 8, 2016.

(51) Int. Cl.
C07K 16/28 (2006.01)

(52) U.S. Cl.
CPC ...... *C07K 16/2896* (2013.01); *C07K 2317/21* (2013.01); *C07K 2317/24* (2013.01); *C07K 2317/35* (2013.01); *C07K 2317/53* (2013.01); *C07K 2317/56* (2013.01); *C07K 2317/565* (2013.01); *C07K 2317/622* (2013.01); *C07K 2317/626* (2013.01); *C07K 2317/732* (2013.01); *C07K 2317/76* (2013.01)

(58) Field of Classification Search
CPC ............ C07K 2317/24; C07K 2317/76; C07K 2317/565; C07K 2317/626; C07K 2317/732; C07K 16/2896; C07K 2317/622; C07K 2317/56; C07K 2317/53; C07K 2317/35; C07K 2317/21; C07K 2317/52; A61K 2039/505; A61K 35/17; A61K 39/395; A61P 29/00
See application file for complete search history.

(56) References Cited

U.S. PATENT DOCUMENTS

| | | | |
|---|---|---|---|
| 4,036,945 A | 7/1977 | Haber | |
| 4,331,647 A | 5/1982 | Goldenberg | |
| 4,676,980 A | 6/1987 | Segal et al. | |
| 4,683,195 A | 7/1987 | Mullis et al. | |
| 4,754,065 A | 6/1988 | Levenson et al. | |
| 4,800,159 A | 1/1989 | Mullis et al. | |
| 4,816,567 A | 3/1989 | Cabilly et al. | |
| 4,683,202 B1 | 11/1990 | Mullis | |
| 5,047,335 A | 9/1991 | Paulson et al. | |
| 5,198,560 A | 3/1993 | Kadow | |
| 5,278,299 A | 1/1994 | Wong et al. | |
| 5,314,995 A | 5/1994 | Fell et al. | |
| 5,500,362 A | 3/1996 | Robinson et al. | |
| 5,510,261 A | 4/1996 | Goochee et al. | |
| 5,530,101 A | 6/1996 | Queen et al. | |
| 5,545,806 A | 8/1996 | Lonberg et al. | |
| 5,545,807 A | 8/1996 | Surani et al. | |
| 5,565,332 A | 10/1996 | Hoogenboom et al. | |
| 5,569,825 A | 10/1996 | Lonberg et al. | |
| 5,580,717 A | 12/1996 | Dower et al. | |
| 5,585,089 A | 12/1996 | Queen et al. | |
| 5,591,828 A | 1/1997 | Bosslet et al. | |
| 5,625,126 A | 4/1997 | Lonberg et al. | |
| 5,633,425 A | 5/1997 | Lonberg et al. | |
| 5,661,016 A | 8/1997 | Lonberg et al. | |
| 5,677,427 A | 10/1997 | Goldenberg et al. | |
| 5,693,761 A | 12/1997 | Queen et al. | |
| 5,693,762 A | 12/1997 | Queen et al. | |
| 5,733,743 A | 3/1998 | Johnson et al. | |
| 5,750,373 A | 5/1998 | Garrard et al. | |
| 5,789,554 A | 8/1998 | Leung et al. | |
| 5,807,715 A | 9/1998 | Morrison et al. | |
| 5,821,337 A | 10/1998 | Carter et al. | |

(Continued)

FOREIGN PATENT DOCUMENTS

| | | |
|---|---|---|
| EP | 0 396 387 A2 | 11/1990 |
| EP | 0 404 097 A2 | 12/1990 |

(Continued)

OTHER PUBLICATIONS

Lu D, Zhu Z. Construction and production of an IgG-Like tetravalent bispecific antibody, IgG-single-chain Fv fusion. Methods Mol Biol. 2014;1060:185-213.*
Kontermann RE. Dual targeting strategies with bispecific antibodies. MAbs. Mar.-Apr. 2012;4(2):182-97. doi: 10.4161/mabs.4.2.19000. Epub Mar. 1, 2012.*
Sela-Culang I, Kunik V, Ofran Y. The structural basis of antibody-antigen recognition. Front Immunol. Oct. 8, 2013;4:302.*
Al-Lazikani, B. et al. (Nov. 7, 1997). "Standard Conformations for the Canonical Structures of Immunoglobulins," *Journal of Molecular Biology* 273(4):927-948.
Angal, S. et al. (Jan. 1993). "A Single Amino Acid Substitution Abolishes the Heterogeneity of Chimeric Mouse/Human (IgG4) Antibody," *Molecular Immunology* 30(1):105-108).

(Continued)

*Primary Examiner* — Rachel B Gill
(74) *Attorney, Agent, or Firm* — Morrison & Foerster LLP

(57) ABSTRACT

Provided herein are tetravalent antibodies that specifically bind to human PSGL-1. Unlike bivalent antibodies, these tetravalent antibodies contain a dimer of two monomers, with each monomer comprising two light chain variable (VL) domains and two heavy chain variable (VH) domains. This format allows for cross-linker/FcR-expressing cell-independent tetravalent antibodies against PSGL-1 that show enhanced efficacy as compared to bivalent PSGL-1 antibodies. These tetravalent antibodies can be used in a variety of diagnostic and therapeutic methods, including without limitation treating T-cell mediated inflammatory diseases, transplantations, and transfusions.

150 Claims, 5 Drawing Sheets

Specification includes a Sequence Listing.

(56) References Cited

U.S. PATENT DOCUMENTS

| | | |
|---|---|---|
| 5,866,692 A | 2/1999 | Shitara et al. |
| 5,965,726 A | 10/1999 | Pavlakis et al. |
| 5,985,908 A | 11/1999 | Boger |
| 5,997,867 A | 12/1999 | Waldmann et al. |
| 6,060,608 A | 5/2000 | Boger |
| 6,120,767 A | 9/2000 | Robinson et al. |
| 6,174,666 B1 | 1/2001 | Pavlakis et al. |
| 6,180,370 B1 | 1/2001 | Queen et al. |
| 6,214,345 B1 | 4/2001 | Firestone et al. |
| 6,262,271 B1 | 7/2001 | Boger |
| 6,265,150 B1 | 7/2001 | Terstappen et al. |
| 6,291,664 B1 | 7/2001 | Terstappen et al. |
| 6,281,354 B1 | 8/2001 | Boger |
| 6,329,508 B1 | 12/2001 | Friden |
| 6,331,415 B1 | 12/2001 | Cabilly et al. |
| 6,414,132 B1 | 7/2002 | Pavlakis et al. |
| 6,486,326 B2 | 11/2002 | Boger |
| 6,548,530 B1 | 4/2003 | Boger |
| 6,548,640 B1 | 4/2003 | Winter |
| 6,652,852 B1 | 11/2003 | Robinson et al. |
| 6,762,020 B1 | 7/2004 | Mack et al. |
| 6,794,498 B2 | 9/2004 | Pavlakis et al. |
| 6,808,901 B1 | 10/2004 | Neuberger et al. |
| 7,090,843 B1 | 8/2006 | Francisco et al. |
| 7,091,186 B2 | 8/2006 | Senter et al. |
| 7,223,837 B2 | 5/2007 | De Groot et al. |
| 7,256,257 B2 | 8/2007 | Doronina et al. |
| 7,332,164 B2 | 2/2008 | Greenwald et al. |
| 7,423,116 B2 | 9/2008 | Doronina et al. |
| 7,521,541 B2 | 4/2009 | Eigenbrot et al. |
| 7,553,816 B2 | 6/2009 | Senter et al. |
| 7,604,800 B2 | 10/2009 | Lin et al. |
| 7,659,241 B2 | 2/2010 | Senter et al. |
| 7,674,605 B2 | 3/2010 | Lin et al. |
| 7,705,045 B2 | 4/2010 | De Groot et al. |
| 7,744,888 B2 | 6/2010 | Lin et al. |
| 7,754,681 B2 | 7/2010 | Feng |
| 7,829,531 B2 | 11/2010 | Senter et al. |
| 7,855,275 B2 | 12/2010 | Eigenbrot et al. |
| 7,982,017 B2 | 7/2011 | Lin et al. |
| 8,153,581 B2 | 4/2012 | Kratz |
| 8,153,768 B2 | 4/2012 | Kunz et al. |
| 8,273,787 B2 | 9/2012 | Bell et al. |
| 8,287,871 B2 | 10/2012 | Lin et al. |
| 8,298,540 B2 | 10/2012 | Lin et al. |
| 8,309,093 B2 | 11/2012 | Gudas et al. |
| 8,361,472 B2 | 1/2013 | Lin et al. |
| 8,394,607 B2 | 3/2013 | Ebens, Jr. et al. |
| 8,455,622 B2 | 6/2013 | McDonagh et al. |
| 8,557,579 B2 | 10/2013 | Lin et al. |
| 8,568,718 B2 | 10/2013 | Lin et al. |
| 8,618,124 B2 | 12/2013 | Greenwald et al. |
| 8,628,775 B2 | 1/2014 | Lin et al. |
| 8,663,641 B2 | 3/2014 | Lin et al. |
| 8,828,397 B2 | 9/2014 | Lin et al. |
| 9,089,614 B2 | 7/2015 | Lin et al. |
| 9,216,228 B2 | 12/2015 | Kratz |
| 9,408,923 B2 | 8/2016 | Lin et al. |
| 9,494,574 B2 | 11/2016 | Lin et al. |
| 9,631,019 B2 | 4/2017 | Lin et al. |
| 9,950,077 B2 | 4/2018 | Lin et al. |
| 2003/0083263 A1 | 5/2003 | Doronina et al. |
| 2004/0116333 A1 | 6/2004 | Lin et al. |
| 2004/0202665 A1 | 10/2004 | Lazarovits et al. |
| 2005/0048549 A1 | 3/2005 | Cao et al. |
| 2005/0069955 A1 | 3/2005 | Plaksin et al. |
| 2005/0232929 A1 | 10/2005 | Kadkhodayan et al. |
| 2005/0238649 A1 | 10/2005 | Doronina et al. |
| 2006/0003940 A1 | 1/2006 | Lin et al. |
| 2006/0024317 A1 | 2/2006 | Boyd et al. |
| 2006/0193865 A1 | 8/2006 | Govindan et al. |
| 2007/0258987 A1 | 11/2007 | Francisco et al. |
| 2008/0050310 A1 | 2/2008 | Ebens, Jr. |
| 2008/0166363 A1 | 7/2008 | Govindan et al. |
| 2009/0068178 A1 | 3/2009 | Crowley et al. |
| 2009/0198044 A1 | 8/2009 | Lin et al. |
| 2009/0258420 A1 | 10/2009 | Van Vlijmen et al. |
| 2009/0274697 A1 | 11/2009 | Grasso et al. |
| 2009/0286721 A1* | 11/2009 | Pan .................. C12N 9/6456 514/9.3 |
| 2010/0124551 A1 | 5/2010 | Lin et al. |
| 2011/0033378 A1 | 2/2011 | Dimasi et al. |
| 2011/0137017 A1 | 6/2011 | Eigenbrot et al. |
| 2011/0256157 A1 | 10/2011 | Howard et al. |
| 2011/0301334 A1 | 12/2011 | Bhaka et al. |
| 2011/0305631 A1 | 12/2011 | Govindan et al. |
| 2012/0148580 A1 | 6/2012 | Chennasmsetty et al. |
| 2012/0213705 A1 | 8/2012 | Dimasi et al. |
| 2012/0282175 A1 | 11/2012 | Carrigan et al. |
| 2013/0011391 A1 | 1/2013 | Bassarab et al. |
| 2013/0066054 A1 | 3/2013 | Humphreys et al. |
| 2013/0177526 A1 | 7/2013 | Markland et al. |
| 2013/0177579 A1 | 7/2013 | Lin et al. |
| 2013/0251708 A1 | 9/2013 | Bassarab et al. |
| 2014/0065176 A1 | 3/2014 | Lin et al. |
| 2014/0105899 A1 | 4/2014 | Lin et al. |
| 2014/0170063 A1 | 6/2014 | Govindan et al. |
| 2014/0193437 A1 | 7/2014 | Lin et al. |
| 2014/0363454 A1 | 12/2014 | Jackson et al. |
| 2015/0183870 A1 | 7/2015 | Lin et al. |
| 2015/0352222 A1 | 12/2015 | Lin et al. |
| 2015/0366990 A1 | 12/2015 | Park et al. |
| 2016/0015827 A1 | 1/2016 | Lin et al. |
| 2016/0015830 A1 | 1/2016 | Lin et al. |
| 2016/0015831 A1 | 1/2016 | Lin et al. |
| 2016/0067351 A1 | 3/2016 | Geierstanger et al. |
| 2016/0051695 A1 | 5/2016 | Lin et al. |
| 2017/0190782 A1 | 7/2017 | Lin et al. |
| 2017/0198052 A1 | 7/2017 | Lin et al. |

FOREIGN PATENT DOCUMENTS

| | | |
|---|---|---|
| EP | 2050764 A1 | 4/2009 |
| EP | 2 357 006 A2 | 8/2011 |
| JP | 2012-519711 A | 8/2012 |
| RU | 94016384 A | 11/1996 |
| WO | WO-1987/04462 A1 | 7/1987 |
| WO | WO-1989/12624 A2 | 12/1989 |
| WO | WO-1991/00360 A1 | 1/1991 |
| WO | WO-1991/14438 A1 | 10/1991 |
| WO | WO-1992/08495 A1 | 5/1992 |
| WO | WO-1992/20373 A1 | 11/1992 |
| WO | WO-1993/06213 A1 | 4/1993 |
| WO | WO-1993/11161 A1 | 6/1993 |
| WO | WO-1999/58572 A1 | 11/1999 |
| WO | WO-2002/043661 A2 | 6/2002 |
| WO | WO-2002/088172 A2 | 11/2002 |
| WO | WO-2002/101069 A2 | 12/2002 |
| WO | WO-2003/000113 A2 | 1/2003 |
| WO | WO-2003/013603 A1 | 2/2003 |
| WO | WO-2003/088808 A2 | 10/2003 |
| WO | WO-2004/002528 A1 | 1/2004 |
| WO | WO-2004/043493 A1 | 5/2004 |
| WO | WO-2004/085386 A2 | 10/2004 |
| WO | WO-2004/085386 A3 | 10/2004 |
| WO | WO-2005/010153 A2 | 2/2005 |
| WO | WO-2005/081711 A2 | 9/2005 |
| WO | WO-2005/099768 A2 | 10/2005 |
| WO | WO-2005/099768 A3 | 10/2005 |
| WO | WO-2005/110475 A2 | 11/2005 |
| WO | WO-2005/110475 A3 | 11/2005 |
| WO | WO-2006/034488 A2 | 3/2006 |
| WO | WO-2006/034488 A3 | 3/2006 |
| WO | WO-2007/103288 A2 | 9/2007 |
| WO | WO-2007/140371 A2 | 12/2007 |
| WO | WO-2007/146172 A2 | 12/2007 |
| WO | WO-2007/146172 A3 | 12/2007 |
| WO | WO-2007/146172 A8 | 12/2007 |
| WO | WO-2008/038024 A1 | 4/2008 |
| WO | WO-2008/070593 A2 | 6/2008 |
| WO | WO-2008/070593 A3 | 6/2008 |
| WO | WO-2008/083312 A2 | 7/2008 |
| WO | WO-2008/083312 A3 | 7/2008 |
| WO | WO-2008/098788 A2 | 8/2008 |

(56) References Cited

FOREIGN PATENT DOCUMENTS

| | | |
|---|---|---|
| WO | WO-2009/079649 A1 | 6/2009 |
| WO | WO-2009/092011 A1 | 7/2009 |
| WO | WO-2009/099741 A1 | 8/2009 |
| WO | WO-2010/111018 A1 | 9/2010 |
| WO | WO-2010/111018 A8 | 9/2010 |
| WO | WO-2010/141902 A2 | 12/2010 |
| WO | WO-2010/141902 A3 | 12/2010 |
| WO | WO-2011/005481 A1 | 1/2011 |
| WO | WO-2011/106528 A1 | 9/2011 |
| WO | WO-2011/133039 A2 | 10/2011 |
| WO | WO-2011/156328 A1 | 12/2011 |
| WO | WO2012025530 A1 | 3/2012 |
| WO | WO-2012/112687 A1 | 8/2012 |
| WO | WO-2012/135675 A2 | 10/2012 |
| WO | WO-2012/135675 A3 | 10/2012 |
| WO | WO-2012/162482 A1 | 11/2012 |
| WO | WO-2012/174001 A1 | 12/2012 |
| WO | WO-2012/177837 A2 | 12/2012 |
| WO | WO-2013/093809 A1 | 6/2013 |
| WO | WO-2013/103800 A1 | 7/2013 |
| WO | WO-2013/173391 A1 | 11/2013 |
| WO | WO-2013/173392 A1 | 11/2013 |
| WO | WO-2013/173393 A1 | 11/2013 |
| WO | WO-2013/181597 A2 | 12/2013 |
| WO | WO-2013/181597 A3 | 12/2013 |
| WO | WO-2014/009774 A1 | 1/2014 |
| WO | WO-2014/011520 A1 | 1/2014 |
| WO | WO-2014/012479 A1 | 1/2014 |
| WO | WO-2014/057118 A1 | 4/2014 |
| WO | WO-2014/100762 A1 | 6/2014 |
| WO | WO-2014/107024 A1 | 7/2014 |
| WO | WO-2014/124316 A2 | 8/2014 |
| WO | WO-2014/145090 A1 | 9/2014 |
| WO | WO-2014/197871 A2 | 12/2014 |
| WO | WO-2015/012904 A2 | 1/2015 |
| WO | WO-2015/012904 A3 | 1/2015 |
| WO | WO2015013671 A1 | 1/2015 |
| WO | WO-2015/104385 A2 | 7/2015 |
| WO | WO-2015/195904 A1 | 12/2015 |
| WO | WO-2015/196089 A1 | 12/2015 |
| WO | WO-2015/196167 A1 | 12/2015 |
| WO | WO-2017/120534 A1 | 7/2017 |

OTHER PUBLICATIONS

Angiari, S. et al. (Dec. 1, 2013). "Regulatory T Cells Suppress the Late Phase of the Immune Response in Lymph Nodes through P-Selectin Glycoprotein Ligand-1," *J. Immunol.*, 191(11):5489-5500, 27 pages.

Bandgar, B.P. et al. (2003). "Highly Rapid and Direct Synthesis of Monoacylated Piperazine Derivatives from Carboxylic Acids Under Mild Conditions," *Tetrahedron Letters* 44:3855-3858.

Blencowe, C.A. et al. (2011). "Self-Immolative Linkers in Polymeric Delivery Systems," *Polym. Chem.* 2:773-790.

Bloom, J.W. et al. (1997). "Intrachain Disulfide Bond in the Core Hinge Region of Human IgG4," *Protein Sci.* 6:407-415.

Boerner, P. et al. (Jul. 1, 1991). "Production of Antigen-Specific Human Monoclonal Antibodies from In Vitro-primed Human Splenocytes," *Journal of Immunology* 147(1):86-95.

Boyd, P.N. et al. (Dec. 1995). "The Effect of the Removal of Sialic Acid, Galactose and Total Carbohydrate on the Functional Activity of Campath-1H," *Mol. Immunol.* 32(17/18):1311-1318.

Brodeur, B.R. et al. (1987). "Mouse-Human Myeloma Partners for the Production of Heterohybridomas," in *Monoclonal Antibody Production Techniques and Applications*, Marcel Dekker, Inc., New York, pp. 51-63.

Cabilly, S. et al. (Jun. 1984). "Generation of Antibody Activity from Immunoglobulin Polypeptide Chains Produced in *Escherichia coli*," *Proc. Nat'l. Acad. Sci. USA* 81(11):3273-3277.

Carpino, L.A. (1993). "1-Hydroxy-7-Azabenzotriazole. An Efficient Peptide Coupling Additive," *J. Am. Chem. Soc.* 115(10):4397-4398.

Carpino, L.A. et al. (1995). "Tetramethylfluoroformamidinium Hexafluorophosphate: A Rapid-Acting Peptide Coupling Reagent for Solution and Solid Phase Peptide Synthesis," *J. Am. Chem. Soc.* 117(19) :5401 -5402.

Carter, P. J. et. al. (May/Jun. 2008, e-pub. Jun. 15, 2004). "Antibody-Drug Conjugates for Cancer Therapy," *The Cancer Journal* 14(3):154-169.

Chen, S.-C. et al. (Nov. 15, 2004). "Cross-Linking of P-Selectin Glycoprotein Ligand-1 Induces Death of Activated T Cells," *Blood* 104(10):3233-3242.

Chothia, C. et al. (Aug. 1987). "Canonical Structures for the Hypervariable Regions of Immunoglobulins," *J. Mol. Biol.* 196(4):901-917.

Chu, G. et al. (1987). "Electroporation for the Efficient Transfection of Mammalian Cells with DNA," *Nucleic Acid Res.* 15(3):1311-1325.

Clackson, T. et al. (Aug. 15, 1991). "Making Antibody Fragments Using Phage Display Libraries," *Nature* 352:624-628.

Clynes, R. et al. (Jan. 1998). "Fc Receptors are Required in Passive and Active Immunity to Melanoma," *Proc. Natl. Acad. Sci. USA* 95:652-656.

Cole, S.P.C. et al. (1985). "The EBV-Hybridoma Technique and its Application to Human Lung Cancer," in *Monoclonal Antibodies and Cancer Therapy*, Reisfeld, R.A. et al. ed., Alan R. Liss. Inc., New York, NY, 77-96.

Coney, L.R. et al. (Nov. 15, 1991). "Cloning of a Tumor-Associated Antigen: MOv18 and MOv1 Antibodies Recognize a Folate-Binding Protein," *Cancer Res.* 51:6125-6132.

Constantin, G. (Nov. 2004). "PSGL-1 as a Novel Therapeutic Target," *Drug News Perspect.* 17(9):579-585.

Daintith, J. (2008). "A Dictionary of Chemistry," Oxford University Press, 6$^{th}$ ed., retrieved from <http://www.oxfordreference.com/view/10.1093/acref/9780199204632.001.0001/acref-9780199204632> lasted visited Aug. 17, 2017.

De Groot, F.M.H. et al. (2001, e-pub. Nov. 27, 2001). "Elongated Multiple Electronic Cascade and Cyclization Spacer Systems in Activatible Anticancer Prodrugs for Enhanced Drug Release," *J. Org. Chem.* 66(26):8815-8830.

Dijoseph, J.F. et al. (2007, e-pub. Jul. 26, 2007). "Therapeutic Potential of CD22-Specific Antibody-Targeted Chemotherapy Using Inotuzumab Ozogamicin (CMC-544) For the Treatment of Acute Lymphoblastic Leukemia," *Leukemia* 21:2240-2245.

Doronina, S.O. et al. (Jul. 2003, e-pub. Jun. 1, 2003). "Development of Potent Monoclonal Antibody Auristatin Conjugates for Cancer Therapy," *Nature Biotechnology* 21(7):778-784.

Ducry L. et al. (2010, e-pub. Sep. 21, 2009). "Antibody-Drug Conjugates: Linking Cytotoxic Payloads to Monoclonal Antibodies," *Bioconjugate Chem.* 21:5-13.

Ebel, W. et al. (Mar. 9, 2007). "Preclinical Evaluation of MORAb-003, A Humanized Monoclonal Antibody Antagonizing Folate Receptor-Alpha," *Cancer Immun.* 7:6, 8 pages.

Edelman, G.M. et al. (1969). "The Covalent Structure of an Entire γG Immunoglobulin Molecule," *Proc. Natl. Acad. Sci. USA* 63:78-85.

Farber, S. et al. (Jun. 3, 1948). "Temporary Remissions in Acute Leukemia in Children Produced by Folic Acid Antagonist, 4-Aminopteroyl-Glutamic Acid (Aminopterin)," *New England Journal of Medicine* 238(23):787-793.

Francisco, J.A. et al. (Aug. 15, 2003, e-pub. May 8, 2003). "cAC10-vcMMAE, an Anti-CD30-Monomethyl Auristatin E Conjugate with Potent and Selective Antitumor Activity," *Blood*, 102(4):1458-1465.

Gazzano-Santoro, H. et al. (Mar. 28, 1997). "A Non-Radioactive Complement-Dependent Cytotoxicity Assay for Anti-CD20 Monoclonal Antibody," *J. Immunol. Methods* 202(2):163-171.

GenBank Accession No. ABI74084, located at <http://www.ncbi.nlm.nih.gov/protein/ABI74084>,last visited on Oct. 21, 2014, 2 pages.

GenBank Accession No. CAA79298, located at <http:ncbi.nlm.nih.gov/protein/CAA79298>, last visited on Oct. 21, 2014, 2 pages.

Gianolio, D.A. et al. (2012, e-pub. Jul. 22, 2012). "Targeting HER2-Positive Cancer With Dolastatin 15 Derivatives Conjugated to Trastuzumab, Novel Antibody-Drug Conjugates," *Cancer Chemother. Pharmol.* 70:439-449.

(56) References Cited

OTHER PUBLICATIONS

Goding, J.W. *Monoclonal Antibodies: Principles and Practice*, Academic Press, (1986) pp. 59-1031.
Griffith, A.D. et al. (1993). "Human Anti-Self Antibodies with High Specificity from Phage Display Libraries," *EMBO J.* 12(2):725-734.
Haso, W. et al. (Feb. 14, 2013, e-pub. Dec. 14, 2012). "Anti-CD22-Chimeric Antigen Receptors Targeting B-Cell Precursor Acute Lymphoblastic Leukemia," *Blood* 121(7):1165-1174.
Hathcock, K. (May 2001). "T Cell Enrichment by Cytotoxic Elimination of B Cells and Accessory Cells," *Current Protocols in Immunology* 3:3.3.1-3.3.5.
Hollinger, P. et al. (Jul. 1993). "'Diabodies'": Small Bivalent and Bispecific Antibody Fragments, *Proc. Natl. Acad. Sci. USA* 90:6444-6448.
Holt, L.J. et al. (Nov. 2003). "Domain Antibodies: Proteins for Therapy," *Trends Biotechnology* 21(11):484-490.
Hoogenboom, H.R. et al. (Sep. 1991). "By-Passing Immunisation: Human Antibodies from Synthetic Repertoires of Germline $V_H$ Gene Segments Rearranged In Vitro," *Journal of Molecular Biology* 227(2):381-388.
Horgan, K. et al. (Apr. 2009). "Immunomagnetic Purification of T Cell Subpopulations," *Current Protocols in Immunology* 7:7.4.1-7.4.9, 6 pages.
Hsu, T.-A. et al. (Apr. 4, 1997). "Differential N-Glycan Patterns of Secreted and Intracellular IgG Produced in *Trichoplusia ni* Cells," *J. Biol. Chem.* 272(14):9062-9070.
Huang, C.-C. et al. (2005). "A Novel Apoptosis-Inducing Anti-PSGL-1 Antibody for T Cell-Mediated Diseases," *Eur. J. Immunol.* 35(7):2239-49.
Iliades, P. et al. (1997). "Triabodies: Single Chain Fv Fragments Without a Linker Form Trivalent Trimers," *FEBS Letters* 409:437-441.
IUPAC Gold Book, retrieved from <https://goldbook.iupac.org/html/A/A00123.html>, last visited Aug. 17, 2017.
Jain, N. et al. (2015, e-pub. Mar. 11, 2015). "Current ADS Linker Chemistry," *Pharm Res.* 32:3526-3540.
Jefferis, R. et al. (1997). "Glycosylation of Antibody Molecules: Structure and Functional Significance," *Chem. Immunol.* 65:111-128.
Jeffrey, S. C. et. al. (2005, e-pub. Feb. 5, 2005). "Design, Synthesis, and in Vitro Evaluation of Dipeptide-Based Antibody Minor Groove Binder Conjugates," *J. Med. Chem.* 48(5):1344-1358.
Jeffrey, S.C. et al. (Jul. 17, 2013, e-pub. Jun. 28, 2013). "A Potent Anti-CD70 Antibody-Drug Conjugate Combining a Dimeric Pyrrolobenzodiazepine Drug with Site-Specific Conjugation Technology," *Bioconjug. Chem.* 24(7):1256-1263.
Johnson, K.S. et al. (Aug. 1993). "Human Antibody Engineering," *Current Opinion in Structural Biology* 3(4):564-571.
Junutula, J.R. et al. (Aug. 2008, e-published Jul. 20, 2008). "Site-Specific Conjugation of a Cytotoxic Drug to an Antibody Improves the Therapeutic Index," *Nat. Biotech.* 26(8):925-932.
Kalli, K.R. et al. (2007). "MORAb-003, A Fully Humanized Monoclonal Antibody Against the Folate Receptor α, For the Potential Treatment of Epithelial Ovarian Cancer," *Curr. Opin. Investig.* 8(12):1067-1073.
Kanof, M. E. (May 2001). "Purification of T Cell Subpopulations," *Current Protocols in Immunology* Chapter 7, Unit 7.3, 5 pages.
Kantarjian, H. et al. (Apr. 2012, e-pub. Feb. 21, 2012). "Inotuzumab Ozogamicin, An Anti-CD22-Calecheamicin Conjugate, For Refractory and Relapsed Acute Lyphocytic Leukaemia: A Phase 2 Study," *Lancet Oncol.* 13:403-411.
Kato, J. et al. (Dec. 2012). "Efficacy and Toxicity of a CD22-Targeted Antibody-Saporin Conjugage in a Xenograft Model of Non-Hodgkin's Lymphoma," *Oncoimmunology* 1(9):1469-1475.
Kitson, S. et al. (2013). "Antibody-drug conjugates (ADCs)—Biotherapeutic bullets," *Monographic Supplement Series CROs/CMOs—Chimica Oggi—Chemistry Today* pp. 30-36.
Koblinski, J.E. et al. (Feb. 15, 2000). "Unraveling the Role of Proteases in Cancer," *Clin. Chem. Acta* 291(2):113-135.

Kohler, G. et al. (Aug. 7, 1975). "Continuous Cultures of Fused Cells Secreting Antibody of Predefined Specificity," *Nature* 256(5517):495-497.
Kortt, A.A. et al. (Apr. 1997). "Single-Chain Fv Fragments of Anti-Neuraminidase Antibody NC10 Containing Five- and Ten-Residue Linkers Form Dimers and with Zero-Residue Linker a Trimer," *Protein Engineering* 10(4):423-433.
Kozbor, D. (Dec. 1984). "A Human Hybrid Myeloma for Production of Human Monoclonal Antibodies," *J. Immunol.* 133(6):3001-3005.
Krauss, J. et al. (2003). "Specificity Grafting of Human Antibody Frameworks Selected From a Phage Display Library: Generation of a Highly Stable Humanized Anti-CD22 Single-Chain Fv Fragment," *Protein Engineering* 16(10):753-759.
Kreitman, R.J. et al. (Oct. 15, 2011). "Antibody-Fusion Proteins Anti-CD22 Recombinant Immunotoxin Moxetumomab Pasudotox," *Clin. Cancer Res.* 17(20):6398-6405, 11 pages.
Labrijn, A.F. et al. (Aug. 2009, e-pub. Jul. 20, 2009). "Therapeutic IgG4 Antibodies Engage in Fab-Arm Exchange with Endogenous Human IgG4 In Vivo," *Nat Biotechnol.* 27(8):767-771.
Leamon, C.P. et al. (Jul. 1991). "Delivery of Macromolecules Into Living Cells: A Method That Exploits Folate Receptor Endocytosis," *Proc. Natl. Acad. Sci. USA* 88:5572-5576.
Leonard, J.P. et al. (Aug. 1, 2005). "Combination Antibody Therapy With Epratuzumab and Rituximab in Relapsed or Refractory Non-Hodgkin's Lymphoma," *J. Clin. Oncol.* 23(22):5004-5051.
Li, P. et al. (Aug. 2001). "The Development of Highly Efficient Onium-Type Peptide Coupling Reagents Based Upon Rational Molecular Design," *J. Pept. Res.* 58(2):129-139.
Li, D. et al. (2013). "DCDT2980S, an Anti-CD22-Monomethyl Auristatin E Antibody-Drug Conjugate, is a Potential Treatment for Non-Hodgkin Lymphoma," *Molecular Cancer Therapeutics* 12(7):1255-1265.
Linden, O. et al. (Jul. 15, 2005). "Dose-Fractionated Radioimmunotherapy in Non-Hodgkin's Lymphoma Using DOTA-Conjugated, $^{90}$Y-Radiolabeled, Humanized Anti-CD22 Monoclonal Antibody, Epratuzumab," *Clin. Cancer Res.* 11(14):5215-5122.
Loudon, G.M. (2002). *Organic Chemistry*, Fourth Edition, Oxford University Press, New York, pp. 360-361.
Lyons, A. et al. (Aug. 1990). "Site-Specific Attachment to Recombinant Antibodies via Introduced Surface Cysteine Residues," *Protein Engineering* 3(8):703-708.
Marks, J. D. et al. (Dec. 5, 1991). "By-Passing Immunization: Human Antibodies From V-Gene Libraries Displayed on Phage," *Journal of Molecular Biology* 222(3):581-597.
Marks, J. D. et al. (Jul. 1992). "By-Passing Immunization: Building High Affinity Human Antibodies by Chain Shuffling," *Bio/Technol.* 10:779-783.
McCafferty, J. et al. (Dec. 6, 1990). "Phage Antibodies: Filamentous Phage Displaying Antibody Variable Domains," *Nature* 348(6301):552-554.
McEver, R.P. et al. (Aug. 1997). "Perspectives Series: Cell Adhesion in Vascular Biology: Role of PSGL-1 Binding to Selectins in Leukocyte Recruitment," *J. Clin. Invest.* 100(3):485-492.
Milstein. C. et al. (Oct. 6, 1983). "Hybrid Hybridomas and Their Use in Immunohistochemistry," *Nature* 305:537-539.
Mullis, K.B. et al. (1994). *PCR: The Polymerase Chain Reaction*, Mullis et al. eds., Birkauswer Press, Boston.
Munson, P.J. et al. (1980). "LIGAND: A Versatile Computerized Approach for Characterization of Ligand-binding Systems," *Anal. Biochem.* 107:220-239.
Muppidi, J. et al. (2004). "Related Isolation Procedures and Functional Assays:Measurement of Apoptosis and Other Forms of Cell Death," *Current Protocols in Immunology Supplement* 59:3.17.1-3.17.36, 36 pages.
Muyldermans, S. (Jun. 2001). "Single Domain Camel Antibodies: Current Status," *Reviews in Molecular Biotechnology* 74(4):277-302.
Nisonoff, A. et al. (Aug. 1960). "Separation of Univalent Fragments from the Bivalent Rabbit Antibody Molecule by Reduction of Disulfide Bonds," *Arch Biochem. Biophys.* 89(2):230-244.

(56) References Cited

OTHER PUBLICATIONS

Oi, V.T. et al. (Feb. 1983). "Immunoglobulin Gene Expression in Transformed Lymphoid Cells," *Proc. Natl. Acad. Sci. USA* 80:825-829.

Perez-Frias, A, et al. (Nov. 2014). "Development of an Autoimmune Syndrome Affecting the Skin and Internal Organs in P-Selectin Glycoprotein Ligand 1 Leukocyte Receptor-Deficient Mice," *Arthritis Rheumatol.* 66(11):3178-3189.

Pluckthun, A. (1994). "Antibodies From *Escherichia coli*," in *The Pharmacology of Monoclonal Antibodies*, vol. 113, Rosenburg and Moore eds., Springer-Verlag, New York, pp. 269-315.

Porter, R.R. (1959). "The Hydrolysis of Rabbit γ-Globulin and Antibodies with Crystalline Papain," *Biochem. J.* 73: 119-127.

Polson, A. G. et al. (Mar. 15, 2009). "Antibody-Drug Conjugates for the Treatment of Non-Hodgkin's Lymphoma: Target and linker-Drug Selection", *Cancer Research* 269(6):2358-2364.

Presta, L.G. et al. (2002). "Engineering Therapeutic Antibodies for Improved Function," *Biochem. Soc. Trans.* 30(4):487-490.

Rice, D. et al. (Dec. 1982). "Regulated Expression of an Immunoglobulin κ Gene Introduced Into a Mouse Lymphoid Cell Line," *Proc. Natl. Acad. Sci. USA* 79:7862-7865.

Rousseaux. J. et al. (1986). "Optimal Conditions for the Preparation of Proteolytic Fragments from Monoclonal IgG of Different Rat IgG Subclasses," *Methods Enzymol.* 121:663-669.

Sambrook, J. et al. (1989). *Molecular Cloning: A Laboratory Manual*, 3$^{rd}$ Ed. 29 pages.

Sheets, M.D. et al. (May 26, 1998). "Efficient Construction of a Large Nonimmune Phage Antibody Library: The Production of High-Affinity Human Single-Chain Antibodies to Protein Antigens," *Proc. Natl. Acad. Sci. USA* 95(11):6157-6162.

Shields, R.L. et al. (Mar. 2, 2001). "High Resolution Mapping of the Binding Site on Human IgG1 for FcγRI, FcγRII, FcγRIII, and FcRn and Design of IgG1 Variants with Improved Binding to the FcγR," *J. Biol. Chem.* 276(9):6591-6604.

Smyth, D.G. (1967). "Use of Papain, Pepsin, and Subtilisin in Sequence Determination," *Methods in Enzymology* 11:421-426.

Spearman, M.E. et al. (Feb. 3, 1987). "Disposition of the Monoclonal Antibody-Vinca Alkaloid Conjugate KS1/4-DAVLB (LY256787) and Free 4-Desacetylvinblastine in Tumor-Bearing Nude Mice," *The Journal of Pharmacology and Experimental Therapeutics*, 241(2):695-703.

Spertini, O. et al. (1996). "P-Selectin Glycoprotein Ligand 1 is a Ligand for L-Selectin on Neutrophils, Monocytes, and CD34 + Hematopoietic Progenitor Cells," *J. Cell Biol.* 135(2):523-531.

Stimmel, J.B. et al. (Sep. 29, 2000, e-published Jul. 3, 2000). "Site-Specific Conjugation on Serine → Cysteine Variant Monoclonal Antibodies," *J. Biol. Chem.* 275(39):30445-30450.

Stubenrauch, K. et al. (2010). "Impact of Molecular Processing in the Hinge Region of Therapeutic IgG4 Antibodies on Disposition Profiles in Cynomolgus Monkeys," *Drug Metab. Dispos.* 38(1):84-91.

Sullivan-Chang, L. et al. (2013, e-pub. May 22, 2013). "Targeting CD22 in B-Cell Malignancies: Current Status and Clinical Outlook," *BioDrugs* 27(4):293-304.

Sun, M.M.C. et al. (Sep./Oct. 2005). "Reduction-Alkylation Strategies for the Modification of Specific Monoclonal Antibody Disulfides," *Bioconjug. Chem.* 16(5):1282-1290, 22 pages.

Suresh, M.R. et al. (1986). "Bispecific Monoclonal Antibodies from Hybrid Hybridomas," *Methods in Enzymology* 121:210-228.

Teicher, B.A. et al. (Dec. 2009). "Antibody-Drug Conjugate Targets," *Current Cancer Drug Targets* 9(8): 982-1004.

Thornton, A.M. (2003, e-pub. Nov. 1, 2003). "Fractionation of T and B Cells Using Magnetic Beads," *Current Protocols in Immunology* 55:3.5A. I-3.5A, 11 pages.

Toneguzzo, F. et al. (Feb. 1986). "Electric Field-Mediated DNA Transfer: Transient and Stable Gene Expression in Human and Mouse Lymphoid Cells," *Mol. Cell. Biol.* 6(2):703-706.

Trail, P. A. et al. (Jul. 9, 1993). "Cure of Xenografted Human Carcinomas by BR96-Doxorubicin Immunoconjugates," *Science* 261(5118):212-215.

Trail, P. A. et al. (Jan. 1, 1997). "Effect of Linker Variation on the Stability, Potency, and Efficacy of Carcinoma-Reactive BR64-Doxorubicin Immunoconjugates," *Cancer Research* 57(1):100-105.

Umana, P. et al. (Feb. 1999). "Engineered Glycoforms of an Antineuroblastoma IgG1 with Optimized Antibody-Dependent Cellular Cytotoxic Activity," *Nature Biotech.* 17:176-180.

Urzainqui, A. et al. (2013). "AB0227 PSGL-1 Deficiency Develops Systemic Sclerosis in Mice," *Ann. Rheum. Dis.* 71:650.

Van Der Neut Kolfschoten, M. et al. (Sep. 14, 2007). "Anti-Inflammatory Activity of Human IgG4 Antibodies by Dynamic Fab Arm Exchange," *Science* 317:1554-1557, retrieved from <http://science.sciencemag.org/> last visited Jul. 21, 2017.

Vaughan, T.J. et al. (Mar. 1996). "Human Antibodies with Sub-Nanomolar Affinities Isolated from a Large Non-Immunized Phage Display Library," *Nature Biotechnology* 14(3):309-314.

Veerman, K.M. et al. (2012, e-pub. Jan. 16, 2012). "PSGL-1 Regulates the Migration and Proliferation of CD8+ T Cells under Homeostatic Conditions," *J. Immunol.* 188:1638-1646.

Vlahov, I.R. et al. (Jun. 6, 2012). "Engineering Folate-Drug Conjugates to Target Cancer: From Chemistry to Clinic". *Bioconjugate Chemistry* 23:1357-1369.

Waterhouse, P. et al. (1993). "Combinatorial Infection and In Vivo Recombination: A Strategy for Making Large Phage Antibody Repertories," *Nucl. Acids Res.* 21(9):2265-2266.

Winter, G. et al. (1994). "Making Antibodies by Phage Display Technology," *Annu. Rev. Immunol.* 12:433-455.

Wittwer, A.J. et al. (May 1, 1990). "Glycosylation at Asn-184 Inhibits the Conversion of Single-Chain to Two-Chain Tissue-Type Plasminogen Activator by Plasmin," *Biochemostry* 29(17):4175-4180.

Wright, A. et al. (Jan. 1997). "Effect of Glycosylation on Antibody Function: Implications for Genetic Engineering," *TIBTECH* 15:26-32.

Wyss, D.F. et al. (1996). "The Structural Role of Sugars in Glycoproteins," *Current Opin. Biotech.* 7:409-416.

Xia, W. et al. (2010, e-pub. Jul. 28, 2010). "Folate-Targeted Therapies for Cancer," *J. Med. Chem.* 53(19):6811-6824.

Yu, S.-F. et al. (Jul. 15, 2015, e-pub. Apr. 3, 2015). "A Novel Anti-CD22 Anthracycline-Based Antibody-Drug Conjugate (ADC) that Overcomes Resistance to Auristatin-Based ADC's," *Clinical Cancer Research* 21(14):3298-3306.

Zacchetti, A. et al. (2009). "Lu-Labeled MOv18 As Compared to $^{131}$I- or $^{90}$Y-Labeled Mov18 Has the Better Therapeutic Effect in Eradication of Alpha Folate Receptor-Expression Tumor Xenografts," *Nucl. Med. Biol.* 36:759-770.

Chinese Second Office Action for Application No. 201380073519.6, dated Jun. 29, 2017.

Extended European Search Report dated Jul. 27, 2016, for European Patent Application No. 13865282.1, filed on Dec. 20, 2013, 7 pages.

Final Office Action for U.S. Appl. No. 14/745,336, dated Jul. 24, 2017, filed Jun. 19, 2015.

International Search Report, dated Apr. 4, 2014, for PCT Application No. PCT/US2013/077306, filed Dec. 20, 2013, 7 pages.

International Search Report dated Sep. 15, 2015, for PCT Application No. PCT/US2015/036414, filed Jun. 18, 2015, 8 pages.

International Search Report, dated Oct. 13, 2015, for PCT Application No. PCT/US2015/036721, filed Jun. 19, 2015, 11 pages.

International Search Report, dated Oct. 14, 2015, for PCT Application No. PCT/US2015/036824, filed Jun. 19, 2015, 5 pages.

International Search Report, dated Mar. 10, 2017, for PCT Application No. PCT/US2017/012621, filed Jan. 6, 2017. 9 pages.

New Zealand Examination Report and Notice of Allowance dated May 22, 2017.

Office Action for Columbian Patent Application No. 15168183, filed on Dec. 20, 2013.

Taiwan Patent Application No. 1060100473 published Aug. 1, 2017, filed on Jan. 6, 2017.

Written Opinion dated Apr. 4, 2014, for PCT Application No. PCT/US2013/077306, filed Dec. 20, 2013, 10 pages.

Written Opinion dated Sep. 15, 2015, for PCT Application No. PCT/US2015/036414, filed Jun. 18, 2015, 9 pages.

Written Opinion dated Oct. 13, 2015, for PCT Application No. PCT/US2015/036721, filed Jun. 19, 2015, 9 pages. (9.40).

(56) References Cited

OTHER PUBLICATIONS

Written Opinion dated Oct. 14, 2015, for PCT Application No. PCT/US2015/036824, filed on Jun. 20, 2014, 8 pages. (10.40).
Written Opinion dated Mar. 10, 2017, for PCT Application No. PCT/US2017/012621, filed on Jan. 6, 2017, 4 pages.
Ab, O. et al. (2015, e-pub. Apr. 22, 2015). "IMGN853, a Folate Receptor-α (FRα)-Targeting Antibody-Drug Conjugate, Exhibits Potent Targeted Antitumor Activity against FRα—Expressing Tumors," *Molecular Cancer Therapeutics* 14(7):1605-1613.
Bowie, J.U. et al. (Mar. 1990). "Deciphering the Message in Protein Sequences: Tolerance to Amino Acid Substitutions," *Science* 247(4948):1306-1310.
Li, H. et al. (May 19, 2010, e-pub. Apr. 29, 2010). "Folate-Immunoglobulin G as an Anticancer Therapeutic Antibody," *Bioconjugate Chemistry* 21(5):961-968.
Lu, J.Y. et al. (Jan. 1, 1999). "Folate-Targeted Enzyme Prodrug Cancer Therapy Utilizing Penicillin-V Amidase and a Doxorubicin Prodrug," *Journal of Drug Targeting*, 7(1):43-53.
Nagayoshi, R. et al. (Sep. 1, 2005): "Effectiveness of Anti-Folate Receptor β Antibody Conjugated With Truncated *Pseudomonas* Exotoxin in the Targeting of Rheumatoid Arthritis Synovial Macrophages," *Arthritis & Rheumatism* 52(9):2666-2675.
Shi, H. et al. (Aug. 31, 2015). "A Current Review of Folate Receptor Alpha As a Potential Tumor Target in Non-Small-Cell Lung Cancer," *Drug Design, Development and Therapy* 9:4989-4996.
Extended European Search Report dated Jan. 2, 2018, for European Patent.Application No. 15810153.5, filed on Dec. 21, 2016, 12 pages.
European Communication Pursuant to Rules 70(2) and 70a(2) EPC dated Jan. 19, 2018 for European Patent Application No. 15810153.5, filed Dec. 21, 2016, 1 page.
International Preliminary Report on Patentability, dated Jul. 10, 2018, for PCT Application No. PCT/US2017/012621, filed Jan. 6, 2017, 5 pages.
Extended European Search Report dated Jul. 16, 2019, for European Patent Application No. 17736478.3, filed on Jul. 30, 2018, 11 pages.

\* cited by examiner

TETRAVALENT ANTI-PSGL-1 ANTIBODIES AND USES THEREOF

CROSS REFERENCE TO RELATED APPLICATIONS

This application claims the priority benefit of U.S. Provisional Application Ser. No. 62/276,806, filed Jan. 8, 2016, which is incorporated herein by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 606592001300SEQLIST.TXT, date recorded: Jan. 3, 2017, size: 70 KB).

FIELD

Provided herein are tetravalent antibodies that specifically bind to human P-selectin glycoprotein ligand-1 (PSGL-1), as well as polynucleotides, vectors, host cells, methods, pharmaceutical compositions, kits, and uses related thereto. These tetravalent antibodies may find use in a variety of diagnostic and therapeutic methods, including without limitation treating T-cell mediated inflammatory diseases, transplantations, and transfusions.

BACKGROUND

Inflammatory responses to infection or injury are initiated by the adherence of leukocytes to the vascular wall (McEver et al, 1997, J. Clin. Invest., 100 (3): 485-492). Selectin represents a family of glycoproteins which mediate the first leukocyte-endothelial cell and leukocyte-platelet interactions during inflammation. The selectin family, which consists of L-selectin, E-selectin, and P-selectin, comprises an $NH_2$-terminal lectin domain, followed by an EGF-like domain, a series of consensus repeats, a transmembrane domain, and a short cytoplasmic tail. The lectin domains of selectins interact with specific glycoconjugate ligands in order to facilitate cell adhesion. L-selectin, expressed on most leukocytes, binds to ligands on some endothelial cells and other leukocytes. E-selectin, expressed on cytokine activated endothelial cells, binds to ligands on most leukocytes. P-selectin, expressed on activated platelets and endothelial cells, also binds to ligands on most leukocytes.

P-selectin glycoprotein ligand-1 ("PSGL-1"), also known as SELPLG or CD162 (cluster of differentiation 162) is a human mucin-type glycoprotein ligand for all three selectins (Constantin, Gabriela, 2004, Drug News Perspect., 17(9): 579-585; McEver et al., 1997, J. Clin. Invest., 100 (3): 485-492). PSGL-1 is a disulfide-bonded homodimer with two 120-kD subunits and is expressed on the surface of monocytes, lymphocytes, granulocytes, and in some $CD34^+$ stem cells. PSGL-1 is likely to contribute to pathological leukocyte recruitment in many inflammatory disorders since it facilitates the adhesive interactions of selectins. In addition, PSGL-1 is shown to have a unique regulatory role in T cells. Mice deficient in PSGL-1 show enhanced proliferative responses and autoimmunity, suggesting that PSGL-1 plays an important role in down-regulating T cell responses (Krystle M. et al. J. Immunol. 2012; 188:1638-1646. Urzainqui et al. Ann Rheum Dis 2013; 71:650; Pérez-Frías A, et al. Arthritis Rheumatol. 2014 November; 66(11):3178-89.; Angiari et al. J Immunol. 2013; 191(11):5489-500).

Several anti-PSGL-1 antibodies have been developed (see, e.g., International Application Pub. Nos. WO 2005/110475, WO 2003/013603, and WO 2012/174001; Constantin, Gabriela, 2004, Drug News Perspect., 17(9): 579-585, Chen et al. Blood. 2004; 104(10):3233-42, Huang et al, Eur J Immunol. 2005; 35(7):2239-49; and U.S. Pat. No. 7,604,800). Some of the existing agonistic PSGL-1 antibodies preferentially induce apoptosis of late-stage activated T cells but not other PSGL-1-expressing cells; such antibodies may therefore be useful as anti-inflammatory therapeutics, or for use in transplantations and/or transfusions. However, a need exists for improved anti-PSGL-1 antibodies with greater in vivo efficacy than existing antibodies.

All publications, patents, and patent applications cited herein are hereby incorporated by reference in their entirety for all purposes.

BRIEF SUMMARY

To meet this need, provided herein are tetravalent antibodies that specifically bind to human PSGL-1, as well as polynucleotides, vectors, host cells, methods, pharmaceutical compositions, kits, and uses related thereto. The present disclosure demonstrates that tetravalent antibodies that specifically bind to human PSGL-1 have greater potency and efficacy than conventional (e.g., bivalent) anti-PSGL-1 antibodies. As such, these tetravalent antibodies may find use, inter alia, in diagnostic and/or therapeutic methods, uses, and compositions related to T-cell function, such as in treating T-cell mediated inflammatory diseases, transfusions, and/or transplantations.

Accordingly, in one aspect, provided herein is a tetravalent antibody that specifically binds to human PSGL-1, the tetravalent antibody comprising a dimer of two monomers, wherein each monomer of the dimer comprises a single-chain polypeptide comprising: (a) two light chain variable (VL) domains, wherein each of the two VL domains comprises a CDR-L1, a CDR-L2, and a CDR-L3; (b) two heavy chain variable (VH) domains, wherein each of the two VH domains comprises a CDR-H1, a CDR-H2, and a CDR-H3; and (c) an antibody Fc domain, wherein each of the two VL domains forms a VH-VL binding unit with a corresponding VH domain of the two VH domains, and wherein each of the two VH-VL binding units is specific for human PSGL-1. In some embodiments, at least one of the two VH domains comprises: (i) a CDR-H1 comprising the amino acid sequence of SEQ ID NO:17; (ii) a CDR-H2 comprising the amino acid sequence of SEQ ID NO:18; and (iii) a CDR-H3 comprising the amino acid sequence of SEQ ID NO:19. In some embodiments, each of the two VH domains comprises: (i) a CDR-H1 comprising the amino acid sequence of SEQ ID NO:17; (ii) a CDR-H2 comprising the amino acid sequence of SEQ ID NO:18; and (iii) a CDR-H3 comprising the amino acid sequence of SEQ ID NO:19. In some embodiments, one or both of the two VH domains comprises the amino acid sequence of SEQ ID NO:23, or an amino acid sequence having at least 90%, at least 95%, or at least 99% sequence identity to SEQ ID NO:23. In some embodiments, one or both of the two VH domains comprises the amino acid sequence of SEQ ID NO:29, or an amino acid sequence having at least 90%, at least 95%, or at least 99% sequence identity to SEQ ID NO:29. In some embodiments, at least one of the two VL domains comprises: (i) a CDR-L1 comprising the amino acid sequence of SEQ ID NO:20; (ii) a CDR-L2 comprising the amino acid sequence of SEQ ID NO:21; and (iii) a CDR-L3 comprising the amino acid sequence of SEQ ID NO:22. In some embodiments, each of the two VL domains comprises: (i) a CDR-L1 comprising the amino acid sequence of SEQ ID NO:20; (ii) a CDR-L2 comprising the amino acid sequence of SEQ ID NO:21; and (iii) a CDR-L3 comprising the amino acid sequence of SEQ ID NO:22. In some embodiments, one or both of the two VL domains comprises the amino acid sequence of SEQ ID NO:24, or an amino acid sequence having at least 90%, at least 95%, or at least 99% sequence identity to SEQ ID NO:24. In some embodiments, one or both of the two VL domains comprises the amino acid sequence of SEQ ID NO:30, or an amino acid sequence having at least 90%, at least 95%, or at least 99% sequence identity to SEQ ID NO:30. In some embodiments, each of the two single-chain polypeptides comprises, from N-terminus to C-terminus: (a) a first VL domain of the two VL domains; (b) a first linker sequence; (c) a first VH domain of the two VH domains; (d) a second linker sequence; (e) a second VL domain of the two VL domains; (f) a third linker sequence; (g) a second VH domain of the two VH domains; (h) a fourth linker sequence; and (i) the antibody Fc domain. In some embodiments, the first, second and third linker sequences each comprise two or more repeats of the amino acid sequence of SEQ ID NO:25. In some embodiments, the first and the third linker sequences have the same sequence and comprise two repeats of SEQ ID NO:25. In some embodiments, the second linker sequence comprises five repeats of SEQ ID NO:25. In some embodiments, the fourth linker sequence comprises the amino acid sequence of SEQ ID NO:26. In some embodiments, each of the two single-chain polypeptides comprises the amino acid sequence of SEQ ID NO:1, or an amino acid sequence having at least 90%, at least 95%, or at least 99% sequence identity to SEQ ID NO:1. In some embodiments, each of the two single-chain polypeptides is encoded by a polynucleotide comprising the polynucleotide sequence of SEQ ID NO:2. In some embodiments, each of the two single-chain polypeptides comprises, from N-terminus to C-terminus: (a) a first VH domain of the two VH domains; (b) a first linker sequence; (c) a first VL domain of the two VL domains; (d) a second linker sequence; (e) a second VL domain of the two VL domains; (f) a third linker sequence; (g) a second VH domain of the two VH domains; (h) a fourth linker sequence; and (i) the antibody Fc domain. In some embodiments, each of the two single-chain polypeptides comprises, from N-terminus to C-terminus: (a) a first VL domain of the two VL domains; (b) a first linker sequence; (c) a first VH domain of the two VH domains; (d) a second linker sequence; (e) a second VH domain of the two VH domains; (f) a third linker sequence; (g) a second VL domain of the two VL domains; (h) a fourth linker sequence; and (i) the antibody Fc domain. In some embodiments, the first, second or third linker sequence comprises two or more repeats of the amino acid sequence of SEQ IN NO:25. In some embodiments, the first, second or third linker sequence comprises the amino acid sequence of SEQ ID NO:33, 34, 35, or 36. In some embodiments, the first and the third linker sequences have the same sequence comprising five repeats of SEQ ID NO:25. In some embodiments, the second linker sequence comprises the amino acid sequence of SEQ ID NO:27. In some embodiments, the fourth linker sequence comprises the amino acid sequence of SEQ ID NO:26. In some embodiments, each of the two single-chain polypeptides comprises the amino acid sequence of SEQ ID NO:3, or an amino acid sequence having at least 90%, at least 95%, or at least 99% sequence identity to SEQ ID NO:3. In some embodiments, each of the two single-chain polypeptides is encoded by a polynucleotide comprising the polynucleotide sequence of SEQ ID NO:4. In some embodiments, each of the two single-chain polypeptides comprises the amino acid sequence of SEQ ID NO:5. In some embodiments, each of the two single-chain polypeptides is encoded by a polynucleotide comprising the polynucleotide sequence of SEQ ID NO:6.

In another aspect, provided herein is a tetravalent antibody that specifically binds to human PSGL-1, the tetravalent antibody comprising a dimer of two monomers, wherein each monomer of the dimer comprises an antibody heavy chain and an antibody light chain; wherein the antibody light chain comprises: (i) two light chain variable (VL) domains, wherein each of the two VL domains comprises a CDR-L1, a CDR-L2, and a CDR-L3, (ii) a first heavy chain variable (VH) domain, and (iii) a light chain constant (CL) domain; wherein the antibody heavy chain comprises: (i) a second heavy chain variable (VH) domain, and (ii) a heavy chain constant region comprising a first heavy chain constant region (CH1) domain, an antibody hinge region, an second heavy chain constant region (CH2) domain, and a third heavy chain constant region (CH3) domain; wherein the first and the second VH domains each comprise a CDR-H1, a CDR-H2, and a CDR-H3, wherein each of the two VL domains forms a VH-VL binding unit with a corresponding VH domain of the first and the second VH domains, and wherein each of the two VH-VL binding units is specific for human PSGL-1. In some embodiments, at least one of the first and the second VH domains comprises: (i) a CDR-H1 comprising the amino acid sequence of SEQ ID NO:17; (ii) a CDR-H2 comprising the amino acid sequence of SEQ ID NO:18; and (iii) a CDR-H3 comprising the amino acid sequence of SEQ ID NO:19. In some embodiments, the first and the second VH domains each comprise: (i) a CDR-H1 comprising the amino acid sequence of SEQ ID NO:17; (ii) a CDR-H2 comprising the amino acid sequence of SEQ ID NO:18; and (iii) a CDR-H3 comprising the amino acid sequence of SEQ ID NO:19. In some embodiments, the first and/or the second VH domains comprise the amino acid sequence of SEQ ID NO:23, or an amino acid sequence having at least 90%, at least 95%, or at least 99% sequence identity to SEQ ID NO:23. In some embodiments, the first and/or the second VH domains comprise the amino acid sequence of SEQ ID NO:29, or an amino acid sequence having at least 90%, at least 95%, or at least 99% sequence identity to SEQ ID NO:29. In some embodiments, at least one of the first and the second VL domains comprises: (i) a CDR-L1 comprising the amino acid sequence of SEQ ID NO:20; (ii) a CDR-L2 comprising the amino acid sequence of SEQ ID NO:21; and (iii) a CDR-L3 comprising the amino acid sequence of SEQ ID NO:22. In some embodiments, the first and the second VL domains each comprise: (i) a CDR-L1 comprising the amino acid sequence of SEQ ID NO:20; (ii) a CDR-L2 comprising the amino acid sequence of SEQ ID NO:21; and (iii) a CDR-L3 comprising the amino acid sequence of SEQ ID NO:22. In some embodiments, the first and/or the second VL domains comprise the amino acid sequence of SEQ ID NO:24, or an amino acid sequence having at least 90%, at least 95%, or at least 99% sequence identity to SEQ ID NO:24. In some embodiments, the first and/or the second VL domains comprise the amino acid sequence of SEQ ID NO:30, or an amino acid sequence having at least 90%, at least 95%, or at least 99% sequence identity to SEQ ID NO:30. In some embodiments, the antibody light chain comprises, from N-terminus to C-terminus: (a) the first VH domain; (b) a first linker sequence; (c) a first VL domain of the two or more VL domains; (d) a second linker sequence; (e) a second VL domain of the two or more VL domains; and (f) the CL domain. In some embodiments, the CL domain is a kappa CL domain. In some embodiments, the first linker sequence comprises five repeats of SEQ ID NO:25. In some embodiments, the second linker sequence comprises the amino acid sequence of SEQ ID NO:28. In some embodiments, the antibody light chain comprises the amino acid sequence of SEQ ID NO:7, or an amino acid sequence having at least 90%, at least 95%, or at least 99% sequence identity to SEQ ID NO:7. In some embodiments, the antibody light chain is encoded by a polynucleotide comprising the polynucleotide sequence of SEQ ID NO:8. In some embodiments, the antibody light chain comprises, from N-terminus to C-terminus: (a) a first VL domain of the two VL domains; (b) the CL domain; (c) a first linker sequence; (d) the first VH domain; (e) a second linker sequence; and (f) a second VL domain of the two VL domains. In some embodiments, the CL domain is a kappa CL domain. In some embodiments, the first linker sequence comprises two repeats of SEQ ID NO:25. In some embodiments, the second linker sequence comprises five repeats of SEQ ID NO:25. In some embodiments, the antibody light chain comprises the amino acid sequence of SEQ ID NO:9. In some embodiments, the antibody light chain is encoded by a polynucleotide comprising the polynucleotide sequence of SEQ ID NO:10. In some embodiments, the antibody heavy chain comprises, from N-terminus to C-terminus: (a) the second VH domain; and (b) a heavy chain constant region comprising a first heavy chain constant region (CH1) domain, an antibody hinge region, an second heavy chain constant region (CH2) domain, and a third heavy chain constant region (CH3) domain. In some embodiments, the antibody heavy chain comprises the amino acid sequence of SEQ ID NO:11, or an amino acid sequence having at least 90%, at least 95%, or at least 99% sequence identity to SEQ ID NO:11. In some embodiments, the antibody heavy chain is encoded by a polynucleotide comprising the polynucleotide sequence of SEQ ID NO:12.

In another aspect, provided herein is a tetravalent antibody that specifically binds to human PSGL-1, the tetravalent antibody comprising a dimer of two monomers, wherein each monomer of the dimer comprises an antibody heavy chain and an antibody light chain; wherein the antibody light chain comprises: (i) a first heavy chain variable (VH) domain, (ii) a first light chain variable (VL) domain, and (iii) a light chain constant (CL) domain; wherein the antibody heavy chain comprises: (i) a second heavy chain variable (VH) domain, (ii) a second light chain variable (VL) domain, and (iii) a heavy chain constant domain comprising a first heavy chain constant region (CH1) domain, an antibody hinge region, an second heavy chain constant region (CH2) domain, and a third heavy chain constant region (CH3) domain; wherein each of the first and second VL domains comprises a CDR-L1, a CDR-L2, and a CDR-L3; wherein each of the first and second VH domains comprises a CDR-H1, a CDR-H2, and a CDR-H3; wherein each of the first and second VL domains forms a VH-VL binding unit with a corresponding VH domain of the first and second VH domains; and wherein each of the two VH-VL binding units is specific for human PSGL-1. In some embodiments, at least one of the first and second VH domains comprises: (i) a CDR-H1 comprising the amino acid sequence of SEQ ID NO:17; (ii) a CDR-H2 comprising the amino acid sequence of SEQ ID NO:18; and (iii) a CDR-H3 comprising the amino acid sequence of SEQ ID NO:19. In some embodiments, the first and the second VH domains each comprise: (i) a CDR-H1 comprising the amino acid sequence of SEQ ID NO:17; (ii) a CDR-H2 comprising the amino acid sequence of SEQ ID NO:18; and (iii) a CDR-H3 comprising the amino acid sequence of SEQ ID NO:19. In some embodiments, the first and/or the second VH domains comprise the amino acid sequence of SEQ ID NO:23. In some embodiments, the first and/or the second VH domains comprise the amino acid sequence of SEQ ID NO:29. In some embodiments, at least one of the first and second VL domains comprises: (i) a CDR-L1 comprising the amino acid sequence of SEQ ID NO:20; (ii) a CDR-L2 comprising the amino acid sequence of SEQ ID NO:21; and (iii) a CDR-L3 comprising the amino acid sequence of SEQ ID NO:22. In some embodiments, the first and the second VL domains each comprise: (i) a CDR-L1 comprising the amino acid sequence of SEQ ID NO:20; (ii) a CDR-L2 comprising the amino acid sequence of SEQ ID NO:21; and (iii) a CDR-L3 comprising the amino acid sequence of SEQ ID NO:22. In some embodiments, the first and/or the second VL domains comprise the amino acid sequence of SEQ ID NO:24. In some embodiments, the first and/or the second VL domains comprise the amino acid sequence of SEQ ID NO:30. In some embodiments, the antibody light chain comprises, from N-terminus to C-terminus: (a) the first VH domain; (b) a first linker sequence; (c) the first VL domain; and (d) the CL domain. In some embodiments, the CL domain is a kappa CL domain. In some embodiments, the first linker sequence comprises five repeats of SEQ ID NO:25. In some embodiments, the antibody light chain comprises the amino acid sequence of SEQ ID NO:13. In some embodiments, the antibody light chain is encoded by a polynucleotide comprising the polynucleotide sequence of SEQ ID NO:14. In some embodiments, the antibody heavy chain comprises, from N-terminus to C-terminus: (a) the second VH domain; (b) a second linker sequence; (c) the second VL domain; and (d) the heavy chain constant region comprising the first heavy chain constant region (CH1) domain, the antibody hinge region, the second heavy chain constant region (CH2) domain, and the third heavy chain constant region (CH3) domain. In some embodiments, the second linker sequence comprises five repeats of SEQ ID NO:25. In some embodiments, the antibody heavy chain comprises the amino acid sequence of SEQ ID NO:15. In some embodiments, the antibody heavy chain is encoded by a polynucleotide comprising the polynucleotide sequence of SEQ ID NO:16.

In some embodiments of any of the above embodiments, the antibody Fc domain is a human antibody Fc domain. In some embodiments, the antibody Fc domain is a human IgG4 Fc domain. In some embodiments, the human IgG4 Fc domain comprises a hinge region sequence comprising one or more amino acid substitutions that result in reduced IgG4 shuffling, as compared to an IgG4 hinge region lacking the one or more amino acid substitutions. In some embodiments, the human IgG4 Fc domain comprises a hinge region sequence comprising a serine to proline substitution at amino acid 228, numbering according to EU index. In some embodiments of any of the above embodiments, the antibody hinge region comprises a serine to proline substitution at amino acid 228, numbering according to EU index. In some embodiments, a tetravalent antibody of the present disclosure displays enhanced induction of apoptosis in a target cell (e.g., a cell expressing human PSGL-1 or an epitope thereof) as compared to a conventional (e.g., bivalent) antibody having one or more VH or VL domains in common with the tetravalent antibody. In some embodiments, a tetravalent antibody of the present disclosure displays enhanced inhibition of DTH (e.g., in a trans vivo animal model) as compared to a conventional (e.g., bivalent) antibody having one or more VH or VL domains in common with the tetravalent antibody.

In another aspect, provided herein is an isolated polynucleotide encoding the tetravalent antibody of any one of the above embodiments. In some embodiments, the isolated polynucleotide comprises a polynucleotide sequence selected from the group consisting of SEQ ID NOs:2, 4, 6, 8, 10, 12, 14, and 16. In another aspect, provided herein is a vector comprising the isolated polynucleotide of any of the above embodiments. In another aspect, provided herein is a host cell comprising the polynucleotide of any of the above embodiments and/or the vector of any of the above embodiments. In another aspect, provided herein is a method of producing a tetravalent antibody comprising culturing the host cell of any of the above embodiments so that the tetravalent antibody is produced. In some embodiments, the method further comprises recovering the tetravalent antibody from the host cell.

In another aspect, provided herein is a pharmaceutical composition comprising the tetravalent antibody of any one of the above embodiments and a pharmaceutically acceptable carrier. In another aspect, provided herein is a kit comprising the tetravalent antibody of any one of the above embodiments and an optional pharmaceutically acceptable carrier. In some embodiments, the kit further comprises a package insert comprising instructions for administration of the tetravalent antibody to treat a T-cell mediated inflammatory disease or condition. In some embodiments, the kit further comprises a package insert comprising instructions for administration of the tetravalent antibody before, concurrently with, and/or after a transfusion or transplantation. In another aspect, provided herein is the tetravalent antibody of any one of the above embodiments for use in treating a T-cell mediated inflammatory disease or condition. In another aspect, provided herein is the tetravalent antibody of any one of the above embodiments for use in treating an individual in need of a transfusion or transplantation. In another aspect, provided herein is a use of the tetravalent antibody of any one of the above embodiments in the manufacture of a medicament for treating a T-cell mediated inflammatory disease or condition. In another aspect, provided herein is a use of the tetravalent antibody of any one of the above embodiments in the manufacture of a medicament for treating an individual in need of a transfusion or transplantation. In another aspect, provided herein is a method of treating a T-cell mediated inflammatory disease or condition, the method comprising administering to a subject in need thereof a therapeutically effective amount of the tetravalent antibody of any one of the above embodiments. In another aspect, provided herein is a method for treating an individual in need of a transfusion or transplantation, comprising administering to the individual a therapeutically effective amount of the tetravalent antibody of any one of the above embodiments before, concurrently with, and/or after the transfusion or transplantation. In some embodiments, the T-cell mediated inflammatory disease is an autoimmune disease. In some embodiments, the T-cell mediated inflammatory disease is selected from the group consisting of psoriasis, psoriatic arthritis, rheumatoid arthritis, Crohn's disease, ankylosing spondylitis, type I diabetes, ulcerative colitis, multiple sclerosis, and graft versus host disease (GVHD). In some embodiments, the psoriasis is plaque psoriasis, chronic plaque psoriasis, guttate psoriasis, inverse psoriasis, pustular psoriasis, or erythrodermic psoriasis. In some embodiments, the transplantation is a transplantation of a tissue selected from the group consisting of bone marrow, kidney, heart, liver, neuronal tissue, lung, pancreas, skin, and intestine. In some embodiments, the transfusion is a transfusion comprising one or more of white blood cells, red blood cells, and platelets.

It is to be understood that one, some, or all of the properties of the various embodiments described herein may be combined to form other embodiments of the present invention. These and other aspects of the invention will become apparent to one of skill in the art.

BRIEF DESCRIPTION OF THE DRAWINGS

FIG. 1A illustrates the following exemplary formats: (1) a dimer composed of two single-chain diabodies fused to an Fc domain ($scDb_2$-Fc), showing linker sequences: $(GGGGS)_5$ (SEQ ID NO:33), GGGGSAAA (SEQ ID NO:26) and $(GGGGS)_2$ (SEQ ID NO:34)/$(GGGGS)_2G$ (SEQ ID NO:35)/$(GGGGS)_2GG$ (SEQ ID NO:36); (2) two different formats, each having a dimer of two tandem single-chain variable fragment units ($taFv_2$-Fc), showing identical linker sequences for both formats: $(GGGGS)_5$ (SEQ ID NO:33), ASTGS (SEQ ID NO:27), GGGGSAAA (SEQ ID NO:26); and (3) three different formats based on single-chain variable fragments (scFv-IgG), showing: $scFv_2$-LC-IgG4p linker sequences $(GGGGS)_5$ (SEQ ID NO:33) and $ASTGSG_4S$ (SEQ ID NO:28), LC-$scFv_2$-IgG4p linker sequences $(GGGGS)_2$ (SEQ ID NO:34) and $(GGGGS)_5$ (SEQ ID NO:33), $scFv_4$-crIG4p linker sequences $(GGGGS)_5$ (SEQ ID NO:33). FIG. 1B provides another illustration of the three scFv-based formats, with the variable fragments shaded and V2 scFvs indicated.

DETAILED DESCRIPTION

Figure 1A:
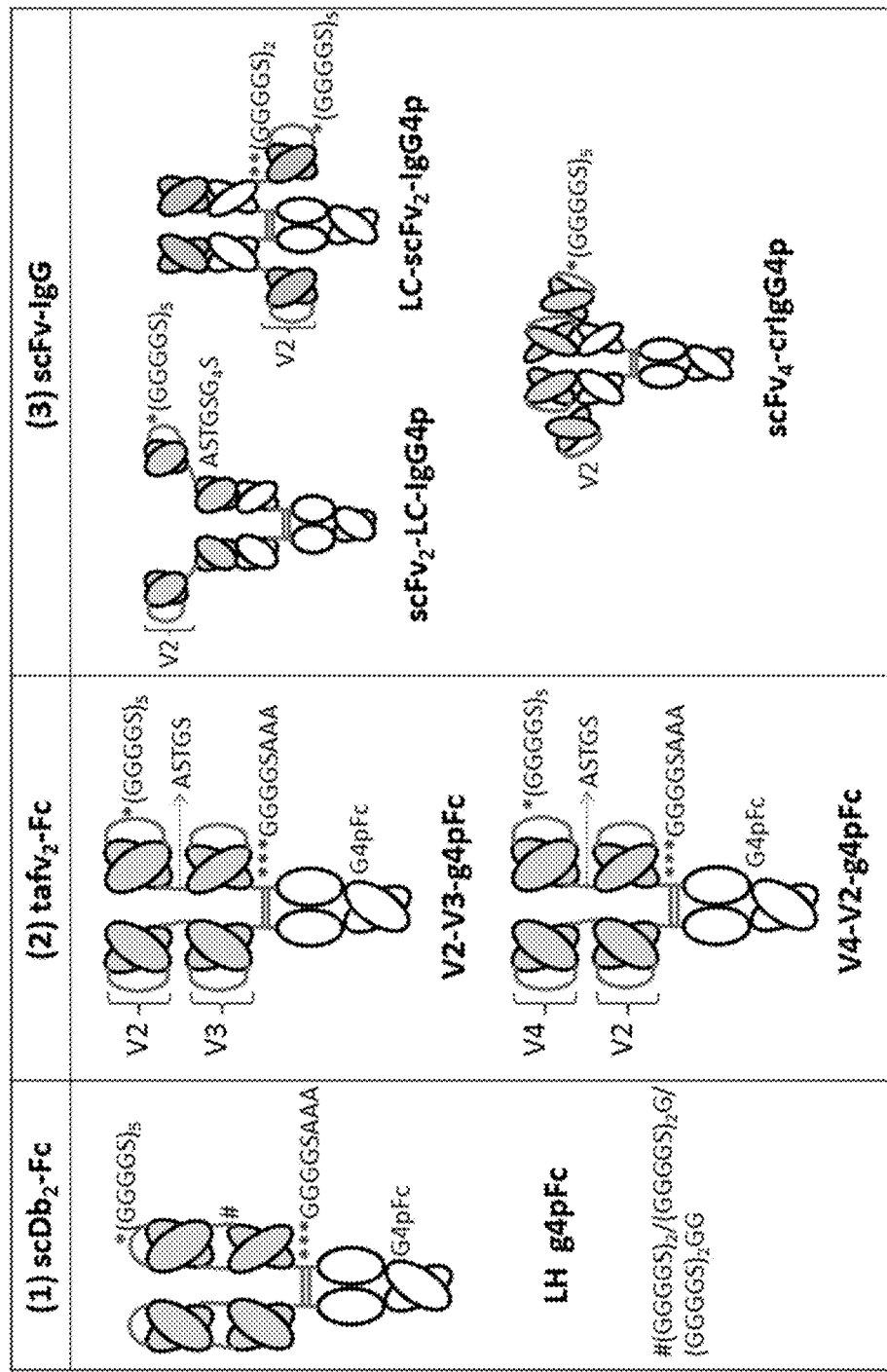
FIGS. 1A & 1B provide schematics illustrating exemplary tetravalent antibodies in accordance with some embodiments.

Provided herein are tetravalent antibodies that specifically bind to human PSGL-1. The present disclosure is based at least in part on the finding described herein that certain tetravalent anti-PSGL-1 antibodies show enhanced efficacy compared to the parental anti-PSGL-1 antibody both in vitro and trans vivo. These tetravalent antibodies displayed higher potency for apoptosis induction and enhanced efficacy in a trans vivo model for delayed type hypersensitivity (DTH) than the parental anti-PSGL-1 antibody. Further provided herein are isolated polynucleotides, vectors, host cells, pharmaceutical compositions, kits, uses, and methods related to the tetravalent antibodies. For example, the tetravalent antibodies of the present disclosure may find use in treating a T-cell mediated inflammatory disease, or administration before, concurrently with, and/or after a transfusion or transplantation.

In some embodiments, the tetravalent antibodies of the present disclosure comprise a dimer of two monomers, wherein each monomer of the dimer comprises a single-chain polypeptide comprising: (a) two light chain variable (VL) domains, wherein each of the two VL domains comprises a CDR-L1, a CDR-L2, and a CDR-L3; (b) two heavy chain variable (VH) domains, wherein each of the two VH domains comprises a CDR-H1, a CDR-H2, and a CDR-H3; and (c) an antibody Fc domain, wherein each of the two VL domains forms a VH-VL binding unit with a corresponding VH domain of the two VH domains, and wherein each of the two VH-VL binding units is specific for human PSGL-1. In other embodiments, the tetravalent antibodies of the present disclosure comprise a dimer of two monomers, wherein each monomer of the dimer comprises an antibody heavy chain and an antibody light chain; wherein the antibody light chain comprises: (i) two light chain variable (VL) domains, wherein each of the two VL domains comprises a CDR-L1, a CDR-L2, and a CDR-L3, (ii) a first heavy chain variable (VH) domain, and (iii) a light chain constant (CL) domain; wherein the antibody heavy chain comprises: (i) a second heavy chain variable (VH) domain, and (ii) a heavy chain constant region comprising a first heavy chain constant region (CH1) domain, an antibody hinge region, an second heavy chain constant region (CH2) domain, and a third heavy chain constant region (CH3) domain; wherein the first and the second VH domains each comprise a CDR-H1, a CDR-H2, and a CDR-H3, wherein each of the two VL domains forms a VH-VL binding unit with a corresponding VH domain of the first and the second VH domains, and wherein each of the two VH-VL binding units is specific for human PSGL-1. In other embodiments, the tetravalent antibodies of the present disclosure comprise a dimer of two monomers, wherein each monomer of the dimer comprises an antibody heavy chain and an antibody light chain; wherein the antibody light chain comprises: (i) a first heavy chain variable (VH) domain, (ii) a first light chain variable (VL) domain, and (iii) a light chain constant (CL) domain; wherein the antibody heavy chain comprises: (i) a second heavy chain variable (VH) domain, (ii) a second light chain variable (VL) domain, and (iii) a heavy chain constant region comprising a first heavy chain constant region (CH1) domain, an antibody hinge region, an second heavy chain constant region (CH2) domain, and a third heavy chain constant region (CH3) domain; wherein each of the first and second VL domains comprises a CDR-L1, a CDR-L2, and a CDR-L3; wherein each of the first and second VH domains comprises a CDR-H1, a CDR-H2, and a CDR-H3; wherein each of the first and second VL domains forms a VH-VL binding unit with a corresponding VH domain of the first and second VH domains; and wherein each of the two VH-VL binding units is specific for human PSGL-1.

I. Definitions

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also polypeptides comprising fragments thereof (such as Fab, Fab', F(ab')$_2$, Fv); single-chain variable fragments (scFv), single-chain diabodies (scDbs), tandem single-chain variable fragment (scFv) units (termed taFv for tandem scFv), and mutants or other configurations thereof; fusion proteins comprising an antibody portion; and any other modified configuration of the immunoglobulin molecule that comprises an antigen recognition site.

As used herein, a "tetravalent" antibody may refer to an antibody that comprises four antibody VH-VL binding units, with each VH-VL binding unit comprising an antibody VH domain and an antibody VL domain. As used herein, references to a "monomer" of a tetravalent antibody may include both single-chain polypeptides and multiple-chain polypeptides. For example, a monomer may refer to a single-chain polypeptide, or it may refer to an antibody heavy chain-light chain unit, where the heavy chain and light chain are encoded by separate polynucleotides and/or are formed from the association of separate polypeptides.

An antibody includes an antibody of any class, such as IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of immunoglobulins are called alpha, delta, epsilon, gamma, and mu, respectively. The subunit structures and three-dimensional configurations of different classes of immunoglobulins are well known.

The antibodies of the present disclosure are further intended to include bispecific, multispecific, chimeric, humanized, and recombinantly constructed molecules having affinity for a polypeptide conferred by at least one CDR region of the antibody. Single domain antibodies which are either the variable domain of an antibody heavy chain or the variable domain of an antibody light chain are known in the art. See, e.g., Holt et al., *Trends Biotechnol.* 21:484-490, 2003. Methods of making antibodies comprising either the variable domain of an antibody heavy chain or the variable domain of an antibody light chain, containing three of the six naturally occurring complementarity determining regions from an antibody, are also known in the art. See, e.g., Muyldermans, *Rev. Mol. Biotechnol.* 74:277-302, 2001.

As used herein, "monoclonal antibody" refers to an antibody of substantially homogeneous antibodies, i.e., the individual antibodies comprising the population are identical except for possible naturally-occurring mutations that may be present in minor amounts. Monoclonal antibodies are generally highly specific, being directed against a single antigenic site. Furthermore, in contrast to polyclonal antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by the hybridoma method first described by Kohler and Milstein, 1975, Nature, 256:495, or may be made by recombinant DNA methods such as described in U.S. Pat. No. 4,816,567. The monoclonal antibodies may also be isolated from phage libraries generated using the techniques described in McCafferty et al., 1990, Nature, 348:552-554, for example.

As used herein, a "chimeric antibody" refers to an antibody having a variable region or part of a variable region from a first species and a constant region from a second species. An intact chimeric antibody comprises two copies of a chimeric light chain and two copies of a chimeric heavy chain. The production of chimeric antibodies is known in the art (Cabilly et al. (1984), *Proc. Natl. Acad. Sci. USA,* 81:3273-3277; Harlow and Lane (1988), *Antibodies: a Laboratory Manual*, Cold Spring Harbor Laboratory). Typically, in these chimeric antibodies, the variable region of both light and heavy chains mimics the variable regions of antibodies derived from one species of mammal, while the constant portions are homologous to the sequences in antibodies derived from another. One clear advantage to such chimeric forms is that, for example, the variable regions can conveniently be derived from presently known sources using readily available hybridomas or B-cells from non-human host organisms in combination with constant regions derived from, for example, human cell preparations. While the variable region has the advantage of ease of preparation, and the specificity is not affected by its source, the constant region being human is less likely to elicit an immune response from a human subject when the antibodies are injected than would the constant region from a non-human source. However, the definition is not limited to this particular example. In some embodiments, amino acid modifications are made in the variable and/or constant region.

As used herein, "humanized" antibodies refer to forms of non-human (e.g., murine) antibodies that are specific chimeric immunoglobulins, immunoglobulin chains, or fragments thereof (such as Fv, Fab, Fab', F(ab')$_2$, or other antigen-binding subsequences of antibodies) that contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (e.g., an Fc domain), typically that of a human immunoglobulin. Antibodies may have Fc regions modified as described in WO 99/58572. Other forms of humanized antibodies have one or more CDRs (one, two, three, four, five, or six) which are altered with respect to the original antibody, which are also termed one or more CDRs "derived from" one or more CDRs from the original antibody.

As used herein, "human antibody" means an antibody having an amino acid sequence corresponding to that of an antibody produced by a human and/or has been made using any of the techniques for making human antibodies known in the art or disclosed herein. This definition of a human antibody includes antibodies comprising at least one human heavy chain polypeptide or at least one human light chain polypeptide. One such example is an antibody comprising murine light chain and human heavy chain polypeptides. Human antibodies can be produced using various techniques known in the art. In one embodiment, the human antibody is selected from a phage library, where that phage library expresses human antibodies (Vaughan et al., 1996, Nature Biotechnology, 14:309-314; Sheets et al., 1998, PNAS, (USA) 95:6157-6162; Hoogenboom and Winter, 1991, J. Mol. Biol., 227:381; Marks et al., 1991, J. Mol. Biol., 222:581). Human antibodies can also be made by introducing human immunoglobulin loci into transgenic animals, e.g., mice in which the endogenous immunoglobulin genes have been partially or completely inactivated. This approach is described in U.S. Pat. Nos. 5,545,807; 5,545,806; 5,569,825; 5,625,126; 5,633,425; and 5,661,016. Alternatively, the human antibody may be prepared by immortalizing human B-lymphocytes that produce an antibody directed against a target antigen (such B-lymphocytes may be recovered from an individual or may have been immunized in vitro). See, e.g., Cole et al., Monoclonal Antibodies and Cancer Therapy, Alan R. Liss, p. 77 (1985); Boerner et al., 1991, J. Immunol., 147 (1):86-95; and U.S. Pat. No. 5,750,373.

A "variable region" (the term "variable domain" may be used interchangeably herein) of an antibody refers to the variable region of the antibody light chain (VL) or the variable region of the antibody heavy chain (VH), either alone or in combination. The variable regions of the heavy and light chain (VH and VL domains, respectively) each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-lazikani et al (1997) J. Molec. Biol. 273:927-948)). As used herein, a CDR may refer to CDRs defined by either approach or by a combination of both approaches.

A number of HVR delineations are in use and are encompassed herein. The Kabat Complementarity Determining Regions (CDRs) are based on sequence variability and are the most commonly used (Kabat et al., *Sequences of Proteins of Immunological Interest,* 5th Ed. Public Health Service, National Institutes of Health, Bethesda, Md. (1991)). Chothia refers instead to the location of the structural loops (Chothia and Lesk, *J. Mol. Biol.* 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs are noted below.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B (Kabat numbering) |
| H1 | H31-H35 | H26-H35 | H26-H32 | H30-H35 (Chothia numbering) |
| H2 | H50-H65 | H50-H58 | H53-H55 | H47-H58 |
| H3 | H95-H102 | H95-H102 | H96-H101 | H93-H101 |

The Kabat numbering system is generally used when referring to a residue in the variable domain (approximately residues 1-107 of the light chain and residues 1-113 of the heavy chain) (e.g., Kabat et al., Sequences *of Immunological Interest.* 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra, or and Edelman, G. M. et al. (1969) *Proc. Natl. Acad. Sci. USA* 63:78-85).

"Fv" as used herein may refer to the minimum antibody fragment which contains a complete antigen-recognition and -binding site. This fragment typically consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three HVRs specific for an antigen) has the ability to recognize and bind antigen, although at a lower affinity than the entire binding site.

A "constant region" (the term "constant domain" may be used interchangeably herein) of an antibody refers to the constant region of the antibody light chain (CL) or the constant region of the antibody heavy chain (CH), either alone or in combination. A constant region of an antibody generally provides structural stability and other biological functions such as antibody chain association, secretion, transplacental mobility, and complement binding, but is not involved with binding to the antigen. The amino acid sequence and corresponding exon sequences in the genes of the constant region is dependent upon the species from which it is derived; however, variations in the amino acid sequence leading to allotypes is relatively limited for particular constant regions within a species. The variable region of each chain is joined to the constant region by a linking polypeptide sequence. The linkage sequence is coded by a "J" sequence in the light chain gene, and a combination of a "D" sequence and a "J" sequence in the heavy chain gene. Depending on the antibody isotype, a heavy chain constant region may include a CH1 domain, a hinge region, a CH2 domain, a CH3 domain, and/or a CH4 domain. In certain embodiments, a heavy chain constant region comprises a CH1 domain, a hinge region, a CH2 domain, and a CH3 domain.

The term "Fc region" (the term "Fc domain" may be used interchangeably herein) herein is used to define a C-terminal region of an immunoglobulin heavy chain, including native-sequence Fc regions and variant Fc regions. The boundaries of the Fc region of an immunoglobulin heavy chain might vary; in some embodiments, the Fc region may include one or more amino acids of the hinge region. In some embodiments, the human IgG heavy-chain Fc region is defined to stretch from an amino acid residue at EU position 216 to the carboxyl-terminus thereof. Suitable native-sequence Fc regions for use in the antibodies of the present disclosure include human IgG1, IgG2 (IgG2A, IgG2B), IgG3 and IgG4.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains which enables the sFv to form the desired structure for antigen binding. For a review of the sFv, see Pluckthun in *The Pharmacology of Monoclonal Antibodies*, vol. 113, Rosenburg and Moore eds., Springer-Verlag, New York, pp. 269-315 (1994).

The term "diabodies" refers to antibody fragments prepared by constructing sFv fragments (see preceding paragraph) with short linkers (e.g., about 5-12 residues) between the $V_H$ and $V_L$ domains such that inter-chain but not intra-chain pairing of the V domains is achieved, thereby resulting in a bivalent fragment, i.e., a fragment having two antigen-binding sites. Bispecific diabodies are heterodimers of two "crossover" sFv fragments in which the $V_H$ and $V_L$ domains of the two antibodies are present on different polypeptide chains. Diabodies are described in greater detail in, for example, EP 404,097; WO 93/11161; Hollinger et al., *Proc. Natl. Acad. Sci. USA* 90: 6444-6448 (1993).

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared.

As used herein, "antibody-dependent cell-mediated cytotoxicity" and "ADCC" refer to a cell-mediated reaction in which nonspecific cytotoxic cells that express Fc receptors (FcRs) (e.g., natural killer (NK) cells, neutrophils, or macrophages) recognize bound antibody on a target cell and subsequently cause lysis of the target cell. ADCC activity of a molecule of interest can be assessed using an in vitro ADCC assay, such as that described in U.S. Pat. No. 5,500,362 or 5,821,337. Useful effector cells for such assays include peripheral blood mononuclear cells (PBMC) and NK cells. Alternatively, or additionally, ADCC activity of the molecule of interest may be assessed in vivo, e.g., in a animal model such as that disclosed in Clynes et al., 1998, PNAS (USA), 95:652-656.

"Complement dependent cytotoxicity" and "CDC" refer to the lysing of a target in the presence of complement. The complement activation pathway is initiated by the binding of the first component of the complement system (C1q) to a molecule (e.g., an antibody) complexed with a cognate antigen. To assess complement activation, a CDC assay, e.g., as described in Gazzano-Santoro et al., J. Immunol. Methods, 202:163 (1996), may be performed.

The terms "polypeptide," "oligopeptide," "peptide," and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of the present disclosure are based upon a tetravalent antibody, the polypeptides can occur as single chains or associated chains.

"Polynucleotide," or "nucleic acid," as used interchangeably herein, refer to polymers of nucleotides of any length, and include DNA and/or RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, cabamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, α-anomeric sugars, epimeric sugars such as arabinose, xyloses, lyxoses, pyranose sugars, furanose sugars, sedoheptuloses, acyclic analogs, and abasic nucleoside analogs such as methyl ribosides. One or more phosphodiester linkages may be replaced by alternative linking groups. These alternative linking groups include, but are not limited to, embodiments wherein phosphate is replaced by P(O)S("thioate"), P(S)S ("dithioate"), "(O)NR$_2$ ("amidate"), P(O)R, P(O)OR', CO, or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl, or araldyl. Not all linkages in a polynucleotide need be identical. The preceding description applies to all polynucleotides referred to herein, including RNA and DNA.

As used herein, "vector" means a construct that is capable of delivering and desirably expressing one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

As used herein, an "effective dosage" or "therapeutically effective amount" of drug, compound, or pharmaceutical composition is an amount sufficient to effect beneficial, desired, and/or therapeutic results. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. In the case of treating an individual awaiting a transplantation, for example, an effective amount of the drug may reduce to some extent the level of alloantibodies and/or PRA in the individual. In the case of treating an individual receiving a transplantation or transfusion, an effective amount of the drug may have the effect in and/or relieving to some extent one or more of the symptoms or conditions (such as graft rejection) associated with the transplantation or transfusion. An effective amount can be administered in one or more administrations. For purposes of the present disclosure, an effective amount of drug, compound, or pharmaceutical composition is an amount sufficient to accomplish prophylactic or therapeutic treatment either directly or indirectly. An effective dosage can be administered in one or more administrations. For purposes of the present disclosure, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

As used herein, "in conjunction with" refers to administration of one treatment modality in addition to another treatment modality. As such, "in conjunction with" refers to administration of one treatment modality before, during, or after administration of the other treatment modality to the individual.

As used herein, "treatment" or "treating" is an approach for obtaining beneficial or desired results, including desirably clinical results. Beneficial, desired, and/or therapeutic clinical results include, but are not limited to, one or more of the following: reducing or abrogating one or more symptoms of inflammation or autoimmunity (e.g., stemming from a T-cell mediated inflammatory disease), increasing the likelihood of a successful patient outcome and/or mitigating one or more contraindications or detrimental outcomes related to a medical treatment (e.g., related to a transplantation or transfusion), decreasing symptoms resulting from the disease, increasing the quality of life of those suffering from the disease, decreasing the dose of other medications required to treat the disease, delaying the progression of the disease, and/or prolonging survival of individuals.

As used herein, "delaying development of a disease" means to defer, hinder, slow, retard, stabilize, and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a symptom of an inflammatory disease, such as a T-cell mediated inflammatory disease, may be delayed.

An "individual" or a "subject" is a mammal, more desirably a human. Mammals also include, but are not limited to, farm animals, sport animals, pets (such as cats, dogs, or horses), primates, mice, and rats.

As used herein, the term "specifically recognizes" or "specifically binds" refers to measurable and reproducible interactions such as attraction or binding between a target and an antibody (e.g., a full-length antibody, an antibody fragment, or an antibody VH-VL binding unit) that is determinative of the presence of the target in the presence of a heterogeneous population of molecules including biological molecules. For example, an antibody, antibody fragment, or antibody VH-VL binding unit that specifically or preferentially binds to an epitope is an antibody that binds this epitope with greater affinity, avidity, more readily, and/or with greater duration than it binds to other epitopes of the target or non-target epitopes. It is also understood by reading this definition that, for example, an antibody, antibody fragment, or antibody VH-VL binding unit that specifically or preferentially binds to a first target may or may not specifically or preferentially bind to a second target. As such, "specific binding" or "preferential binding" does not necessarily require (although it can include) exclusive binding. An antibody, antibody fragment, or antibody VH-VL binding unit that specifically binds to a target may have an association constant of greater than or about $10^3$ $M^{-1}$ or about $10^4$ $M^{-1}$, sometimes about $10^5$ $M^{-1}$ or about $10^6$ $M^{-1}$, in other instances about $10^6$ $M^{-1}$ or about $10^7$ $M^{-1}$, about $10^8$ $M^{-1}$ to about $10^9$ $M^{-1}$, or about $10^{10}$ $M^{-1}$ to about $10^{11}$ $M^{-1}$ or higher. A variety of immunoassay formats can be used to select antibodies, antibody fragments, or antibody VH-VL binding units that are specifically immunoreactive with a particular protein. For example, solid-phase ELISA immunoassays are routinely used to select monoclonal antibodies specifically immunoreactive with a protein. See, e.g., Harlow and Lane (1988) Antibodies, A Laboratory Manual, Cold Spring Harbor Publications, New York, for a description of immunoassay formats and conditions that can be used to determine specific immunoreactivity.

A "package insert" refers to instructions customarily included in commercial packages of medicaments that contain information about the indications customarily included in commercial packages of medicaments that contain information about the indications, usage, dosage, administration, contraindications, other medicaments to be combined with the packaged product, and/or warnings concerning the use of such medicaments, etc.

As used herein and in the appended claims, the singular forms "a," "an," and "the" include plural reference unless the context clearly indicates otherwise. For example, reference to an "antibody" is a reference to from one to many antibodies, such as molar amounts, and includes equivalents thereof known to those skilled in the art, and so forth.

Reference to "about" a value or parameter herein includes (and describes) embodiments that are directed to that value or parameter per se. For example, description referring to "about X" includes description of "X."

It is understood that aspect and variations of the present disclosure described herein include "consisting" and/or "consisting essentially of" aspects and variations.

II. Tetravalent Antibodies

Certain aspects of the present disclosure relate to tetravalent antibodies that specifically bind to human PSGL-1. In some embodiments, a tetravalent antibody of the present disclosure comprises a dimer of two monomers. As described infra, the monomers may be coupled using any means known in the art, including without limitation wild-type interactions between antibody Fc domains or regions, altered or mutated interactions between antibody Fc domains or regions (e.g., using a hinge region mutation described herein), or other artificial covalent or non-covalent interactions (e.g., cross-linking or a linker). Exemplary tetravalent antibodies and antibody formats are described below and illustrated in FIGS. 1A & 1B.

Human PSGL-1 may also be referred to as selectin P ligand, SELPG, CLA, CD162, or PSGL1. In some embodiments, a tetravalent antibody of the present disclosure binds to a polypeptide encoded by the human SELPG gene, e.g., as described by NCBI RefSeq Gene ID No. 6404. In some embodiments, a tetravalent antibody of the present disclosure binds to a human PSGL-1 polypeptide containing 15 or 16 decamer repeats. In some embodiments, a tetravalent antibody of the present disclosure binds to a polypeptide comprising the amino acid sequence of SEQ ID NO:31. In some embodiments, a tetravalent antibody of the present disclosure binds to a polypeptide comprising the amino acid sequence of SEQ ID NO:32. In some embodiments, a tetravalent antibody of the present disclosure binds to a polypeptide comprising the amino acid sequence of SEQ ID NO:31 and binds to a polypeptide comprising the amino acid sequence of SEQ ID NO:32. The amino acid sequence of SEQ ID NO:31 depicts full length human PSGL-1, GenBank™ accession number AAA74577.1, GL902797, and the amino acid sequence of SEQ ID NO:32 depicts the shorter 402 amino acid human PSGL-1 protein (GenBank™ accession number XP_005269133). In specific embodiments, a tetravalent antibody described herein specifically binds to human PSGL-1 as determined, e.g., by ELISA or other antigen-binding assay known in the art, or described herein.

In some embodiments, a VH domain and a VL domain of the present disclosure form a VH-VL binding unit (e.g., that specifically binds an epitope, such as an epitope of human PSGL-1). As described herein, a VH-VL binding unit may be formed between a VH domain and a VL domain using wild-type VH-VL interactions, or a VH-VL binding unit may be further stabilized using one or more mutations or chemical bonds (e.g., a disulfide bond, such as the vH44-vL100 disulfide bond introduced by cysteine substitutions in the VH and VL domain of SEQ ID NOs: 29 and 30, respectively).

In some embodiments, a tetravalent antibody of the present disclosure comprises a dimer of two monomers, where each monomer of the dimer comprises a single-chain polypeptide.

In some embodiments, a single-chain, heavy chain, and/or light chain polypeptide of the present disclosure comprises a linker sequence. A variety of linker sequences may suitably be used, e.g., to link VH and VL domains of a VH-VL binding unit, to link a VH or VL domain of a VH-VL binding unit to a VH or VL domain of another VH-VL binding unit, or to link a VH or VL domain of a VH-VL binding unit to an antibody constant region, such as an Fc domain or region. In some embodiments, a linker of the present disclosure may be present between domains or regions. In some embodiments, two domains or regions of the present disclosure may be joined without a linker, or the linker joining two domains or regions may be removed. Coupling of such single-chain fragments using various linkers is described in Kortt et al., 1997, *Protein Engineering*, 10:423-433. In some embodiments, a linker sequence of the present disclosure comprises 1-50 amino acids. In certain embodiments, a linker sequence of the present disclosure comprises 5-12 amino acids. Exemplary linker sequences are described herein and illustrated in FIG. 1A. In some embodiments, a linker sequence of the present disclosure comprises one or more repeats of the amino acid sequence of GGGGS (SEQ ID NO:25). In some embodiments, a linker sequence of the present disclosure comprises two, three, four, or five repeats of the amino acid sequence of GGGGS (SEQ ID NO:25). In some embodiments, a linker sequence of the present disclosure comprises the amino acid sequence of SEQ ID NO:33, 34, 35, or 36. In some embodiments, a linker sequence of the present disclosure comprises the amino acid sequence of GGGGSAAA (SEQ ID NO:26). In some embodiments, a linker sequence of the present disclosure comprises the amino acid sequence of ASTGS (SEQ ID NO:27). In some embodiments, a linker sequence of the present disclosure comprises the amino acid sequence of ASTGSGGGGS (SEQ ID NO:28).

In some embodiments, a tetravalent antibody of the present disclosure comprises a dimer of two single-chain diabodies (scDbs), which may optionally be fused to an antibody constant region, such as an Fc domain.

In some embodiments, each monomer of the dimer comprises a single-chain polypeptide comprising (a) two light chain variable (VL) domains, wherein each of the two VL domains comprises a CDR-L1, a CDR-L2, and a CDR-L3, and wherein the two VL domains are specific for human PSGL-1; (b) two heavy chain variable (VH) domains, wherein each of the two VH domains comprises a CDR-H1, a CDR-H2, and a CDR-H3, and wherein the two VH domains are specific for human PSGL-1; and (c) an antibody Fc domain. In some embodiments, each of the two VL domains forms a VH-VL binding unit with a corresponding VH domain of the two VH domains.

In certain embodiments, each of the two single-chain polypeptides comprises, from N-terminus to C-terminus: (a) a first VL domain of two VL domains; (b) a first linker sequence; (c) a first VH domain of two VH domains; (d) a second linker sequence; (e) a second VL domain of two VL domains; (f) a third linker sequence; (g) a second VH domain of two VH domains; (h) a fourth linker sequence; and (i) an antibody Fc domain. In some embodiments, the first VL domain forms a VH-VL binding unit with the second VH domain, and the first VH domain forms a VH-VL binding unit with the second VL domain.

In some embodiments, the first, second and third linker sequences each comprise two or more repeats of the amino acid sequence of SEQ ID NO:25. In some embodiments, the first, second or third linker sequence comprises the amino acid sequence of SEQ ID NO:33, 34, 35, or 36. In some embodiments, the first and the third linker sequences have the same sequence and comprise two repeats of SEQ ID NO:25. In some embodiments, the second linker sequence comprises five repeats of SEQ ID NO:25. In some embodiments, the fourth linker sequence comprises the amino acid sequence of SEQ ID NO:26.

In some embodiments, a tetravalent antibody of the present disclosure comprises a dimer of two tandem single-chain variable fragment (scFv) units (termed taFv for tandem scFv), which may optionally be fused to an antibody constant domain, such as an Fc domain of a heavy chain constant domain.

In certain embodiments, each of the two single-chain polypeptides comprises, from N-terminus to C-terminus: (a) a first VH domain of the two VH domains; (b) a first linker sequence; (c) a first VL domain of the two VL domains; (d) a second linker sequence; (e) a second VL domain of the two VL domains; (f) a third linker sequence; (g) a second VH domain of the two VH domains; (h) a fourth linker sequence; and (i) an antibody Fc domain. In some embodiments, the first VL domain forms a VH-VL binding unit with the first VH domain, and the second VH domain forms a VH-VL binding unit with the second VL domain. In other embodiments, each of the two single-chain polypeptides comprises, from N-terminus to C-terminus: (a) a first VL domain of the two VL domains; (b) a first linker sequence; (c) a first VH domain of the two VH domains; (d) a second linker sequence; (e) a second VH domain of the two VH domains; (f) a third linker sequence; (g) a second VL domain of the two VL domains; (h) a fourth linker sequence; and (i) the heavy chain constant domain comprising an antibody Fc domain.

In some embodiments, the first and the third linker sequences have the same sequence comprising five repeats of SEQ ID NO:25. In some embodiments, the second linker sequence comprises the amino acid sequence of SEQ ID NO:27. In some embodiments, the fourth linker sequence comprises the amino acid sequence of SEQ ID NO:26.

In some embodiments, a tetravalent antibody of the present disclosure comprises a dimer of two monomers, where each monomer of the dimer comprises an antibody heavy chain and an antibody light chain.

In some embodiments, a tetravalent antibody of the present disclosure comprises a light chain comprising (i) two light chain variable (VL) domains, wherein each of the two VL domains comprises a CDR-L1, a CDR-L2, and a CDR-L3, and wherein the two VL domains are specific for human PSGL-1, (ii) a first heavy chain variable (VH) domain, and (iii) a light chain constant (CL) domain; and/or a heavy chain comprising (i) a second heavy chain variable (VH) domain, and (ii) a heavy chain constant region comprising a first heavy chain constant region (CH1) domain, an antibody hinge region, an second heavy chain constant region (CH2) domain, and a third heavy chain constant region (CH3) domain. In some embodiments, the first and the second VH domains each comprise a CDR-H1, a CDR-H2, and a CDR-H3. In some embodiments, the first and the second VH domains are specific for human PSGL-1. In some embodiments, each of the two VL domains forms a VH-VL binding unit with a corresponding VH domain of the first and the second VH domains.

In certain embodiments, the antibody light chain comprises, from N-terminus to C-terminus: (a) the first VH domain; (b) a first linker sequence; (c) a first VL domain of the two or more VL domains; (d) a second linker sequence; (e) a second VL domain of the two or more VL domains; and (f) the CL domain. In some embodiments, the CL domain is a kappa CL domain. In other embodiments, the CL domain is a lambda CL domain. In some embodiments, the first VL domain forms a VH-VL binding unit with the first VH domain, and the second VH domain forms a VH-VL binding unit with the second VL domain.

In some embodiments, the first linker sequence comprises five repeats of SEQ ID NO:25. In some embodiments, the second linker sequence comprises the amino acid sequence of SEQ ID NO:28.

In some embodiments, a tetravalent antibody of the present disclosure comprises a light chain comprising, from N-terminus to C-terminus: (a) a first VL domain of the two VL domains; (b) the CL domain; (c) a first linker sequence; (d) the first VH domain; (e) a second linker sequence; and (f) a second VL domain of the two VL domains. In some embodiments, the CL domain is a kappa CL domain. In other embodiments, the CL domain is a lambda CL domain.

In some embodiments, the first linker sequence comprises two repeats of SEQ ID NO:25. In some embodiments, the second linker sequence comprises five repeats of SEQ ID NO:25.

In some embodiments, a tetravalent antibody of the present disclosure comprises a heavy chain comprising, from N-terminus to C-terminus: (a) the second of two VH domains; and (b) a heavy chain constant region comprising a first heavy chain constant region (CH1) domain, an antibody hinge region, an second heavy chain constant region (CH2) domain, and a third heavy chain constant region (CH3) domain. In some embodiments, the antibody Fc domain comprises a heavy chain constant 2 (CH2) domain and a heavy chain constant 3 (CH3) domain. In some embodiments, the first VL domain forms a VH-VL binding unit with the first VH domain, and the second VH domain forms a VH-VL binding unit with the second VL domain.

In some embodiments, a tetravalent antibody of the present disclosure comprises a light chain comprising (i) a first heavy chain variable (VH) domain, (ii) a first light chain variable (VL) domain, and (iii) a light chain constant (CL) domain; and/or a heavy chain comprising (i) a second heavy chain variable (VH) domain, (ii) a second light chain variable (VL) domain, and (iii) a heavy chain constant region comprising a first heavy chain constant region (CH1) domain, an antibody hinge region, an second heavy chain constant region (CH2) domain, and a third heavy chain constant region (CH3) domain. In some embodiments, each of the first and second VL domains comprises a CDR-L1, a CDR-L2, and a CDR-L3. In some embodiments, the first and second VL domains are specific for human PSGL-1. In some embodiments, each of the first and second VH domains comprises a CDR-H1, a CDR-H2, and a CDR-H3. In some embodiments, the first and second VH domains are specific for human PSGL-1. In some embodiments, each of the first and second VL domains forms a VH-VL binding unit with a corresponding VH domain of the first and second VH domains.

In some embodiments, the antibody light chain comprises, from N-terminus to C-terminus: (a) the first VH domain; (b) a first linker sequence; (c) the first VL domain; and (d) the CL domain. In some embodiments, the CL domain is a kappa CL domain. In other embodiments, the CL domain is a lambda CL domain.

In some embodiments, the first linker sequence comprises five repeats of SEQ ID NO:25.

In some embodiments, the antibody heavy chain comprises, from N-terminus to C-terminus: (a) the second of two VH domains; (b) a second linker sequence; (c) the second of two VL domains; and (d) a heavy chain constant region comprising a first heavy chain constant region (CH1) domain, an antibody hinge region, an second heavy chain constant region (CH2) domain, and a third heavy chain constant region (CH3) domain. In some embodiments, the antibody Fc domain comprises a heavy chain constant 2 (CH2) domain and a heavy chain constant 3 (CH3) domain.

In some embodiments, the second linker sequence comprises five repeats of SEQ ID NO:25.

In some embodiments, a tetravalent antibody of the present disclosure comprises one or more VH domains comprising one or more CDRs selected from (i) a CDR-H1 comprising the amino acid sequence of SFGMH (SEQ ID NO:17); (ii) a CDR-H2 comprising the amino acid sequence of YINGGSSTIFYANAVKG (SEQ ID NO:18); and (iii) a CDR-H3 comprising the amino acid sequence of YAS-YGGGAMDY (SEQ ID NO:19). In some embodiments, a tetravalent antibody of the present disclosure comprises one or more VH domains comprising (i) a CDR-H1 comprising the amino acid sequence of SEQ ID NO:17; (ii) a CDR-H2 comprising the amino acid sequence of SEQ ID NO:18; and (iii) a CDR-H3 comprising the amino acid sequence of SEQ ID NO:19. In some embodiments, a tetravalent antibody of the present disclosure is a dimer of two monomers, each monomer comprising two VH domains, each VH domain comprising one or more CDRs selected from (i) a CDR-H1 comprising the amino acid sequence of SFGMH (SEQ ID NO:17); (ii) a CDR-H2 comprising the amino acid sequence of YINGGSSTIFYANAVKG (SEQ ID NO:18); and (iii) a CDR-H3 comprising the amino acid sequence of YAS-YGGGAMDY (SEQ ID NO:19). In some embodiments, a tetravalent antibody of the present disclosure is a dimer of two monomers, each monomer comprising two VH domains, each VH domain comprising (i) a CDR-H1 comprising the amino acid sequence of SEQ ID NO:17; (ii) a CDR-H2 comprising the amino acid sequence of SEQ ID NO:18; and (iii) a CDR-H3 comprising the amino acid sequence of SEQ ID NO:19.

In some embodiments, a tetravalent antibody of the present disclosure comprises one or more VH domains comprising the amino acid sequence of SEQ ID NO:23. In some embodiments, a tetravalent antibody of the present disclosure comprises a monomer comprising two VH domains, each VH domain comprising the amino acid sequence of SEQ ID NO:23. In some embodiments, a tetravalent antibody of the present disclosure comprises one or more VH domains comprising the amino acid sequence of SEQ ID NO:29. In some embodiments, a tetravalent antibody of the present disclosure comprises a monomer comprising two VH domains, each VH domain comprising the amino acid sequence of SEQ ID NO:29.

In some embodiments, a tetravalent antibody of the present disclosure comprises one or more VH domains comprising a sequence having at least 90%, 91%, 92%, 93%, 94%, 95%, 96%, 97%, 98%, 99%, or 100% sequence identity to the amino acid sequence of SEQ ID NO:23. In some embodiments, a tetravalent antibody of the present disclosure comprises a monomer comprising two VH domains, each VH domain comprising a sequence having at least 90%, 91%, 92%, 93%, 94%, 95%, 96%, 97%, 98%, 99%, or 100% sequence identity to the amino acid sequence of SEQ ID NO:23. In some embodiments, the VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human PSGL-1 antibody comprising that sequence retains the ability to bind to human PSGL-1. In some embodiments, total of 1 to 10 amino acids have been substituted, inserted and/or deleted in SEQ ID NO:23.

In some embodiments, a tetravalent antibody of the present disclosure comprises one or more VH domains comprising a sequence having at least 90%, 91%, 92%, 93%, 94%, 95%, 96%, 97%, 98%, 99%, or 100% sequence identity to the amino acid sequence of SEQ ID NO:29. In some embodiments, a tetravalent antibody of the present disclosure comprises a monomer comprising two VH domains, each VH domain comprising a sequence having at least 90%, 91%, 92%, 93%, 94%, 95%, 96%, 97%, 98%, 99%, or 100% sequence identity to the amino acid sequence of SEQ ID NO:29. In some embodiments, the VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human PSGL-1 antibody comprising that sequence retains the ability to bind to human PSGL-1. In some embodiments, total of 1 to 10 amino acids have been substituted, inserted and/or deleted in SEQ ID NO:29.

In some embodiments, a tetravalent antibody of the present disclosure comprises one or more VL domains comprising one or more CDRs selected from (i) a CDR-L1 comprising the amino acid sequence of RSSQSIVHNDGNTYFE (SEQ ID NO:20); (ii) a CDR-L2 comprising the amino acid sequence of KVSNRFS (SEQ ID NO:21); and (iii) a CDR-L3 comprising the amino acid sequence of FQGSYVPLT (SEQ ID NO:22). In some embodiments, a tetravalent antibody of the present disclosure comprises one or more VL domains comprising (i) a CDR-L1 comprising the amino acid sequence of RSSQSIVHNDGNTYFE (SEQ ID NO:20); (ii) a CDR-L2 comprising the amino acid sequence of KVSNRFS (SEQ ID NO:21); and (iii) a CDR-L3 comprising the amino acid sequence of FQGSYVPLT (SEQ ID NO:22). In some embodiments, a tetravalent antibody of the present disclosure is a dimer of two monomers, each monomer comprising two VL domains, each VL domain comprising one or more CDRs selected from (i) a CDR-L1 comprising the amino acid sequence of RSSQSIVHNDGNTYFE (SEQ ID NO:20); (ii) a CDR-L2 comprising the amino acid sequence of KVSNRFS (SEQ ID NO:21); and (iii) a CDR-L3 comprising the amino acid sequence of FQGSYVPLT (SEQ ID NO:22). In some embodiments, a tetravalent antibody of the present disclosure is a dimer of two monomers, each monomer comprising two VL domains, each VL domain comprising (i) a CDR-L1 comprising the amino acid sequence of RSSQSIVHNDGNTYFE (SEQ ID NO:20); (ii) a CDR-L2 comprising the amino acid sequence of KVSNRFS (SEQ ID NO:21); and (iii) a CDR-L3 comprising the amino acid sequence of FQGSYVPLT (SEQ ID NO:22).

In some embodiments, a tetravalent antibody of the present disclosure comprises one or more VL domains comprising the amino acid sequence of SEQ ID NO:24. In some embodiments, a tetravalent antibody of the present disclosure comprises a monomer comprising two VL domains, each VL domain comprising the amino acid sequence of SEQ ID NO:24. In some embodiments, a tetravalent antibody of the present disclosure comprises one or more VL domains comprising the amino acid sequence of SEQ ID NO:30. In some embodiments, a tetravalent antibody of the present disclosure comprises a monomer comprising two VL domains, each VL domain comprising the amino acid sequence of SEQ ID NO:30.

In some embodiments, a tetravalent antibody of the present disclosure comprises one or more VL domains comprising a sequence having at least 90%, 91%, 92%, 93%, 94%, 95%, 96%, 97%, 98%, 99%, or 100% sequence identity to the amino acid sequence of SEQ ID NO:24. In some embodiments, a tetravalent antibody of the present disclosure comprises a monomer comprising two VL domains, each VL domain comprising a sequence having at least 90%, 91%, 92%, 93%, 94%, 95%, 96%, 97%, 98%, 99%, or 100% sequence identity to the amino acid sequence of SEQ ID NO:24. In some embodiments, the VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human PSGL-1 antibody comprising that sequence retains the ability to bind to human PSGL-1. In some embodiments, total of 1 to 10 amino acids have been substituted, inserted and/or deleted in SEQ ID NO:24.

In some embodiments, a tetravalent antibody of the present disclosure comprises one or more VL domains comprising a sequence having at least 90%, 91%, 92%, 93%, 94%, 95%, 96%, 97%, 98%, 99%, or 100% sequence identity to the amino acid sequence of SEQ ID NO:30. In some embodiments, a tetravalent antibody of the present disclosure comprises a monomer comprising two VL domains, each VL domain comprising a sequence having at least 90%, 91%, 92%, 93%, 94%, 95%, 96%, 97%, 98%, 99%, or 100% sequence identity to the amino acid sequence of SEQ ID NO:30. In some embodiments, the VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human PSGL-1 antibody comprising that sequence retains the ability to bind to human PSGL-1. In some embodiments, total of 1 to 10 amino acids have been substituted, inserted and/or deleted in SEQ ID NO:30.

In some embodiments, a tetravalent antibody of the present disclosure comprises a single-chain polypeptide comprising a sequence having at least 90%, 91%, 92%, 93%, 94%, 95%, 96%, 97%, 98%, 99%, or 100% sequence identity to the amino acid sequence of SEQ ID NOs:1, 3, or 5. In some embodiments, a tetravalent antibody of the present disclosure comprises a dimer of two monomers, each monomer comprising two single-chain polypeptides, each single-chain polypeptide comprising a sequence having at least 90%, 91%, 92%, 93%, 94%, 95%, 96%, 97%, 98%, 99%, or 100% sequence identity to the amino acid sequence of SEQ ID NOs:1, 3, or 5. In some embodiments, the single-chain polypeptide sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human PSGL-1 antibody comprising that sequence retains the ability to bind to human PSGL-1. In some embodiments, total of 1 to 10 amino acids have been substituted, inserted and/or deleted in SEQ ID NOs:1, 3, or 5. In some embodiments, a tetravalent antibody of the present disclosure comprises two single-chain polypeptides, each comprising the amino acid sequence of SEQ ID NOs:1, 3, or 5.

In some embodiments, a tetravalent antibody of the present disclosure comprises a single-chain polypeptide comprising a sequence having at least 90%, 91%, 92%, 93%, 94%, 95%, 96%, 97%, 98%, 99%, or 100% sequence identity to a single-chain polypeptide encoded by the polynucleotide sequence of SEQ ID NOs:2, 4, or 6. In some embodiments, a tetravalent antibody of the present disclosure comprises a dimer of two monomers, each monomer comprising two single-chain polypeptides, each single-chain polypeptide comprising a sequence having at least 90%, 91%, 92%, 93%, 94%, 95%, 96%, 97%, 98%, 99%, or 100% sequence identity to a single-chain polypeptide encoded by the polynucleotide sequence of SEQ ID NOs:2, 4, or 6. In some embodiments, the single-chain polypeptide sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human PSGL-1 antibody comprising that sequence retains the ability to bind to human PSGL-1. In some embodiments, total of 1 to 10 amino acids have been substituted, inserted and/or deleted in the single-chain polypeptide encoded by the polynucleotide sequence of SEQ ID NOs:2, 4, or 6. In some embodiments, a tetravalent antibody of the present disclosure comprises two single-chain polypeptides, each encoded by the polynucleotide sequence of SEQ ID NOs:2, 4, or 6.

In some embodiments, a tetravalent antibody of the present disclosure comprises a light chain polypeptide comprising a sequence having at least 90%, 91%, 92%, 93%, 94%, 95%, 96%, 97%, 98%, 99%, or 100% sequence identity to the amino acid sequence of SEQ ID NOs:7, 9, or 13. In some embodiments, a tetravalent antibody of the present disclosure comprises a dimer of two monomers, each monomer comprising a heavy chain and a light chain, and each light chain comprising a sequence having at least 90%, 91%, 92%, 93%, 94%, 95%, 96%, 97%, 98%, 99%, or 100% sequence identity to the amino acid sequence of SEQ ID NOs:7, 9, or 13. In some embodiments, the light chain polypeptide sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human PSGL-1 antibody comprising that sequence retains the ability to bind to human PSGL-1. In some embodiments, total of 1 to 10 amino acids have been substituted, inserted and/or deleted in SEQ ID NOs:7, 9, or 13. In some embodiments, a tetravalent antibody of the present disclosure comprises a dimer of two monomers, each monomer comprising a heavy chain and a light chain, and each light chain comprising the amino acid sequence of SEQ ID NOs:7, 9, or 13.

In some embodiments, a tetravalent antibody of the present disclosure comprises a light chain polypeptide comprising a sequence having at least 90%, 91%, 92%, 93%, 94%, 95%, 96%, 97%, 98%, 99%, or 100% sequence identity to a light chain polypeptide encoded by the polynucleotide sequence of SEQ ID NOs:8, 10, or 14. In some embodiments, a tetravalent antibody of the present disclosure comprises a dimer of two monomers, each monomer comprising a heavy chain and a light chain, and each light chain comprising a sequence having at least 90%, 91%, 92%, 93%, 94%, 95%, 96%, 97%, 98%, 99%, or 100% sequence identity to a light chain polypeptide encoded by the polynucleotide sequence of SEQ ID NOs:8, 10, or 14. In some embodiments, the light chain polypeptide sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human PSGL-1 antibody comprising that sequence retains the ability to bind to human PSGL-1. In some embodiments, total of 1 to 10 amino acids have been substituted, inserted and/or deleted in the light chain polypeptide encoded by the polynucleotide sequence of SEQ ID NOs:8, 10, or 14. In some embodiments, a tetravalent antibody of the present disclosure comprises a dimer of two monomers, each monomer comprising a heavy chain and a light chain, and each light chain comprising a light chain polypeptide encoded by the polynucleotide sequence of SEQ ID NOs:8, 10, or 14.

In some embodiments, a tetravalent antibody of the present disclosure comprises a heavy chain polypeptide comprising a sequence having at least 90%, 91%, 92%, 93%, 94%, 95%, 96%, 97%, 98%, 99%, or 100% sequence identity to the amino acid sequence of SEQ ID NOs:11 or 15. In some embodiments, a tetravalent antibody of the present disclosure comprises a dimer of two monomers, each monomer comprising a heavy chain and a light chain, and each heavy chain comprising a sequence having at least 90%, 91%, 92%, 93%, 94%, 95%, 96%, 97%, 98%, 99%, or 100% sequence identity to the amino acid sequence of SEQ ID NOs:11 or 15. In some embodiments, the heavy chain polypeptide sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human PSGL-1 antibody comprising that sequence retains the ability to bind to human PSGL-1. In some embodiments, total of 1 to 10 amino acids have been substituted, inserted and/or deleted in SEQ ID NOs:11 or 15. In some embodiments, a tetravalent antibody of the present disclosure comprises a dimer of two monomers, each monomer comprising a heavy chain and a light chain, and each heavy chain comprising the amino acid sequence of SEQ ID NOs:11 or 15.

In some embodiments, a tetravalent antibody of the present disclosure comprises a heavy chain polypeptide comprising a sequence having at least 90%, 91%, 92%, 93%, 94%, 95%, 96%, 97%, 98%, 99%, or 100% sequence identity to a heavy chain polypeptide encoded by the polynucleotide sequence of SEQ ID NOs:12 or 16. In some embodiments, a tetravalent antibody of the present disclosure comprises a dimer of two monomers, each monomer comprising a heavy chain and a light chain, and each heavy chain comprising a sequence having at least 90%, 91%, 92%, 93%, 94%, 95%, 96%, 97%, 98%, 99%, or 100% sequence identity to a heavy chain polypeptide encoded by the polynucleotide sequence of SEQ ID NOs:12 or 16. In some embodiments, the heavy chain polypeptide sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human PSGL-1 antibody comprising that sequence retains the ability to bind to human PSGL-1. In some embodiments, total of 1 to 10 amino acids have been substituted, inserted and/or deleted in the heavy chain polypeptide encoded by the polynucleotide sequence of SEQ ID NOs:12 or 16. In some embodiments, a tetravalent antibody of the present disclosure comprises a dimer of two monomers, each monomer comprising a heavy chain and a light chain, and each heavy chain comprising a light chain polypeptide encoded by the polynucleotide sequence of SEQ ID NOs: 12 or 16.

The present disclosure encompasses modifications to antibodies or polypeptide described herein, including functionally equivalent antibodies which do not significantly affect their properties and variants which have enhanced or decreased activity and/or affinity. Modification of polypeptides is routine practice in the art and need not be described in detail herein. Examples of modified polypeptides include polypeptides with conservative substitutions of amino acid residues, one or more deletions or additions of amino acids which do not significantly deleteriously change the functional activity, or use of chemical analogs.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to an epitope tag. Other insertional variants of the antibody molecule include the fusion to the N- or C-terminus of the antibody of an enzyme or a polypeptide which increases the serum half-life of the antibody.

Substitution variants have at least one amino acid residue in the antibody molecule removed and a different residue inserted in its place. The sites of greatest interest for substitutional mutagenesis include the hypervariable regions, but FR alterations are also contemplated. Conservative substitutions are shown in the table below under the heading of "conservative substitutions." If such substitutions result in a change in biological activity, then more substantial changes, denominated "exemplary substitutions" in the table below, or as further described below in reference to amino acid classes, may be introduced and the products screened.
Amino Acid Substitutions

| Original Residue | Conservative Substitutions | Exemplary Substitutions |
|---|---|---|
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:
 (1) Non-polar: Norleucine, Met, Ala, Val, Leu, Ile;
 (2) Polar without charge: Cys, Ser, Thr, Asn, Gln;
 (3) Acidic (negatively charged): Asp, Glu;
 (4) Basic (positively charged): Lys, Arg;
 (5) Residues that influence chain orientation: Gly, Pro; and
 (6) Aromatic: Trp, Tyr, Phe, His Non-conservative substitutions are made by exchanging a member of one of these classes for another class.

Any cysteine residue not involved in maintaining the proper conformation of the antibody also may be substituted, generally with serine, to improve the oxidative stability of the molecule and prevent aberrant cross-linking. Conversely, cysteine bond(s) may be added to the antibody to improve its stability, particularly where the antibody is an antibody fragment such as an Fv fragment. Exemplary cysteine mutations are described herein (e.g., the G44C VH domain mutation of SEQ ID NO:29, or the Q100C VL domain mutation of SEQ ID NO:30).

In some embodiments, a tetravalent antibody of the present disclosure comprises an antibody Fc domain. In some embodiments, the antibody Fc domain is a human Fc domain. In certain embodiments, the antibody Fc domain is a human IgG4 Fc domain.

In some embodiments, one or more amino acid residues in the heavy chain constant region and/or the light chain constant region of the antibody are modified. For example, amino acid residues of antibodies described in the Examples may be modified. In some embodiments, the Fc region of antibodies is modified to enhance or reduce ADCC and/or CDC activities of the antibodies. See Shields et al., J. Biol. Chem. 276:6591-6604 (2001); Presta et al., Biochem. Soc. Trans. 30:487-490 (2002).

In some embodiments, the Fc region of antibodies is modified to enhance dimer formation and/or stability, or to reduce dimer heterogeneity (e.g., shuffling). It has been demonstrated that a Serine to Proline mutation at position 241 using Kabat numbering (Kabat et al. 1991, Sequences of Proteins of Immunological Interest, Fifth Edition, U.S. Department of Health and Human Services, NIH Publication No. 91-3242) or at position 228 using the EU index (Edelman et al, 1969, Proc. Natl. Acad. Sci. USA, 63(1): 78-85) in the hinge region of human IgG4 results in considerable reduction of intra-chain disulfide bond formation, resulting in the reduction of IgG4 "half-antibody" molecules and reduced heterogeneity/shuffling of IgG4 molecules (Bloom et al. 1997, Protein Sci, 6:407-415; Angal et al, 1993, Molecular Immunology, 30(1): 105-108)). There are also published reports that this hinge mutation may decrease IgG4 shuffling and increase the half-life of the IgG4 molecules in vivo (Labrijn, et al, 2009, Nat Biotechnol 27:767-771; Stubenrauch, et al, 2010, Drug Metab Dispos 38:84-91). Van der Neut Kolfschoten et al, reported that the $C_H3$ domain of IgG4 and not the core hinge is predominantly involved in the Fab arm exchange reaction (see Van der Neut Kolfschoten et al, 2007, Science, 317: 1554-1557 ("Van der Neut Kolfschoten") at page 1555, col. 2). Van der Neut Kolfschaten reported that exchanging the $C_H3$ domain of IgG1 for the $C_H3$ domain of IgG4 activated Fab arm exchange for the IgG1, while exchanging the $C_H3$ domain of IgG4 abrogated Fab arm exchange for the IgG4 (see, p. 1555 and FIG. 2D).

In a specific embodiment, provided herein are tetravalent antibodies, that specifically bind to PSGL-1, and that contain one or more amino acid substitutions in the IgG4 hinge region, wherein said antibody or antigen-binding fragment thereof retains specific binding to said PSGL-1 and wherein IgG4 shuffling is reduced relative to an antibody comprising an IgG4 hinge region not comprising said one or more amino acid substitutions. In a specific embodiment, the IgG4 hinge region only comprises a single amino acid substitution. An example of a "human IgG4 hinge region," is the region on the heavy chain of an IgG4 antibody between the $C_H1$ and $C_H2$ domains, as set forth in Angal et al., 1993, Molecular Immunology, 30(1): 105-108.

In a specific embodiment, a reduction in IgG4 shuffling is determined by detecting of a lower amount of half antibody molecules or of arm exchange produced from an antibody described herein which contains one or more amino acid substitutions in the hinge region, as compared to the amount of half antibody molecules or of arm exchange produced from an IgG4 molecule containing an IgG4 hinge region not comprising said one or more amino acid substitutions. Any assay well-known in the art can be used to detect half antibody production and bispecific antibody molecules. See, e.g., Van der Neut Kolfschoten et al, 2007, Science, 317: 1554-1557, for examples of assays to detect production of bispecific antibodies.

In a specific embodiment, provided herein are tetravalent antibodies that specifically bind to PSGL-1 and include a human IgG4 Fc domain comprising a Serine to Proline amino acid substitution at amino acid position 228 of the heavy chain numbered according to the EU index (also known as position 241 using Kabat numbering).

Modifications also include glycosylated and nonglycosylated polypeptides, as well as polypeptides with other post-translational modifications, such as, for example, glycosylation with different sugars, acetylation, and phosphorylation. Antibodies are glycosylated at conserved positions in their constant regions (Jefferis and Lund, 1997, Chem. Immunol. 65:111-128; Wright and Morrison, 1997, TibTECH 15:26-32). The oligosaccharide side chains of the immunoglobulins affect the protein's function (Boyd et al., 1996, Mol. Immunol. 32:1311-1318; Wittwe and Howard, 1990, Biochem. 29:4175-4180) and the intramolecular interaction between portions of the glycoprotein, which can affect the conformation and presented three-dimensional surface of the glycoprotein (Hefferis and Lund, supra; Wyss and Wagner, 1996, Current Opin. Biotech. 7:409-416). Oligosaccharides may also serve to target a given glycoprotein to certain molecules based upon specific recognition structures. Glycosylation of antibodies has also been reported to affect antibody-dependent cellular cytotoxicity (ADCC). In particular, CHO cells with tetracycline-regulated expression of β(1,4)-N-acetylglucosaminyltransferase III (GnTIII), a glycosyltransferase catalyzing formation of bisecting GlcNAc, was reported to have improved ADCC activity (Umana et al., 1999, Mature Biotech. 17:176-180).

Glycosylation of antibodies is typically either N-linked or O-linked. N-linked refers to the attachment of the carbohydrate moiety to the side chain of an asparagine residue. The tripeptide sequences asparagine-X-serine, asparagine-X-threonine, and asparagine-X-cysteine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

The glycosylation pattern of antibodies may also be altered without altering the underlying nucleotide sequence. Glycosylation largely depends on the host cell used to express the antibody. Since the cell type used for expression of recombinant glycoproteins, e.g., antibodies, as potential therapeutics is rarely the native cell, variations in the glycosylation pattern of the antibodies can be expected (see, e.g., Hse et al., 1997, J. Biol. Chem. 272:9062-9070).

In addition to the choice of host cells, factors that affect glycosylation during recombinant production of antibodies include growth mode, media formulation, culture density, oxygenation, pH, purification schemes, and the like. Various methods have been proposed to alter the glycosylation pattern achieved in a particular host organism including introducing or overexpressing certain enzymes involved in oligosaccharide production (U.S. Pat. Nos. 5,047,335; 5,510,261; and 5,278,299). Glycosylation, or certain types of glycosylation, can be enzymatically removed from the glycoprotein, for example using endoglycosidase H (Endo H), N-glycosidase F, endoglycosidase F1, endoglycosidase F2, or endoglycosidase F3. In addition, the recombinant host cell can be genetically engineered to be defective in processing certain types of polysaccharides. These and similar techniques are well known in the art.

In some embodiments, an antibody of the present disclosure is modified using coupling techniques known in the art, including, but not limited to, enzymatic means, oxidative substitution, and chelation. Modifications can be used, for example, for attachment of labels for immunoassay.

The tetravalent antibody or polypeptide of the present disclosure may be conjugated (for example, linked) to an agent, such as a therapeutic agent or a label. Examples of therapeutic agents are radioactive moieties, cytotoxins, and chemotherapeutic molecules.

The tetravalent antibody (or polypeptide) of the present disclosure may be linked to a label such as a fluorescent molecule, a radioactive molecule, an enzyme, or any other labels known in the art. As used herein, the term "label" refers to any molecule that can be detected. In a certain embodiment, an antibody may be labeled by incorporation of a radiolabeled amino acid. In a certain embodiment, biotin moieties that can be detected by marked avidin (e.g., streptavidin containing a fluorescent marker or enzymatic activity that can be detected by optical or colorimetric methods) may be attached to the antibody. In certain embodiments, a label may be incorporated into or attached to another reagent which in turn binds to the antibody of interest. For example, a label may be incorporated into or attached to an antibody that in turn specifically binds the antibody of interest. In certain embodiments, the label or marker can also be therapeutic. Various methods of labeling polypeptides and glycoproteins are known in the art and may be used. Certain general classes of labels include, but are not limited to, enzymatic, fluorescent, chemiluminescent, and radioactive labels. Examples of labels for polypeptides include, but are not limited to, the following: radioisotopes or radionucleoides (e.g., $^{3}$H, $^{14}$C, $^{15}$N, $^{35}$S, $^{90}$Y, $^{99}$Tc, $^{111}$In, $^{125}$I, or $^{131}$I) fluorescent labels (e.g., fluorescein isothocyanate (FITC), rhodamine, lanthanide phosphors, or phycoerythrin (PE)), enzymatic labels (e.g., horseradish peroxidase, β-galactosidase, luciferase, alkaline phosphatase, glucose oxidase, glucose-6-phosphate dehydrogenase, alcohol dehydrogenase, malate dehydrogenase, penicillinase, or luciferase), chemiluminescent, biotinyl groups, predetermined polypeptide epitopes recognized by a secondary reporter (e.g., leucine zipper pair sequences, binding sites for secondary antibodies, metal binding domains, or epitope tags). In certain embodiments, labels are attached by spacer arms of various lengths to reduce potential steric hindrance.

Based on the description herein, a tetravalent antibody of the present disclosure may be tested according to a variety of in vitro and in vivo assays known in the art. Such assays may include, e.g., binding assays directed to the ability of a tetravalent antibody or fragment thereof to bind an epitope or polypeptide of interest (e.g., human PSGL-1 or an epitope thereof), or functional assays directed to one or more functional properties of a tetravalent antibody or fragment thereof.

In some embodiments, a tetravalent antibody of the present disclosure may be tested for binding activity against human PSGL-1. In some embodiments, binding of a tetravalent antibody to human PSGL-1 or an epitope thereof may be tested in an in vitro binding assay. A variety of binding assays are known in the art. Such binding assays may be cell-based assays (e.g., testing the ability of a tetravalent antibody to bind a cell expressing human PSGL-1 or an epitope thereof), or they may be polypeptide-based (e.g., testing the ability of a tetravalent antibody to bind human PSGL-1 or an epitope thereof). In some embodiments, a tetravalent antibody of the present disclosure is tested for binding to a cell expressing human PSGL-1 (e.g., an Sp2 cell, as exemplified infra) by flow cytometry, FRET, histochemical assays, and the like. Other suitable binding assays may include without limitation equilibrium methods (e.g., enzyme-linked immunoabsorbent assay (ELISA), radioimmunoassay (RIA), Biacore™ analysis, indirect binding assay, competitive inhibition assay, fluorescence resonance energy transfer (FRET), immunoprecipitation, gel electrophoresis and chromatography (e.g., gel filtration).

In some embodiments, a tetravalent antibody of the present disclosure may be tested for one or more functional assays for PSGL-1 function. In some embodiments, a tetravalent antibody of the present disclosure may be tested for induction of apoptosis in cell(s) expressing human PSGL-1. In some embodiments, a tetravalent antibody of the present disclosure displays enhanced induction of apoptosis in a target cell (e.g., a cell expressing human PSGL-1 or an epitope thereof) as compared to a conventional (e.g., bivalent) antibody having one or more VH or VL domains in common with the tetravalent antibody (e.g., a parental antibody). As demonstrated herein, tetravalent antibodies of the present disclosure displayed greater potency in inducing apoptosis in target cells than parental antibodies having a common VH and/or VL domain. Apoptosis assays are described in the art and can be readily carried out by one of skill in the art (see, e.g., Muppidi, J., Porter, M. and Siegel, R. M. 2004. Measurement of Apoptosis and Other Forms of Cell Death. Current Protocols in Immunology. 59:3.17.1-3.17.36). Selected assays for detecting apoptosis (e.g., Annexin V or propidium iodide staining) are exemplified supra. The term "induce" or "inducing" means initiation of or an increase of apoptosis above a control level. Apoptosis of activated T cells can be induced by about 10%, about 20%, about 30%, about 40%, about 50%, about 60%, about 70%, about 80%, about 90%, about 100%, about 125%, about 150% or more compared to a control (e.g. Apoptosis of activated T cells in the absence of the antibodies describe herein or in the presence of a non-specific antibody).

T cells and T cell lines which are appropriate for use in the assays described herein relating to PSGL-1 activity are readily available (e.g., ARR, DU.528, Jurkat, H-SB2, RPMI 8402, CML-T1, Karpas 45, KE-37/SKW-3, SUP-T1, SUP-T3, MOLT 3/4, P12-Ichikawa, PF-382, CCRF-CEM, HPB-ALL, K-T1, TALL-1, MOLT 16/17, TALL-104, DND-41, Loucy, MOLT 13, Peer/Bel3, HUT 78/H9, HUT 102, MT-1, DEL, JB6, Karpas 299, SU-DHL1, 12H5, 3D054.8, 3D011.10, 8D051.15, or 3D018.3) or can be readily identified using methods known in the art (see, e.g., Thornton, A. M. 2003. Fractionation of T and B Cells Using Magnetic Beads. Current Protocols in Immunology. 55:3.5A. 1-3.5A. i1 Hathcock, K. 2001. T Cell Enrichment by Cytotoxic Elimination of B Cells and Accessory Cells. Current Protocols in Immunology. 00:3.3.1-3.3.5., Horgan, K., Shaw, S. and Boirivant, M. 2009. Immunomagnetic Purification of T Cell Subpopulations. Current Protocols in Immunology. 85:7.4.1-7.4.9., and Kanof, M. E. 2001. Purification of T Cell Subpopulations. Current Protocols in Immunology. 00:7.3.1-7.3.5). In particular embodiments, cells or cell lines for use in cell proliferation assays can express PSGL-1, endogenously or recombinantly. Cells or cell lines for use in cell viability assays can express PSGL-1, endogenously or recombinantly, and exert changes in cell viability in response to PSGL-1 ligand or anti-PSGL-1 antibody binding. Cells or cell lines for use in apoptosis assays can express PSGL-1, endogenously or recombinantly, and exert changes in apoptosis in response to PSGL-1 ligand or anti-PSGL-1 antibody binding. Preferably the cells or cell lines are human (e.g. ARR, DU.528, Jurkat, H-SB2, RPMI 8402, CML-T1, Karpas 45, KE-37/SKW-3, SUP-T1, SUP-T3, MOLT 3/4, P12-Ichikawa, PF-382, CCRF-CEM, HPB-ALL, K-T1, TALL-1, MOLT 16/17, TALL-104, DND-41, Loucy, MOLT 13, Peer/Bel3, HUT 78/H9, HUT 102, MT-1, DEL, JB6, Karpas 299, or SU-DHL1).

In some embodiments, a tetravalent antibody of the present disclosure may be tested for inhibition of delayed type hypersensitivity (DTH). In some embodiments, a tetravalent antibody of the present disclosure displays enhanced inhibition of DTH (e.g., in a trans vivo animal model) as compared to a conventional (e.g., bivalent) antibody having one or more VH or VL domains in common with the tetravalent antibody (e.g., a parental antibody). As demonstrated herein, tetravalent antibodies of the present disclosure displayed greater potency in inhibiting DTH in a trans vivo mouse footpad swelling model than parental antibodies having a common VH and/or VL domain. DTH assays are described in the art and exemplified infra and can be readily carried out by one of skill in the art. In some embodiments, a tetravalent antibody of the present disclosure may display a potency of DTH inhibition that may be increased by about 10%, about 20%, about 30%, about 40%, about 50%, about 60%, about 70%, about 80%, about 90%, about 100%, about 125%, about 150%, about 200%, about 300%, about 400%, about 500%, about 600%, or more compared to a control (e.g. inhibition of DTH by a conventional or bivalent antibody, such as the parental antibody).

III. Polynucleotides, Vectors, Host Cells, and Antibody Production

The present disclosure also provides polynucleotides comprising a polynucleotide encoding any of the tetravalent antibodies and/or polypeptides described herein. In some embodiments, the polypeptides comprise the sequences of light chain and heavy chain variable regions. In some embodiments, the polynucleotide is an isolated polynucleotide (e.g., isolated from a host cell or from one or more different polynucleotides).

Provided herein are polynucleotides encoding any of the tetravalent antibodies or polypeptide constituents (e.g., monomers such as single-chain polypeptides, antibody heavy chains, and/or antibody light chains) described herein. In some embodiments, a polynucleotide of the present disclosure encodes a polypeptide sequence selected from SEQ ID NOs:1, 3, 5, 7, 9, 11, 13, 15, and 17-31. In some embodiments, a polynucleotide of the present disclosure comprises a polynucleotide sequence selected from SEQ ID NOs:2, 4, 6, 8, 10, 12, 14, and 16. In some embodiments, a polynucleotide of the present disclosure comprises one or more introns. In other embodiments, a polynucleotide of the present disclosure does not comprise an intron, e.g., a cDNA or processed mRNA sequence.

It is appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Thus, polynucleotides that vary due to differences in codon usage are specifically contemplated by the present disclosure. Further, alleles of the genes comprising the polynucleotide sequences provided herein are within the scope of the present disclosure. Alleles are endogenous genes that are altered as a result of one or more mutations, such as deletions, additions, and/or substitutions of nucleotides. The resulting mRNA and protein can, but need not, have an altered structure or function. Alleles can be identified using standard techniques (such as hybridization, amplification, and/or database sequence comparison).

Also provided herein are polynucleotides that are optimized, e.g., by codon/RNA optimization, replacement with heterologous signal sequences, and elimination of mRNA instability elements. Methods to generate optimized nucleic acids encoding a tetravalent antibody or polypeptide thereof for recombinant expression by introducing codon changes and/or eliminating inhibitory regions in the mRNA can be carried out by adapting the optimization methods described in, e.g., U.S. Pat. Nos. 5,965,726; 6,174,666; 6,291,664; 6,414,132; and 6,794,498, accordingly. For example, potential splice sites and instability elements (e.g., A/T or A/U rich elements) within the RNA can be mutated without altering the amino acids encoded by the nucleic acid sequences to increase stability of the RNA for recombinant expression. The alterations utilize the degeneracy of the genetic code, e.g., using an alternative codon for an identical amino acid. In some embodiments, it can be desirable to alter one or more codons to encode a conservative mutation, e.g., a similar amino acid with similar chemical structure and properties and/or function as the original amino acid. Such methods can increase expression of an anti-PSGL-1 tetravalent antibody or polypeptide thereof relative to the expression of an anti-PSGL-1 tetravalent antibody or polypeptide thereof encoded by polynucleotides that have not been optimized. Furthermore, the polynucleotide sequences can be designed to match the preferred codon usage in the host cell, e.g. E. coli codon usage or CHO codon usage.

An optimized polynucleotide sequence encoding a tetravalent antibody or polypeptide thereof described herein can hybridize to an unoptimized polynucleotide sequence encoding a tetravalent antibody or polypeptide thereof described herein. In specific embodiments, an optimized nucleotide sequence encoding a tetravalent antibody or polypeptide thereof described herein hybridizes under high stringency conditions to an unoptimized polynucleotide sequence encoding a tetravalent antibody or polypeptide thereof described herein. In a specific embodiment, an optimized nucleotide sequence encoding a tetravalent antibody or polypeptide thereof described herein hybridizes under high stringency, intermediate or lower stringency hybridization conditions to an unoptimized nucleotide sequence encoding a tetravalent antibody or polypeptide thereof described herein. Information regarding hybridization conditions have been described, see, e.g., U.S. Patent Application Publication No. US 2005/0048549 (e.g., paragraphs 72-73), which is incorporated herein by reference in its entirety.

The polynucleotides of the present disclosure can be obtained using chemical synthesis, recombinant methods, or PCR. Methods of chemical polynucleotide synthesis are well known in the art and need not be described in detail herein. One of skill in the art can use the sequences provided herein and a commercial DNA synthesizer to produce a desired DNA sequence.

For preparing polynucleotides using recombinant methods, a polynucleotide comprising a desired sequence can be inserted into a suitable vector, and the vector in turn can be introduced into a suitable host cell for replication and amplification, as further discussed herein. Polynucleotides can be inserted into host cells by any means known in the art. Cells are transformed by introducing an exogenous polynucleotide by direct uptake, endocytosis, transfection, F-mating, or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al. (1989).

Alternatively, PCR allows reproduction of DNA sequences. PCR technology is well known in the art and is described in U.S. Pat. Nos. 4,683,195; 4,800,159; 4,754,065; and 4,683,202, as well as PCR: The Polymerase Chain Reaction, Mullis et al. eds., Birkauswer Press, Boston (1994).

The present disclosure also provides vectors (e.g., cloning vectors or expression vectors) comprising a nucleic acid sequence encoding any of the polypeptides (including antibodies) described herein. Suitable cloning vectors can be constructed according to standard techniques or may be selected from a large number of cloning vectors available in the art. While the cloning vector selected may vary according to the host cell intended to be used, useful cloning vectors generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

Expression vectors generally are replicable polynucleotide constructs that contain a polynucleotide according to the present disclosure. The expression vector may replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; and suitable transcriptional controlling elements (such as promoters, enhancers, or terminator). For expression (i.e., translation), one or more translational controlling elements are also usually required, such as ribosome binding sites, translation initiation sites, or stop codons.

Methods of making antibodies and polypeptides derived from the antibodies are known in the art and are disclosed herein. Well-established methods may be used to identify anti-PSGL antibodies (e.g., antibodies that specifically bind to human PSGL-1), from which variable domains (e.g., VH and/or VL domains) may be used in the tetravalent antibodies of the present disclosure. Exemplary anti-human PSGL-1 antibodies, as well as methods for screening, producing, and purifying such antibodies, are described in International Application Pub. No. WO 2012/174001.

Additional anti-human PSGL-1 antibodies may be identified using methods known in the art, such as those described in International Application Pub. No. WO 2012/174001 and supra. For example, the monoclonal antibodies can be prepared using hybridoma technology, such as those described by Kohler and Milstein (1975), *Nature*, 256:495. In a hybridoma method, a mouse, a hamster, or other appropriate host animal, is typically immunized with an immunizing agent (e.g., a cell expressing human PSGL-1 or a fragment thereof) to elicit lymphocytes that produce or are capable of producing antibodies that specifically bind to the immunizing agent. Alternatively, the lymphocytes may be immunized in vitro. The lymphocytes are then fused with an immortalized cell line using a suitable fusing agent, such as polyethylene glycol, to form a hybridoma cell (Goding, Monoclonal Antibodies: Principles and Practice, Academic Press, (1986) pp. 59-103I). Immortalized cell lines are usually transformed mammalian cells, particularly myeloma cells of rodent, rabbit, bovine, or human origin. Usually, rat or mouse myeloma cell lines are employed. The hybridoma cells may be cultured in a suitable culture medium that desirably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically includes hypoxanthine, aminopterin, and thymidine ("HAT medium"), which substances prevent the growth of HGPRT-deficient cells.

Desired immortalized cell lines are those that fuse efficiently, support stable high level expression of antibody by the selected antibody-producing cells, and are sensitive to a medium such as HAT medium. More desirable immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies (Kozbor, J. Immunol. (1984), 133:3001; Brodeur et al., Monoclonal Antibody Production Techniques and Applications, Marcel Dekker, Inc., New York, (1987) pp. 51-63).

The culture medium in which the hybridoma cells are cultured can then be assayed for the presence of monoclonal antibodies. The antibody may be screened for having specific binding to an ORP150 polypeptide (such as binding to an epitope in an extracellular domain of the ORP150 polypeptide) obtained from or expressed on the cell surface of plasmacytoma, multiple myeloma, colorectal, gastric, or esophageal cancer or tumor cells. Cancer cells or an ORP150 polypeptide (or a fragment thereof containing an extracellular domain of an ORP150 polypeptide) may be used for screening. For example, RPMI8226, U266, NCI-H929, L363, Colo205, DLD-1, HT29, SNU-1, Kato-III, or CE146T cells may be used for screening. A polypeptide comprising amino acids 673-800, 701-800, 673-752, or 723-732 of SEQ ID NO:17 may also be used for screening.

In some embodiments, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard (1980), *Anal. Biochem.*, 107:220.

After the desired hybridoma cells are identified, the clones may be subcloned by limiting dilution procedures and grown by standard methods (Goding, supra). Suitable culture media for this purpose include, for example, Dulbecco's Modified Eagle's Medium or RPMI-1640 medium. Alternatively, the hybridoma cells may be grown in vivo as ascites in a mammal.

The monoclonal antibodies can be generated by culturing the hybridoma cells, and the antibodies secreted by the hybridoma cells may further be isolated or purified. Antibodies may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The tetravalent antibodies or polypeptides of the present disclosure may be generated by screening a library of antibodies or polypeptides to select antibodies or polypeptides that bind to human PSGL-1, e.g., expressed on the cell surface of a cell. Antibody phage display libraries known in the art may be used. In some embodiments, the antibodies in the library (e.g., displayed on phage) are single-chain Fv (scFv) fragments or Fab fragment. In some embodiments, the antibodies in the library (e.g., displayed on phage) are single-domain antibodies. For example, a single-domain antibody may comprise all or a portion of the heavy chain variable domain or all or a portion of the light chain variable domain of an antibody. In some embodiments, the antibodies in the library are human antibodies. The antibodies identified may further be tested for their capabilities to induce cell death (e.g., apoptosis) and/or bind human PSGL-1 using methods known in the art and described herein.

The tetravalent antibodies of the present disclosure can be made by recombinant DNA methods, such as those described in U.S. Pat. Nos. 4,816,567 and 6,331,415. For example, DNA encoding the variable or constant region of any of the tetravalent antibodies of the present disclosure (or single, heavy, or light chain polypeptides that are constituents thereof) can be readily isolated and sequenced using conventional procedures (e.g., by using oligonucleotide probes that are capable of binding specifically to genes encoding the heavy and light chains of murine antibodies). The hybridoma cells of the present disclosure serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein to synthesize monoclonal antibodies in the recombinant host cells. The DNA also can be modified, for example, by substituting the coding sequence for human heavy and light chain constant domains in place of the homologous murine sequences (U.S. Pat. No. 4,816,567) or by covalently joining to the immunoglobulin coding sequence all or part of the coding sequence for a non-immunoglobulin polypeptide. Such a non-immunoglobulin polypeptide can be substituted for the constant domains of an antibody of the present disclosure, or can be substituted for the variable domains of one antigen-combining site of an antibody of the present disclosure to create a chimeric bivalent antibody.

In some embodiments, the tetravalent antibodies of the present disclosure are expressed from two expression vectors. For example, each expression vector may express one monomer of a dimer of the present disclosure (e.g., a single-chain polypeptide or antibody heavy or light chain polypeptide). Alternatively, both monomers of a dimer of the present disclosure are expressed from a single expression vector.

Normally the expression vector has transcriptional and translational regulatory sequences which are derived from a species compatible with a host cell. In addition, the vector ordinarily carries a specific gene(s) which is (are) capable of providing phenotypic selection in transformed cells.

A wide variety of recombinant host-vector expression systems for eukaryotic cells are known and can be used in the present disclosure. For example, *Saccharomyces cerevi*- siae, or common baker's yeast, is the most commonly used among eukaryotic microorganisms, although a number of other strains, such as *Pichia pastoris*, are available. Cell lines derived from multicellular organisms such as Sp2/0 or Chinese Hamster Ovary (CHO), which are available from the ATCC, may also be used as hosts. Typical vector plasmids suitable for eukaryotic cell transformations are, for example, pSV2neo and pSV2gpt (ATCC), pSVL and pSVK3 (Pharmacia), and pBPV-1/pML2d (International Biotechnology, Inc.).

The eukaryotic host cells useful in the present disclosure are, for example, hybridoma, myeloma, plasmacytoma, or lymphoma cells. However, other eukaryotic host cells may be suitably utilized provided the mammalian host cells are capable of recognizing transcriptional and translational DNA sequences for expression of the proteins; processing the leader peptide by cleavage of the leader sequence and secretion of the proteins; and providing post-translational modifications of the proteins, e.g., glycosylation.

Accordingly, the present disclosure provides host cells (e.g., eukaryotic host cells) which are transformed by recombinant expression vectors comprising DNA constructs disclosed herein and which are capable of expressing the tetravalent antibodies or polypeptides of the present disclosure. In some embodiments, the transformed host cells of the present disclosure comprise at least one DNA construct comprising a polynucleotide of the present disclosure, or a polynucleotide expressing a monomer, dimer, or tetravalent antibody of the present disclosure, and transcriptional and translational regulatory sequences which are positioned in relation to the coding DNA sequences to direct expression of antibodies or polypeptides.

Any host cells capable of over-expressing heterologous DNAs can be used for the purpose of isolating the genes encoding the antibody, polypeptide, or protein of interest. Non-limiting examples of mammalian host cells include but not limited to COS, HeLa, and CHO cells. See also PCT Publication No. WO 87/04462. Suitable non-mammalian host cells include prokaryotes (such as *E. coli* or *B. subtillis*) and yeast (such as *S. cerevisae, S. pombe*, or *K. lactis*).

The host cells used in the present disclosure may be transformed in a variety of ways by standard transfection procedures well known in the art. Among the standard transfection procedures which may be used are electroporation techniques, protoplast fusion and calcium-phosphate precipitation techniques. Such techniques are generally described by F. Toneguzzo et al. (1986), *Mol. Cell. Biol.*, 6:703-706; G. Chu et al., *Nucleic Acid Res*. (1987), 15:1311-1325; D. Rice et al., *Proc. Natl. Acad. Sci. USA* (1979), 79:7862-7865; and V. Oi et al., *Proc. Natl. Acad. Sci. USA* (1983), 80:825-829. The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides often depends on features of the host cell.

In the case of two expression vectors, the two expression vectors can be transferred into a host cell one by one separately or together (co-transfer or co-transfect).

The present disclosure also provides a method for producing the antibodies or polypeptides that comprises culturing a host cell comprising an expression vector(s) encoding the antibodies or the polypeptides, and recovering the antibodies or polypeptides from the culture by ways well known to one skilled in the art.

Furthermore, the desired antibodies can be produced in a transgenic animal. A suitable transgenic animal can be obtained according to standard methods which include micro-injecting into eggs the appropriate expression vectors, transferring the eggs into pseudo-pregnant females, and selecting a descendant expressing the desired antibody.

The present disclosure also provides chimeric tetravalent antibodies that specifically bind human PSGL-1. For example, the variable and constant regions of the tetravalent antibody are from separate species. In some embodiments, the variable regions of both heavy chain and light chain are from the murine antibodies described herein. The chimeric antibody of the present disclosure can be prepared by techniques well-established in the art. See for example, U.S. Pat. Nos. 6,808,901; 6,652,852; 6,329,508; 6,120,767; and 5,677,427, each of which is hereby incorporated by reference. In general, the chimeric antibody can be prepared by obtaining cDNAs encoding the heavy and light chain variable regions of the antibodies, inserting the cDNAs into an expression vector, which upon being introduced into eukaryotic host cells, expresses the chimeric antibody of the present disclosure. Desirably, the expression vector carries a functionally complete constant heavy or light chain sequence so that any variable heavy or light chain sequence can be easily inserted into the expression vector.

The present disclosure provides a humanized tetravalent antibody that specifically binds to human PSGL-1. The humanized antibody is typically a human antibody in which residues from CDRs are replaced with residues from CDRs of a non-human species such as mouse, rat, or rabbit having the desired specificity, affinity and capacity. In some instances, Fv framework residues of the human antibody are replaced by corresponding non-human residues.

There are four general steps to humanize a monoclonal antibody. These are: (1) determining the nucleotide and predicted amino acid sequence of the starting antibody light and heavy variable domains, (2) designing the humanized antibody, i.e., deciding which antibody framework region to use during the humanizing process, (3) the actual humanizing methodologies/techniques, and (4) the transfection and expression of the humanized antibody. See, for example, U.S. Pat. Nos. 4,816,567; 5,807,715; 5,866,692; 6,331,415; 5,530,101; 5,693,761; 5,693,762; 5,585,089; 6,180,370; and 6,548,640. For example, the constant region may be engineered to more resemble human constant regions to avoid immune response if the antibody is used in clinical trials and treatments in humans. See, for example, U.S. Pat. Nos. 5,997,867 and 5,866,692.

It is important that antibodies be humanized with retention of high affinity for the antigen and other favorable biological properties. To achieve this goal, humanized antibodies can be prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding. The humanized antibodies may also contain modifications in the hinge region to improve one or more characteristics of the antibody.

In another alternative, antibodies may be screened and made recombinantly by phage display technology. See, for example, U.S. Pat. Nos. 5,565,332; 5,580,717; 5,733,743 and 6,265,150; and Winter et al., *Annu. Rev. Immunol.* 12:433-455 (1994). Alternatively, the phage display technology (McCafferty et al., *Nature* 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats; for review see, e.g., Johnson, Kevin S. and Chiswell, David J., *Current Opinion in Structural Biology* 3, 564-571 (1993). Several sources of V-gene segments can be used for phage display. Clackson et al., *Nature* 352:624-628 (1991) isolated a diverse array of anti-oxazolone antibodies from a small random combinatorial library of V genes derived from the spleens of immunized mice. A repertoire of V genes from unimmunized human donors can be constructed, and antibodies to a diverse array of antigens (including self-antigens) can be isolated essentially following the techniques described by Mark et al., *J. Mol. Biol.* 222:581-597 (1991), or Griffith et al., *EMBO J.* 12:725-734 (1993). In a natural immune response, antibody genes accumulate mutations at a high rate (somatic hypermutation). Some of the changes introduced will confer higher affinity, and B-cells displaying high-affinity surface immunoglobulin are preferentially replicated and differentiated during subsequent antigen challenge. This natural process can be mimicked by employing the technique known as "chain shuffling." Marks et al., *Bio/Technol.* 10:779-783 (1992)). In this method, the affinity of "primary" human antibodies obtained by phage display can be improved by sequentially replacing the heavy and light chain V region genes with repertoires of naturally occurring variants (repertoires) of V domain genes obtained from unimmunized donors. This technique allows the production of antibodies and antibody fragments with affinities in the pM-nM range. A strategy for making very large phage antibody repertoires (also known as "the mother-of-all libraries") has been described by Waterhouse et al., *Nucl. Acids Res.* 21:2265-2266 (1993). Gene shuffling can also be used to derive human antibodies from rodent antibodies, where the human antibody has similar affinities and specificities to the starting rodent antibody. According to this method, which is also referred to as "epitope imprinting," the heavy or light chain V domain gene of rodent antibodies obtained by phage display technique is replaced with a repertoire of human V domain genes, creating rodent-human chimeras. Selection on antigen results in isolation of human variable regions capable of restoring a functional antigen-binding site, i.e., the epitope governs (imprints) the choice of partner. When the process is repeated in order to replace the remaining rodent V domain, a human antibody is obtained (see PCT Publication No. WO 93/06213, published Apr. 1, 1993). Unlike traditional humanization of rodent antibodies by CDR grafting, this technique provides completely human antibodies, which have no framework or CDR residues of rodent origin. It is apparent that although the above discussion pertains to humanized antibodies, the general principles discussed are applicable to customizing antibodies for use, for example, in dogs, cats, primates, equines, and bovines.

In certain embodiments, the antibody is a fully human antibody. Non-human antibodies that specifically bind an antigen can be used to produce a fully human antibody that binds to that antigen. For example, the skilled artisan can employ a chain swapping technique, in which the heavy chain of a non-human antibody is co-expressed with an expression library expressing different human light chains. The resulting hybrid antibodies, containing one human light chain and one non-human heavy chain, are then screened for antigen binding. The light chains that participate in antigen binding are then co-expressed with a library of human antibody heavy chains. The resulting human antibodies are screened once more for antigen binding. Techniques such as this one are further described in U.S. Pat. No. 5,565,332. In addition, an antigen can be used to inoculate an animal that is transgenic for human immunoglobulin genes. See, e.g., U.S. Pat. No. 5,661,016.

The present disclosure also provides bispecific antibodies. A bispecific antibody has binding specificities for at least two different antigens (including different epitopes). In some embodiments, a bispecific antibody of the present disclosure includes two or more different VH and/or VL domains that specifically bind PSGL-1. In some embodiments, the two or more different VH and/or VL domains specifically bind the same epitope of PSGL-1. In some embodiments, the two or more different VH and/or VL domains specifically bind different epitopes of PSGL-1, which may or may not be overlapping epitopes.

A bispecific antibody (a monoclonal antibody that has binding specificities for at least two different antigens) can be prepared using the antibodies disclosed herein. Methods for making bispecific antibodies are known in the art (see, e.g., Suresh et al., 1986, *Methods in Enzymology* 121:210). Traditionally, the recombinant production of bispecific antibodies was based on the coexpression of two immunoglobulin heavy chain-light chain pairs, with the two heavy chains having different specificities (Millstein and Cuello, 1983, *Nature* 305, 537-539). In some embodiments, a bispecific tetravalent antibody may be produced using the methods exemplified supra.

According to one approach to making bispecific antibodies, antibody variable domains with the desired binding specificities (antibody-antigen combining sites) are fused to immunoglobulin constant domain sequences. In some embodiments, the fusion is with an immunoglobulin heavy chain constant domain, comprising at least part of the hinge, CH2, and CH3 regions. In some embodiments, the first heavy chain constant region (CH1), containing the site necessary for light chain binding, is present in at least one of the fusions. DNAs encoding the immunoglobulin heavy chain fusions and, if desired, the immunoglobulin light chain, are inserted into separate expression vectors, and are cotransfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

Heteroconjugate antibodies, comprising two covalently joined monomers or antibodies, are also within the scope of the present disclosure. Such antibodies have been used to target immune system cells to unwanted cells (U.S. Pat. No. 4,676,980), and for treatment of HIV infection (PCT Publication Nos. WO 91/00360 and WO 92/200373; and EP 03089). Heteroconjugate antibodies may be made using any convenient cross-linking methods. Suitable cross-linking agents and techniques are well known in the art, and are described in U.S. Pat. No. 4,676,980.

Certain aspects of the present disclosure relate to antibody variable domains and/or antibody fragments, e.g., that may be used as a constituent of a tetravalent antibody described herein. Antibody fragments may contain the active binding region of the antibodies, such as Fab, F(ab')$_2$, scFv, Fv fragments, and the like. Various methods known in the art may be used to produce and/or isolate antibody fragments, which may be incorporated into a tetravalent antibody of the present disclosure, e.g., by standard recombinant techniques known in the art based on the concepts described herein.

Single-chain Fv fragments may be produced, such as described in Iliades et al., 1997, *FEBS Letters,* 409:437-441. Coupling of such single-chain fragments using various linkers is described in Kortt et al., 1997, *Protein Engineering,* 10:423-433. A variety of techniques for the recombinant production and manipulation of antibodies are well known in the art. Such fragments can be produced from the monoclonal antibodies described herein using techniques well established in the art (Rousseaux et al. (1986), in *Methods Enzymol.,* 121:663-69 Academic Press).

Methods of preparing antibody fragments are well known in the art. For example, an antibody fragment can be produced by enzymatic cleavage of antibodies with pepsin to provide a 100 Kd fragment denoted F(ab')$_2$. This fragment can be further cleaved using a thiol reducing agent, and optionally a blocking group for the sulfhydryl groups resulting from cleavage of disulfide linkages, to produce 50 Kd Fab' monovalent fragments. Alternatively, an enzymatic cleavage using papain produces two monovalent Fab fragments and an Fc fragment directly. These methods are described, for example, by U.S. Pat. Nos. 4,036,945 and 4,331,647 and references contained therein, which patents are incorporated herein by reference. Also, see Nisonoff et al. (1960), *Arch Biochem. Biophys.* 89: 230; Porter (1959), *Biochem. J.* 73: 119; Smyth (1967), Methods in Enzymology 11: 421-426. Alternatively, the Fab can be produced by inserting DNA encoding Fab of the antibody into an expression vector for prokaryote or an expression vector for eukaryote, and introducing the vector into a prokaryote or eukaryote to express the Fab.

IV. Methods and Uses

Certain aspects of the present disclosure relate to methods and uses for the tetravalent antibodies described herein. These methods and uses are based at least in part on the properties of the tetravalent antibodies as described herein, including without limitation their increased number of epitope binding domains, potential for lesser dependence upon cross-linking in vitro and/or in vivo, differential potency for inducing apoptosis (e.g., of human PSGL-1 expressing cells), and/or enhanced in vivo or trans vivo efficacy.

As described herein, PSGL-1 is known to be involved in inflammation and T cell biology. The tetravalent antibodies of the present disclosure that specifically bind human PSGL-1 may find use, inter alia, in treating individuals with diseases related to T cell function (e.g., a T-cell mediated inflammatory disease), or individuals in need of medical procedures that may result in inflammatory conditions such as immunological reactions, or for which such conditions are managed beforehand (e.g., a transplantation or transfusion).

In some embodiments, a disorder or disease treated by the methods described herein may be a T-cell mediated inflammatory disease. Non-limiting examples of disorders and diseases that can be treated, or one or more of whose symptoms may be ameliorated or prevented using the tetravalent antibodies described herein described herein include psoriasis, Crohn's disease, ankylosing spondylitis, arthritis (including rheumatoid arthritis, juvenile rheumatoid arthritis, osteoarthritis, and psoriatic arthritis), diabetes mellitus, multiple sclerosis, encephalomyelitis, myasthenia gravis, systemic lupus erythematosus, autoimmune thyroiditis, dermatitis (including atopic dermatitis and eczematous dermatitis), Sjogren's Syndrome, aphthous ulcer, iritis, conjunctivitis, keratoconjunctivitis, type I diabetes, inflammatory bowel diseases, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, graft versus host disease (GVHD), sarcoidosis, primary biliary cirrhosis, uveitis posterior, interstitial lung fibrosis, allergies such as atopic allergy, AIDS, and T cell neoplasms such as leukemias or lymphomas. In some embodiments, the disease is an autoimmune disease.

In another embodiment, the disease or disorder treated in accordance with the methods described herein is plaque psoriasis. Plaque psoriasis or psoriasis vulgaris is the most common form of psoriasis and is characterized by sharply demarcated, raised erythematous skin plaques covered by silvery scale. There is a predilection of the lesions to involve the extensor surfaces of the extremities, the lumbosacral area, and the scalp. The corresponding histopathological findings include significant inflammatory cellular infiltration of the dermis and epidermis, increased numbers of dilated vessels, and a substantial thickening of the epidermis with disordered differentiation of keratinocytes and hyperkeratosis. Approximately one third of patients with plaque psoriasis are categorized as having moderate or severe disease and are consequently candidates for therapy beyond just topical treatment.

In another embodiment, the disorder treated in accordance with the methods described herein is chronic plaque psoriasis. Symptoms of plaque chronic psoriasis include, but are not limited to, single or multiple raised reddened patches of skin, ranging from coin-sized to larger, on any part of the body, including but not limited to the knees, elbows, lumbosacral regions, scalp, and nails.

In another embodiment, the disorder treated in accordance with the methods described herein is guttate psoriasis.

Symptoms of guttate psoriasis include, but are not limited to, flares of water drop shaped scaly plaques on the skin, followed by an infection, such as a streptococcal throat infection.

In another embodiment, the disease or disorder treated in accordance with the methods described herein is inverse psoriasis. Symptoms of inverse psoriasis include, but are not limited to, smooth, usually moist areas of skin that are red and inflamed, unlike the scaling associated with plaque psoriasis, on one or more of the following body parts: armpits, groin, under the breasts, and in other skin folds around the genitals and buttocks.

In another embodiment, the disease or disorder treated in accordance with the methods described herein is pustular psoriasis. Symptoms of pustular psoriasis include, but are not limited to, pus-filled blisters that vary in size and location, but mostly on the hands and feet.

In another embodiment, the disease or disorder treated in accordance with the methods described herein is erythodermic psoriasis. Symptoms of erythodermic psoriasis include, but are not limited to, periodic, widespread, fiery redness of the skin and the shedding of scales in sheets, rather than smaller flakes. The reddening and shedding of the skin are often accompanied by severe itching and pain, heart rate increase, and fluctuating body temperature.

In another embodiment, the disease or disorder treated in accordance with the methods described herein is rheumatoid arthritis. Symptoms of rheumatoid arthritis, include, but are not limited to, fatigue, loss of appetite, low fever, swollen glands, weakness, joint pain in wrists, elbows, shoulders, hips, knees, ankles, toes, jaw, hands, feet, fingers, and/or neck, morning stiffness, chest pain when taking a breath (pleurisy), eye burning, itching, and discharge, nodules under the skin, numbness, tingling, or burning in the hands and feet.

In another embodiment, the disease or disorder treated in accordance with the methods described herein is Crohn's disease. Symptoms of Crohn's disease, but are not limited to, crampy abdominal (belly area) pain, fever, fatigue, loss of appetite, pain with passing stool (tenesmus), persistent, watery diarrhea, unintentional weight loss, constipation, eye inflammation, fistulas (usually around the rectal area, may cause draining of pus, mucus, or stools), joint pain, liver inflammation, mouth ulcers, rectal bleeding and bloody stools, skin lumps or sores (ulcers), and swollen gums.

In another embodiment, the disease or disorder treated in accordance with the methods described herein is ankylosing spondylitis. Symptoms of ankylosing spondylitis include, but are not limited to, frequent pain and stiffness in the lower back and buttocks, spine, and/or neck; and pain and tenderness spreading to the ribs, shoulder blades, hips, thighs and heels; inflammation of the eye (iridocyclitis and uveitis), causing redness, eye pain, vision loss, floaters and photophobia; fatigue; and nausea.

In another embodiment, the disease or disorder treated in accordance with the methods described herein is diabetes mellitus. Symptoms of diabetes mellitus include, but are not limited to, loss of weight, polyuria (frequent urination), polydipsia (increased thirst), polyphagia (increased hunger), cardiovascular disease, diabetic retinopathy, diabetic neuropathy, hyperosmolar nonketotic state, and diabetic ketoacidosis.

In some embodiments, a tetravalent antibody or composition of the present disclosure may be administered to the individual before, concurrently with, and/or after a transplantation. For example, as described in greater detail below, a tetravalent antibody or composition of the present disclosure may be administered to increase the likelihood of a favorable treatment outcome, decrease the likelihood of an unfavorable outcome, and/or mitigate or prevent symptoms or unfavorable outcomes occurring before, concurrently with, or after the transplantation has been completed.

As used herein, treating an individual in need of a transplantation may refer to one or more of therapeutic treatment and prophylactic or preventative measures (e.g., increasing the likelihood of a favorable treatment outcome, such as graft survival, graft function, or decreasing the likelihood of an unfavorable outcome, such as an unfavorable response to treatment, or a condition that reduces the likelihood a favorable treatment, such as a transplantation, from occurring). Treating may include without limitation mitigating or preventing conditions and symptoms associated with a disorder or a condition, and/or problems or conditions that interfere with or limit an individual's access to treatment options of a disorder or a condition, such as sensitization, hypersensitization, high panel reactive antibodies (PRA) level and/or presence of pre-existing alloantibodies that limit availability of grafts to an individual awaiting a transplantation. Those in need of treatment include those already with the disorder or condition, as well as those in which the disorder or condition is to be prevented. Treatment of a disorder or condition may suppress immune-mediated events associated with the disorder or condition, ameliorate the symptoms of the disorder or condition, reduce the severity of the disorder or condition, alter the course of the disorder or condition progression, and/or ameliorate or cure the basic disorder or condition.

For example, successful treatment of an individual awaiting transplantation include, but is not limited to, reducing the level of alloantibodies, reducing panel reactive antibodies (PRA), enabling the individual to have more cross-match compatible donors, increasing the likelihood or probability of the individual to receive a graft, shortening the expected waiting period of the individual for a graft, desensitizing the individual, lowering risk of transplant-associated symptoms or conditions (such as immune-mediated events as described below), or any combination thereof.

For example, successful treatment of an individual receiving a transplantation includes, but is not limited to, protection and maintenance of the transplanted organ or tissue for a long term, which comprises controlling, reversing, mitigating, delaying, or preventing one or more symptoms or undesirable conditions associated with the organ transplant, such as immune-mediated events, including, but not limited to, production of donor-specific alloantibodies (DSA), GVHD, antibody-mediated rejection (AMR), hyperacute graft rejection, chronic graft rejection, graft failure, and graft loss, as measured by functional or histological signs of the symptom or condition. A treatment capable of controlling a disorder or condition (e.g., graft rejection) may include a treatment that slows the progression of the disease process, when initiated after functional or histological signs of the disorder or condition (e.g., graft rejection) are observed. Further, a treatment capable of reversing a disease or condition (e.g., graft rejection) may include a treatment that, when initiated after functional or histological signs of the disease or condition (e.g., graft rejection) have appeared, reverses the disease process and returns functional and histological findings closer to normal. A treatment capable of "delaying progression" of a disorder or condition (e.g., graft rejection) may include deferring, hindering, slowing, retarding, stabilizing, and/or postponing development of the disorder or condition (e.g., graft rejection). This delay can be of varying lengths of time, depending on the history of the disease and/or individual being treated. As is evident to one skilled in the art, a sufficient or significant delay can, in effect, encompass prevention, in that the individual, e.g., an individual at risk for developing the disorder or condition, does not develop the disorder or condition.

In some embodiments, a transplantation of the present disclosure may be transplantation of one or more tissues or organs including without limitation bone marrow, kidney, heart, liver, neuronal tissue, lung, pancreas, skin, and intestine (e.g., small and/or large intestine, as well as any sub-tissues thereof).

In addition, tetravalent antibodies are useful for preventing and/or treating certain disorders and diseases associated with or caused (in whole or in part) by increased proliferation and/or numbers of activated T cells relative to the proliferation and/or numbers of activated T cells found in healthy individuals or individuals not having the particular disorder or disease. Non-limiting examples of disorders and diseases that can be prevented and/or treated using the tetravalent antibodies described herein include graft-versus-host disease and cases of transplantation rejection (including transplantation rejection using allogeneic or xenogeneic tissues) such as bone marrow transplantation, liver transplantation, kidney transplant, or the transplantation of any organ or tissue.

In some embodiments, a tetravalent antibody or composition of the present disclosure may be administered to the individual before, concurrently with, and/or after a transfusion. For example, as described in greater detail below, a tetravalent antibody or composition of the present disclosure may be administered to increase the likelihood of a favorable treatment outcome, decrease the likelihood of an unfavorable outcome, and/or mitigate or prevent symptoms occurring before, concurrently with, or after the transfusion has been completed.

As used herein, treating an individual in need of a transfusion may refer to one or more of therapeutic treatment and prophylactic or preventative measures (e.g., increasing the likelihood of a favorable treatment outcome, such as replacement or supplementation of blood components/cells, or decreasing the likelihood of an unfavorable outcome, such as an unfavorable response to treatment, inefficacy of treatment, or immunological reaction, or a condition that reduces the likelihood a favorable treatment, such as a transfusion, from occurring). Treating may include without limitation mitigating or preventing conditions and symptoms associated with a disorder or a condition, and/or problems or conditions that interfere with or limit an individual's access to treatment options of a disorder or a condition. Those in need of treatment include those already with the disorder or condition, as well as those in which the disorder or condition is to be prevented. Treatment of a disorder or condition may suppress immune-mediated events associated with the disorder or condition, ameliorate the symptoms of the disorder or condition, reduce the severity of the disorder or condition, alter the course of the disorder or condition progression, and/or ameliorate or cure the basic disorder or condition.

In some embodiments, the transfusion is a transfusion comprising one or more of white blood cells, red blood cells, and platelets. In some embodiments, the transfusion comprises whole blood or one or more blood products, including without limitation white blood cells, red blood cells, platelets, fresh frozen plasma, cryoprecipitate or blood clotting factors, antibodies, and/or blood substitutes. Exemplary conditions that may be treated with a transfusion (e.g., transfusion of blood or a blood product) include without limitation hemorrhage or blood loss, reduced hematocrit or hemoglobin (e.g., anemia), sickle cell disease, thalassemia, blood supplementation during or after surgical procedures, cardiac disease, traumatic injury, deficiency of one or more blood factors (e.g., hemophilia, von Willebrand disease, hypofibrinogenemia, or a deficiency in factor II, V, VII, IX, X, or XI), conditions requiring fibrinogen supplementation (e.g., liver disease, blood transfusion, etc.), bone marrow failure, platelet function disorders, thrombocytopenia, immunodeficiency (e.g., from a therapy or disease), and the like. Descriptions of practices, dosing, responses, indications, and preparations related to transfusions may be found, e.g., in the American Red Cross Compendium of Transfusion Practice Guidelines.

Administration of a tetravalent antibody or polypeptide in accordance with the methods described herein can be continuous or intermittent, depending, for example, upon the recipient's physiological condition, whether the purpose of the administration is therapeutic or prophylactic, and other factors known to skilled practitioners. The administration of an antibody or a polypeptide may be essentially continuous over a preselected period of time or may be in a series of spaced dose.

The dosage and frequency of administration of a tetravalent antibody described herein or a pharmaceutical composition thereof is administered in accordance with the methods for preventing and/or treating while minimizing side effects. The exact dosage of a tetravalent antibody described herein to be administered to a particular subject or a pharmaceutical composition thereof can be determined by a practitioner, in light of factors related to the subject that requires treatment. Factors which can be taken into account include the severity of the disease state, general health of the subject, age, and weight of the subject, diet, time and frequency of administration, combination(s) with other therapeutic agents or drugs, reaction sensitivities, and tolerance/response to therapy. The dosage and frequency of administration of a tetravalent antibody described herein or a pharmaceutical composition thereof can be adjusted over time to provide sufficient levels of the antibody or an antibody derived antigen-binding fragment, or to maintain the desired effect.

The precise dose to be employed in the formulation will also depend on the route of administration, and the seriousness of an inflammatory disorder or disease, and should be decided according to the judgment of the practitioner and each patient's circumstances.

Effective doses can be extrapolated from dose-response curves derived from in vitro or animal model test systems.

In one embodiment, any of the compositions described herein is formulated for administration by intraperitoneal, intravenous, subcutaneous, or intramuscular injections, or other forms of administration such as oral, mucosal, via inhalation, sublingually, etc. Parenteral administration, in one embodiment, is characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered can also contain minor amounts of non-toxic auxiliary substances such as wetting or emulsifying agents, pH buffering agents, stabilizers, solubility enhancers, and other such agents. Other routes of administration may include, enteric administration, intracerebral administration, nasal administration, intraarterial administration, intracardiac administration, intraosseous infusion, intrathecal administration, intravenous infusion, subcutaneous implantation or injection, intramuscular administration, intrarectal administration intravaginal administration, intragastrical administration, intratracheal administration, intrapulmonary administration and intraperitoneal administration. Preparations for parenteral administration include sterile solutions ready for injection, sterile dry soluble products, such as lyophilized powders, ready to be combined with a solvent just prior to use, including sterile suspensions ready for injection, sterile dry insoluble products ready to be combined with a vehicle just prior to use and sterile emulsions. The solutions can be either aqueous or nonaqueous. If administered intravenously, suitable carriers include physiological saline or phosphate buffered saline (PBS), water, and solutions containing thickening and solubilizing agents, such as glucose, polyethylene glycol, and polypropylene glycol and mixtures thereof.

In another embodiment, the present disclosure also contemplates administration of a composition comprising the antibodies or polypeptides of the present disclosure conjugated to other molecules, such as detectable labels, or therapeutic or cytotoxic agents. The agents may include, but are not limited to radioisotopes, toxins, toxoids, inflammatory agents, enzymes, antisense molecules, peptides, cytokines, and chemotherapeutic agents. Methods of conjugating the antibodies with such molecules are generally known to those of skilled in the art. See, e.g., PCT publications WO 92/08495; WO 91/14438; WO 89/12624; U.S. Pat. No. 5,314,995; and EP 396,387.

In one embodiment, the composition comprises an antibody or polypeptide conjugated to a cytotoxic agent. Cytotoxic agents can include any agents that are detrimental to cells. An exemplary class of cytotoxic agents that can be conjugated to the antibodies or fragments may include, but are not limited to, paclitaxol, cytochalasin B, gramicidin D, ethidium bromide, emetine, mitomycin, etoposide, teniposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, and analogs or homologs thereof.

V. Pharmaceutical Compositions

The present disclosure also provides pharmaceutical compositions comprising tetravalent antibodies or polypeptides described herein, and a pharmaceutically acceptable carrier or excipients. The pharmaceutical compositions may find use, e.g., in the methods, uses, and/or kits of the present disclosure.

Pharmaceutically acceptable carriers or excipients are known in the art, and are relatively inert substances that facilitate administration of a pharmacologically effective substance. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers. In certain embodiments, a tetravalent antibody described herein is in a liquid pharmaceutical composition. Liquid pharmaceutically administrable compositions can, for example, be prepared by dissolving, dispersing, or otherwise mixing an antibody described herein in a carrier, such as, for example, water, saline, aqueous dextrose, glycerol, glycols, ethanol, and the like, to thereby form a solution or suspension. If desired, the pharmaceutical composition to be administered can also contain minor amounts of nontoxic auxiliary substances such as wetting agents, emulsifying agents, solubilizing agents, and pH buffering agents and the like. Excipients as well as formulations for parenteral and nonparenteral drug delivery are set forth in *Remington, The Science and Practice of Pharmacy* 20th Ed. Mack Publishing (2000).

The pharmaceutical compositions are provided for administration to humans and animals in unit dosage forms, such as sterile parenteral solutions or suspensions containing suitable quantities of a tetravalent antibody described herein. The tetravalent antibody is, in one embodiment, formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the antibody or the antibody derived antigen-binding fragment sufficient to produce the desired therapeutic effect, in association with the required pharmaceutical carrier, vehicle or diluent. Examples of unit-dose forms include ampoules and syringes. Unit-dose forms can be administered in fractions or multiples thereof. A multiple-dose form is a plurality of identical unit-dosage forms packaged in a single container to be administered in segregated unit-dose form. Examples of multiple-dose forms include vials, or bottles of pints or gallons. Hence, multiple dose form is a multiple of unit-doses which are not segregated in packaging.

The concentration of tetravalent antibody in the pharmaceutical composition will depend on, e.g., the physicochemical characteristics of the antibody or the antibody derived antigen-binding fragment, the dosage schedule, and amount administered as well as other factors known to those of skill in the art. In some embodiments, the pharmaceutical compositions provide a dosage of from about 0.001 mg to about 100 mg of tetravalent antibody per kilogram of body weight per day. Pharmaceutical dosage unit forms can be prepared to provide from about 0.001 mg to about 100 mg, and/or a combination of other optional essential ingredients per dosage unit form.

In some embodiments, the present disclosure provides tetravalent antibodies and compositions (such as the pharmaceutical compositions described herein) for use in any of the methods described herein, whether in the context of use as a medicament and/or use for manufacture of a medicament.

VI. Kits

Certain aspects of the present disclosure are related to kits or articles of manufacture that comprise a tetravalent antibody of the present disclosure. Optionally, the kits described herein may contain one or more pharmaceutically acceptable carriers, such as the exemplary carriers described herein. In some embodiments, a kit of the present disclosure includes a pharmaceutical composition of the present disclosure. Kits described herein may find use, e.g., in the methods or uses of the present disclosure.

Kits may optionally provide additional components such as buffers and interpretive information. Normally, the kit comprises a container and a label or package insert(s) on or associated with the container. The containers may be unit doses, bulk packages (e.g., multi-dose packages) or sub-unit doses. Instructions supplied in the kits of the present disclosure are typically written instructions on a label or package insert (e.g., a paper sheet included in the kit), but machine-readable instructions (e.g., instructions carried on a magnetic or optical storage disk) are also acceptable.

In some embodiments, the kits further include a package insert comprising instructions for administration of the tetravalent antibody to treat a T-cell mediated inflammatory disease. In some embodiments, the kits further include a package insert comprising instructions for administration of the tetravalent antibody before, concurrently with, and/or after a transfusion or transplantation.

The kits of the present disclosure are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer), or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is a tetravalent antibody or polypeptide described herein. The container may further comprise a second pharmaceutically active agent. In some embodiments, a kit may further include any other material or device useful in a treatment (e.g., a transfusion or transplantation), including without limitation one or more containers, tubing, sterilizing agents or equipment, cannulae, syringes, and the like.

EXAMPLES

The invention will be more fully understood by reference to the following examples. They should not, however, be construed as limiting the scope of the invention. It is understood that the examples and embodiments described herein are for illustrative purposes only and that various modifications or changes in light thereof will be suggested to persons skilled in the art and are to be included within the spirit and purview of this application and scope of the appended claims.

Example 1: Generation and Characterization of Anti-PSGL-1 Tetravalent Antibodies P-selectin Glycoprotein Ligand-1 (PSGL-1) is expressed on a wide range of hematopoietic cells, including myeloid, lymphoid, dendritic, and CD34+ stem cell populations (see, e.g., Spertini et al. 1996, *J Cell Biol.* 135(2):523-31). Several mouse antibodies specific for PSGL-1 and capable of inducing apoptosis in T cells have previously been identified. Among these mouse antibodies, an antibody (h15A7) that did not interfere with the interaction between P-selectin and PSGL-1, which required for efficient localization of T cells and neutrophils to target inflammatory tissues, was chosen for clinical development and was modified to a humanized kappa-light-chain containing IgG4 monoclonal antibody to minimize ADCC and CDC on PSGL-1 expressing cells (see, e.g., U.S. Pat. No. 7,604,800). Subsequently, h15A7 was further engineered to produce h15A7H, which has a mutation of SER228PRO in hinge region of h15A7 (International Application Pub. No. WO 2012/174001). This mutation was introduced in order to reduce antibody shuffling, the intermolecular exchange among IgG4 antibodies in vivo. In vitro studies showed that h15A7/h15A7H preferentially induced apoptosis of late-stage activated T cells but not other PSGL-1-expressing cells. Without wishing to be bound to theory, it is thought that the mechanism of action of h15A7H appears to be dependent at least in part on cross-linking of human PSGL-1 molecules, which is mediated by antibody cross-linker in vitro and possibly FcR-expressing cells in vivo.

Figure 1B:
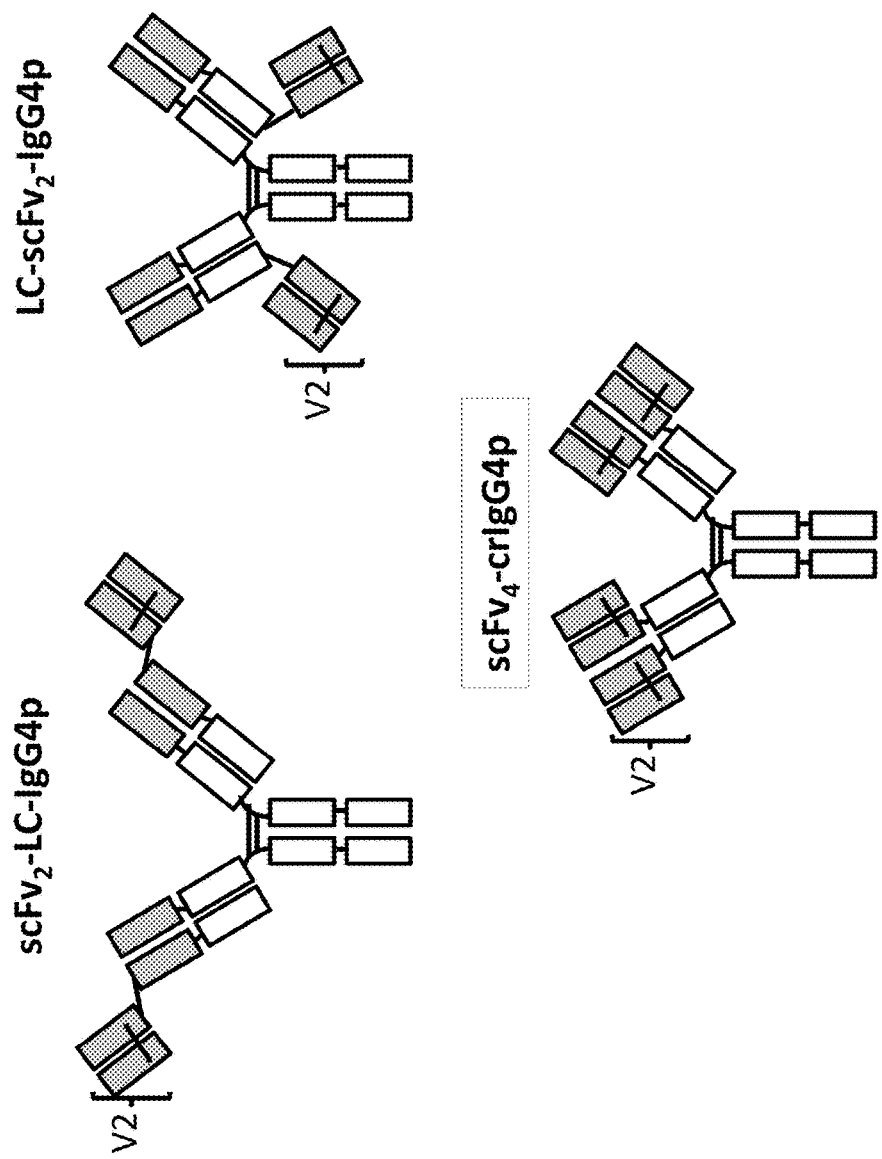

The Example presented below describes the development of several cross-linker/FcR-expressing cell-independent tetravalent antibodies derived from h15A7H (FIGS. 1A & 1B). Without wishing to be bound to theory, tetravalent antibodies may possess advantages over h15A7H for clinical development, e.g., treatment of T-cell mediated inflammatory diseases. These results demonstrate that tetravalent h15A7H antibodies show enhanced efficacy compared to the parental h15A7H antibody both in vitro and trans vivo.

Methods

Cells and Reagents

Sp2/0-Ag14 (ATCC® CRL-1581™) and Sp2/0-hPSGL-1 were cultured in 90% DMEM (GIBCO®, Cat. No. 11965-092™) supplemented with 10% FBS (GIBCO®, Cat. No. 26140-079), 100 U/mL penicillin/100 µg/mL streptomycin (GIBCO®, Cat. No. 15140) and 1 mM sodium pyruvate (GIBCO®, Cat. No. 11360).

The h15A7H antibody was described in International Application Pub. No. WO 2012/174001. The h15A7H tetravalent antibodies used in the study were produced from a Flp-In CHO stable cell line, purified by protein A affinity chromatography, and maintained in Dulbecco's Phosphate-Buffered Saline (GIBCO® Cat. No. 21600-069)/0.02% Tween-20 (JT Baker® X251-07). Human IgG4p/K as irrelevant isotype control antibody was produced from Flp-In CHO cells. 12H5.5 is a murine IgG1 anti-idiotype antibody against h15A7/h15A7H.

Animals

Female B6 mice at 6-8 weeks of age were obtained from BioLASCO Taiwan Co., Ltd, Taipei, Taiwan. All mice were maintained under specific pathogen-free conditions. All animal studies were conducted following the guidelines of the Institutional Animal Care and Use Committee.

Construction of Anti-PSGL-1 Tetravalent Antibody Variants scDb$_2$-Fc scDb$_2$-Fc (FIG. 1A, left) included 2 domains of single-chain diabodies (scDbs) fused in parallel to the N-terminals of human IgG4 Fc with a mutation in the hinge region to minimize half-antibody exchange in vivo. Each scDb domain contained not only a domain sequence of VL-VH-VL-VH, but also a linker $(G_4S_1)_5$ (SEQ ID NO:33) between VH and VL and two identical linkers (e.g., SEQ ID NO:34) between VL and VH. Several scDb-Fcs with said linkers of different length were generated for optimization taFv$_2$-Fc taFv$_2$-Fc (FIG. 1A, middle) included 2 tandem single-chain variable fragment (scFv) units (termed taFv for tandem scFv) fused in parallel to the N-terminals of human IgG4 Fc with a mutation in the hinge region to minimize half-antibody exchange in vivo. There were three different kinds of scFvs used to construct taFv, including v2 (VH-VL), v3 (VL-VH), and v4 (VL-VH) versions, containing a linker $(G_4S_1)_5$ (SEQ ID NO:33) between VH and VL. Among them, v2 and v4 were structure-constrained by the formation of VH44-VL100 disulfide bond. The VH44-VL100 disulfide bond was introduced into scFv in both VL-VH and VH-VL orientations for increased conformational stability (see SEQ ID NOs:29 and 30). Each taFv had either sequential v2-v3 or sequential v4-v2 of anti-PSGL-1 scFv with a linker ASTGS (SEQ ID NO:27) between the two scFvs.

scFv-IgG

The disulfide-constrained v2 version of anti-PSGL-1 scFv was used to generate 3 scFv-IgG4p variants (FIG. 1A, right), including scFv$_4$-crIgG4p, scFv$_2$-LC-IgG4p, and LC-scFv$_2$-IgG4p. scFv$_4$-crIgG4p had 4 scFv units fused in parallel to the N-terminals of both constant regions of kappa light chain and heavy chain of IgG4p (crIgG) without a linker. scFv$_2$-LC-IgG4p had 2 scFv units fused in parallel to the N-terminals of kappa light chains of h15A7H IgG with a linker ASTGSG$_4$S (SEQ ID NO:28) in-between, whereas LC-scFv$_2$-IgG4p had 2 scFv units fused in parallel to the C-terminals of kappa light chains of h15A7H IgG with a linker (G$_4$S)$_2$ (SEQ ID NO:34) in-between. Light chains of LC-scFv$_2$ IgG4p and scFv$_2$-LC IgG4p formats were separately sub-cloned into a pcDNA5/FRT vector that encoded an intact h15A7H heavy chain sequence for antibody expression. FIG. 1B shows another diagram of these tetravalent antibody formats with the variable fragments shaded.

cDNAs of all tetravalent antibodies were cloned into the pcDNA5/FRT vector (Invitrogen™, Cat. No: V6010-20) for tetravalent antibody expression.

Production of Stable Cell Lines Expressing Anti-PSGL-1 Tetravalent Antibody Variants Anti-PSGL1 tetravalent antibody variants were stably expressed and produced in F CHO cells (Invitrogen™, Cat. No: R708-07). The cDNA sequences of tetravalent antibody variants were inserted into the pcDNA5/FRT vector (Invitrogen™, Cat. No: V601.0-20) and cotransfected with pOG44 (Invitrogen™, Cat. No V6005-20) following the standard procedure provided by the vendor. The culture supernatants of the established cell lines were collected and purified with protein A sepharose beads (GE Healthcare™, Cat. No: 17-5280-04). The purified proteins were analyzed with both SDS-PAGE and size exclusion chromatography to ensure the quality of antibodies.

Reducing and Non-Reducing SDS-PAGE (Sodium Dodecyl Sulfate Polyacrylamide Gel Electrophoresis)

Purified anti-PSGL-1 tetravalent antibodies were electrophoresed in 10% reducing and non-reducing SDS polyacrylamide gels. For the reducing SDS polyacrylamide gels, 2 μg of antibody were mixed with 5×SDS sample buffer (300 nM Tris, pH6.8, 10% SDS, 50% glycerol, 5% 2-mercaptoethanol and 0.06% bromophenol blue) and boiled for 10 min at 100° C. before loading. For the non-reducing SDS polyacrylamide gels, 2 μg of antibodies were mixed with 5× non-reducing sample buffer (300 nM Tris, pH6.8, 10% SDS, 50% glycerol and 0.06% bromophenol blue) and boiled for 10 min at 100° C. before loading. The reducing and non-reducing protein samples were loaded onto the same SDS-polyacrylamide gels where electrophoresis was performed. Coomassie blue staining was used to detect proteins on the gel after electrophoresis.

Binding Assay of Anti-PSGL-1 Tetravalent Antibody Variants

Sp2/0 cells transfected with human PSGL-1(Sp2/0-hPSGL1) were used as the PSGL-1 expressing cell line. Sp2/0-hPSGL1 cells were centrifuged at 1200 rpm for 5 min. The cell pellets were resuspended in FACS buffer (PBS containing 1% FBS) and pipetted into 96 well plate (1×10$^5$ cells/well). To each well was added 100 μl of supernatants containing humanized 15A7H(h15A7H)/tetravalent antibodies, and these were incubated for 60 min at 4° C. The cells were washed three times with cold FACS buffer and then incubated with 100 μl of Mouse Anti-Human IgG$_4$ pFc'-PE (SouthernBiotech Cat. no. 9190-09) at 1 μg/ml concentration for 60 min at 4° C. Subsequently, the cells were washed three times with cold FACS buffer and analyzed by FACS analysis. All flow cytometric analyses were performed on a BD-LSR flow cytometer (Becton Dickinson) using the Cell Quest software.

Apoptosis Assay of Anti-PSGL-1 Tetravalent Antibody Variants

1×10$^5$ Sp2/0-hPSGL1 cells were seeded into the wells of 96-well plates. Aliquots of purified anti-PSGL-1 tetravalent and control antibodies at titrated concentrations were prepared freshly and added to each well. The treated cells were kept at 37° C. for 6 hr before FACS analysis for cellular apoptosis assay.

For the cellular apoptosis assay, an Annexin-V-FITC Apoptosis Detection Kit (Strong Biotech, Cat. No. AVK250) was used following the manufacturer's instructions. In brief, the treated cells were harvested and resuspended in 100 μl Annexin V binding buffer containing 0.5 μl Annexin V-FITC at room temperature. After 15 min incubation in the dark, the cells were washed twice with 200 μl of Annexin V binding buffer. Before FACS analysis, 1 μl of propidium iodide (PI) per sample was added. All flow cytometric analyses were performed on a BD-LSR flow cytometer (Becton Dickinson) using Cell Quest software. The Annexin V positive and/or PI positive cells are considered apoptotic cells.

Isolation of Human Peripheral Blood Mononuclear Cells (PBMCs)

500 ml whole blood was collected from healthy donors that were previously tested as good tetanus responders. The blood was centrifuged at 1500 rpm for 6 min. The upper plasma layer was discarded, and the remnant blood was diluted with an equivalent volume of PBS. The diluted whole blood was carefully added over a Ficoll (GE, Ficoll Plaque Plus, Cat #17-1440-02) layer and centrifuged at 2400 rpm for 15 mins at room temperature. The buffy coat layer containing mononuclear cells was collected and washed with PBS 3 times to minimize platelet contamination. The cells were resuspended in PBS and kept on ice before use.

Trans-Vivo Delayed Type Hypersensitivity (DTH)

8-10×10$^6$ PBMC cells, along with 0.25LF unit of PBS-dialyzed Tetanus Toxoid (TT, Kuo Kwang, Cat# K4103-11) or PBS, were injected in a final volume of 50 μl into the hind footpad of female B6 mice. Mice of 6~8 weeks were used in all experiments. Footpad thickness was measured before and 24 hrs post injection using a dial thickness gauge. The pre-injected value was subtracted from post-injection value to obtain the net paw thickness. All measurement values were recorded in millimeters (mm). h15A7H and h15A7H tetravalent antibodies titrated in PBS were intravenously administered at indicated doses into B6 mice one hour prior to PBMC and TT injection. PBS was used as the vehicle control. 2 or 4 paws (1 or 2 mice) per treatment were tested. The plasma samples were collected 24 hrs after Ab administration to check the concentrations of antibody variants. The percent inhibition of paw thickness was calculated as follows: 100×(Δ paw thicknesss$_{veh}$−Δ paw thickness$_{Ab}$)/(Δ paw thickness$_{veh}$−Δ paw thickness$_{PBMC\ only}$).

ELISA for Detecting Antibody Concentration in Mouse Plasma 96-well microtiter plates were coated with anti-idiotype antibody 12H5.5 at 0.5 μg/mL in ELISA coating buffer (30 mM Na$_2$CO$_3$/100 mM NaHCO$_3$) at 4° C. overnight. Plates were then blocked with 200 μL/well of 0.5% BSA in PBS for 1 hour at room temperature, and washed 3 times with ELISA washing buffer (0.05% Tween20 in PBS), followed by addition of 50 μL/well of calibration standard or samples. Calibration standards at a serial dilution were first prepared in the normal mouse plasma. Calibration standard or samples were pre-diluted 1000× in assay diluent (0.1% BSA and 0.05% Tween 20 in PBS), to make a final concentration of 0.1% mouse plasma in assay diluents, before dispensing onto the plates. Subsequent dilutions, if needed, were prepared using assay diluents containing 0.1% normal mouse plasma. After 1 hour incubation at room temperature and washing 5 times with ELISA washing buffer, the secondary antibody mouse anti-human $IgG_4$ pFc'-HRP (SouthernBiotech Cat. no. 9190-05; dilution 1:15000) was added at 50 µL/well and incubated at room temperature for 1 hour. The plates were then washed 5 times with ELISA washing buffer, followed by addition of TMB substrate for color development. Reactions were stopped by 0.5N $H_2SO_4$, and an absorbance value was measured at 450 nm in a microtiter plate reader (Molecular Device VERSAmax).

Results

Reducing and Non-Reducing SDS-PAGE of Humanized 15A7H Tetravalent Antibodies

Figure 2A:
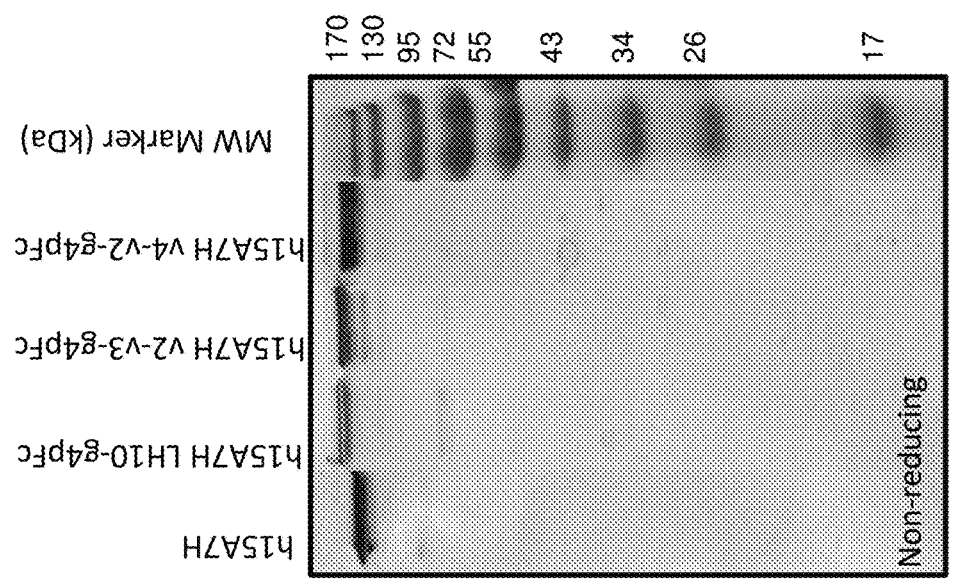
FIGS. 2A-2C show the verification of the molecular weights and basic structures of exemplary tetravalent antibodies by SDS-PAGE followed by Coomassie blue staining. Non-reducing (FIGS. 2A & 2B) and reducing (FIG. 2C) conditions are shown.
Figure 2B:
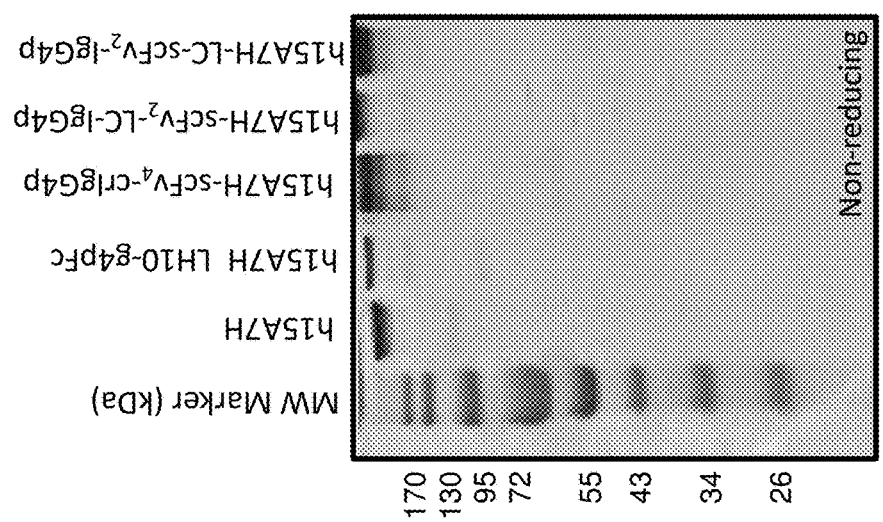
Figure 2C:
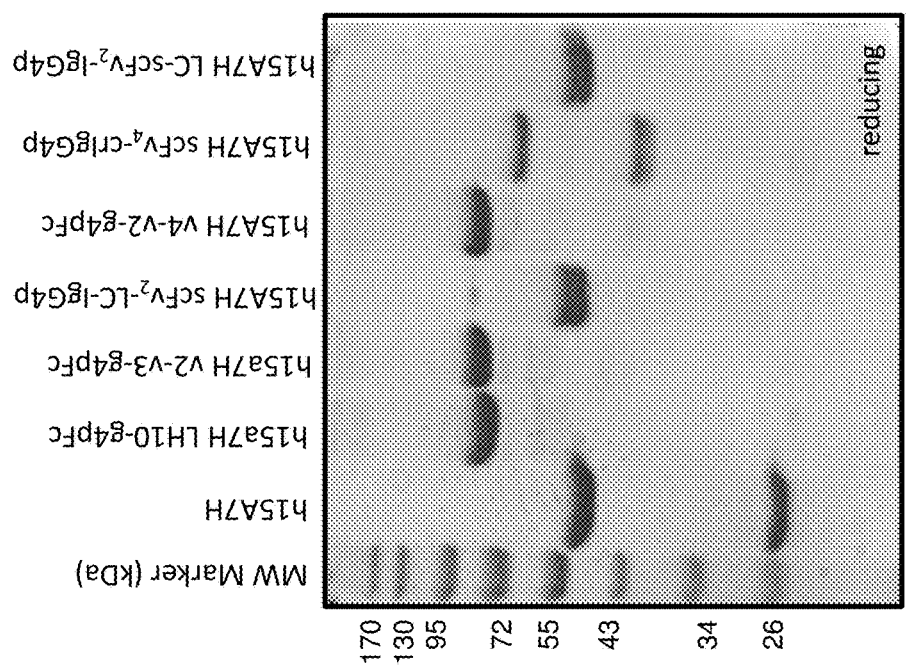

As shown in FIGS. 2A-2C, SDS-PAGE followed by Coomassie blue staining was used to verify the molecular weight and basic structure of anti-PSGL-1 tetravalent antibodies under non-reducing and reducing conditions. h15A7H V2-V3, V4-V2 and LH10-g4pFc under non-reducing conditions yielded a major protein band with a molecular weight of around 150 kDa (FIG. 2A). In the same conditions, h15A7H $scFv_2$-LC IgG4p, LC-$scFv_2$IgG4p, and $scFv_4$-crIgG4p yielded a major protein band with a molecular weight of around 200 kDa (FIG. 2B).

Under reducing conditions, h15A7H V2-V3, V4-V2 and LH10 g4pFc showed a single band with the expected molecular weight of around 75 kDa, whereas both h15A7H $scFv_2$-LC and LC-$scFv_2$ showed two major bands with similar molecular weight around 50 kDa (FIG. 2C). One band was the scFv-LC or LC-scFv fusion protein, and the other was the wild type h15A7H heavy chain. $scFv_4$-crIgG4p also showed two major bands, one representing the scFv-CH1-hinge-CH2-CH3 (around 62.5 kDa) fusion protein, and the other the scFv-kappa-fusion (around 37.5 kDa) protein (FIG. 2C). As control, the h15A7H gave a single band with an expected molecular weight of 150 kDa in the non-reducing gels (FIGS. 2A & 2B) and two major bands (heavy chain: 50 kDa, light chain: 25 kDa) under reducing conditions (FIG. 2C).

Binding of Humanized 15A7H Tetravalent Antibody Variants to SP2/0-hPSGL-1 and SP2/0

The binding ability of h15A7H tetravalent antibodies was evaluated in human PSGL-1 SP2/O cells. The h15A7H tetravalent antibody bound positively to the SP2/O-hPSGL-1, but not to parental SP2/O cell lacking of hPSGL-1 antigen (Table A below). Additionally, wild type h15A7H and all of h15A7H tetravalent antibodies gave similar binding activity on SP2/O-hPSGL-1 (Table A). These results demonstrated that h15A7H tetravalent antibodies retained binding reactivity to hPSGL-1 molecule.

TABLE A

Binding activity (measured by mean florescence intensity) of humanized 15A7H tetravalent antibodies to SP2/O-hPSGL-1 and SP2/O.

| (µg/mL) | SP2/O-hPSGL-1 | | | | SP2/O | | | |
|---|---|---|---|---|---|---|---|---|
| | 3 | 1 | 0.3 | 0.1 | 3 | 1 | 0.3 | 0.1 |
| h15A7H | 4667 | 6400 | 5943 | 3410 | 17 | 26 | 8 | 8 |
| h15A7H LH10-g4pFc | 4627 | 6677 | 5410 | 2902 | 19 | 18 | 31 | 30 |
| h15A7H V2-V3-g4pFc | 4535 | 6260 | 5731 | 3156 | 33 | 22 | 26 | 17 |
| h15A7H $scFv_2$-LC-IgG4p | 4382 | 5744 | 7060 | 5543 | 24 | 12 | 11 | 24 |
| h15A7H V4-V2-g4pFc | 4923 | 6779 | 6454 | 3953 | 23 | 20 | 21 | 14 |
| h15A7H $scFv_4$-crIgG4p | 5938 | 6013 | 4637 | 2640 | 30 | 28 | 18 | 8 |
| h15A7H LC-$scFv_2$-IgG4p | 6026 | 5822 | 3477 | 3042 | 24 | 23 | 25 | 3 |
| hIgG4p (control) | 28 | ND | ND | ND | 33 | ND | ND | ND |

ND: not done

In Vitro Apoptosis of SP2/O-hPSGL-1 Cells Induced by Humanized 15A7H Tetravalent Antibodies Induction of apoptosis was evaluated by staining of Annexin V and/or PI in SP2/O-hPSGL-1 cells after incubation with h15A7H or tetravalent antibody. As shown in Table B below, the parental antibody, h15A7H, did not induce apoptosis in SP2/O-hPSGL-1 cells at the tested concentration of 0.5 and 0.0625 µg/mL in the absence of cross-linker. At the tested concentrations of 0.5 µg/mL, all of the h15A7H tetravalent antibodies induced apoptosis (ranging from 18-36%). At the lowest tested concentration tested (0.0625 µg/mL), 3 out of 6 tetravalent h15A7H antibodies, LH10-g4pFc, V2-V3-g4pFc, and $scFv_2$-LC-IgG4p, induced apoptosis in 12-16% of cells, whereas h15A7H V4-V2-g4pFc, $scFv_4$-crIgG4p, and LC-$scFv_2$-IgG4p did not induce cell death in SP2/0-hPSGL-1 at this lower dose. These data clearly demonstrate that all of the h15A7H tetravalent antibodies possess apoptosis-inducing ability, but that some tetravalent antibodies do so with greater potency.

TABLE B

In vitro apoptosis of SP2/O-hPSGL-1 cells induced by humanized 15A7H tetravalent antibodies.

| Apoptosis % (substrate background, n = 4) | 0.5 µg/mL | | 0.0625 µg/mL | |
|---|---|---|---|---|
| | mean | SD | mean | SD |
| h15A7H | 2.75 | 3.95 | 1.5 | 3.32 |
| h15A7H LH10-g4pFc | 26.75 | 11.32 | 11.75* | 5.50 |
| h15A7H V2-V3-g4pFc | 26.5 | 5.69 | 13.5* | 5.45 |
| h15A7H $scFv_2$-LC-IgG4p | 23.75 | 9.00 | 15.5* | 5.69 |
| h15A7H V4-V2-g4pFc | 30 | 4.55 | 0.5 | 3.00 |
| h15A7H $scFv_4$-crIgG4p | 35.75 | 7.63 | 1.75 | 2.87 |
| h15A7H LC-$scFv_2$-IgG4p | 18 | 9.83 | 0.5 | 4.20 |

SD: standard deviation
*T-test P value<0.05 (compared to treatment with V4-V2-g4pFc, $scFv_4$-crIgG4p and LC-$scFv_2$-IgG4p).

Efficacy of h15A7H and h15A7H Tetravalent Antibodies in the Inhibition of Trans-Vivo DTH Response in B6 Mice The h15A7H and h15A7H tetravalent antibodies described above were tested for their efficacy in the inhibition of trans vivo DTH response in B6 mice. h15A7H antibody was intravenously injected into mice at the doses of 10 and 1 mg/kg, whereas tetravalent antibodies were intravenously injected into mice at the doses of 1 and 0.3 mg/kg. Experiments were conducted using PBMCs from four different donors, and % inhibition was calculated to evaluate the in vivo inhibitory efficacy.

As shown in Table C below, h15A7H antibody could inhibit footpad swelling by a mean of 93% at the dose of 10 mg/kg. The inhibition effect was reduced to 23% at the low dose of 1 mg/kg. As for 15A7H tetravalent antibodies, variants such as h15A7H LH10-g4p Fc, V2-V3-g4pFc and scFv$_2$-LC-IgG4p remained effective in inhibition even at doses of 1 or 0.3 mg/kg (with 59-76% inhibition).

TABLE C

Effect of h15A7H and h15A7H tetravalent antibodies on Trans-vivo DTH.

| | Exp. 1 | Exp. 2 | Exp. 3 | Exp. 4 | Mean | SEM |
|---|---|---|---|---|---|---|
| % inhibition at 10 mg/kg | | | | | | |
| h15A7H | 71 | 104 | 82 | 116 | 93 | 10.2 |
| % inhibition at 1 mg/kg | | | | | | |
| h15A7H | 15 | 28 | 18 | 32 | 23 | 4.0 |
| h15A7H LH10-g4pFc | 75 | 51 | 109 | 69 | 76 | 12.1 |
| h15A7H V2-V3-g4pFc | 29 | 33 | 100 | 91 | 63 | 18.7 |
| h15A7H scFv$_2$-LC-IgG4p | 53 | 34 | 104 | 93 | 71 | 16.3 |
| h15A7H V4-V2-g4pFc | ND | ND | 11 | 44 | 27 | 16.5 |
| h15A7H scFv$_4$-crIgG4p | 14 | 2 | −18 | 6 | 1 | 6.8 |
| h15A7H LC-scFv$_2$-IgG4p | −17 | 16 | 14 | 29 | 10 | 9.8 |
| % inhibition at 0.3 mg/kg | | | | | | |
| h15A7H LH10-g4pFc | 28 | 73 | 109 | 50 | 65 | 17.2 |
| h15A7H V2-V3-g4pFc | 24 | 47 | 127 | 80 | 69 | 22.3 |
| h15A7H scFv$_2$-LC-IgG4p | 74 | 24 | 66 | 73 | 59 | 11.8 |
| h15A7H V4-V2-g4pFc | ND | ND | −16 | 11 | −2 | 13.7 |
| h15A7H scFv$_4$-crIgG4p | 2 | 9 | −7 | 6 | 3 | 3.6 |
| h15A7H LC-scFv$_2$-IgG4p | −4 | 19 | 5 | 15 | 9 | 5.2 |

ND: not done.;
SEM: the standard error of the mean

Plasma levels of h15A7H and h15A7H tetravalent antibodies were also measured 24 hrs after i.v. administration (Table D). All of the antibodies showed plasma levels around 6513-9025 ng/mL at 1 mg/kg except for V4-V2-g4pFc, which was undetectable after 24 hrs circulation in vivo. Without wishing to be bound by theory, it is thought that these results may indicate that the difference in efficacy among h15A7H and tetravalent variants could be mainly due to the differences in apoptosis-inducing ability, as demonstrated in Table B.

TABLE D

Plasma concentrations of h15A7H and h15A7H tetravalent antibodies in B6 mice.

| | Exp. 1 | Exp. 2 | Exp. 3 | Exp. 4 | Mean | SEM |
|---|---|---|---|---|---|---|
| Conc.(ng/mL) at 10 mg/kg | | | | | | |
| h15A7H | 103411 | 100189 | 104471 | 110820 | 104723 | 2227 |
| Conc.(ng/mL) at 1 mg/kg | | | | | | |
| h15A7H | 9087 | 8578 | 8316 | 10118 | 9025 | 398 |
| h15A7H LH10-g4pFc | 5698 | 7333 | 6335 | 6686 | 6513 | 508 |
| h15A7H V2-V3-g4pFc | 6488 | 8173 | 6982 | 6478 | 7030 | 576 |
| h15A7H scFv$_2$-LC-IgG4p | 5766 | 7082 | 7452 | 5979 | 6570 | 786 |
| h15A7H V4-V2-g4pFc | — | — | BLQ (<100) | BLQ (<100) | — | — |
| h15A7H scFv$_4$-crIgG4p | 6156 | 6924 | 5997 | 6353 | 6358 | 292 |
| h15A7H LC-scFv$_2$-IgG4p | 7323 | 8432 | 9014 | 9006 | 8444 | 535 |
| Conc. (ng/mL) at 0.3 mg/kg | | | | | | |
| h15A7H LH10-g4pFc | 1419 | 1853 | 1906 | 1793 | 1743 | 160 |
| h15A7H V2-V3-g4pFc | 1567 | 2284 | 2202 | 2065 | 2029 | 239 |
| h15A7H scFv$_2$-LC-IgG4p | 1344 | 1968 | 2112 | 1632 | 1764 | 241 |
| h15A7H V4-V2-g4pFc | — | — | BLQ (<100) | BLQ (<100) | — | — |
| h15A7H scFv$_4$-crIgG4p | 1256 | 1909 | 1772 | 1668 | 1651 | 205 |
| h15A7H LC-scFv$_2$-IgG4p | 1765 | 2493 | 2325 | 2356 | 2235 | 225 |

BLQ: beneath limit of quantification;
SEM: the standard error of the mean

In summary, these data demonstrate that various h15A7H tetravalent antibodies possess differential abilities in induction of apoptosis in vitro, which correlate with differential abilities in the inhibition of a DTH response in trans vivo DTH murine model. Those tetravalent antibodies with higher potency for apoptosis induction showed enhanced efficacy compared to h15A7H in the trans-vivo DTH model. These results suggest that some of these h15A7H tetravalent variants may have potential advantages over h15A7H for further clinical development.

Although the foregoing embodiments have been described in some detail by way of illustration and example for purposes of clarity of understanding, the descriptions and examples should not be construed as limiting the scope of the present disclosure.

SEQUENCES

All polypeptide sequences are presented N-terminal to C-terminal unless otherwise noted. All polynucleotide sequences are presented 5' to 3' unless otherwise noted. The three CDRs in each chain are underlined, and the linker regions are shown in lower case letters.

Amino acid sequence of h15A7H LH10-g4pFc (SEQ ID NO: 1)

DIQMTQSPSSLSASVGDRVTITC<u>RSSQSIVHNDGNTYFE</u>WYQQKPGKAPKLLIY<u>KVSNRFS</u>GVPSRFSGSGSGTHFT
LTISSLQPEDFATYYC<u>FQGSYVPLT</u>FGQGTKVEIKggggsggggsEVQLVESGGGLVQPGGSLRLSCAASGFTFS<u>SF
GMHW</u>VRQAPGKGLEWVA<u>YINGGSSTIFYANAVKG</u>RFTISRDNAKNTLYLQMNSLRAEDTAVYYCAR<u>YASYGGGAMDY</u>
WGQGTLVTVSSggggsggggsggggsggggsggggsDIQMTQSPSSLSASVGDRVTITC<u>RSSQSIVHNDGNTYFE</u>WY
QQKPGKAPKLLIY<u>KVSNRFS</u>GVPSRFSGSGSGTHFTLTISSLQPEDFATYYC<u>FQGSYVPLT</u>FGQGTKVEIKggggsg
gggsEVQLVESGGGLVQPGGSLRLSCAASGFTFS<u>SFGMHW</u>VRQAPGKGLEWVA<u>YINGGSSTIFYANAVKG</u>RFTISRD
NAKNTLYLQMNSLRAEDTAVYYCAR<u>YASYGGGAMDY</u>WGQGTLVTVSSggggsaaaESKYGPPCPPCPAPEFLGGPSV
FLFPPKPKDTLMISRTPEVTCVVVDVSQEDPEVQFNWYVDGVEVHNAKTKPREEQFNSTYRVVSVLTVLHQDWLNGK
EYKCKVSNKGLPSSIEKTISKAKGQPREPQVYTLPPSQEEMTKNQVSLTCLVKGFYPSDIAVEWESNGQPENNYKTT
PPVLDSDGSFFLYSRLTVDKSRWQEGNVFSCSVMHEALHNHYTQKSLSLSLGK cDNA sequence of h15A7H LH10-g4pFc (SEQ ID NO: 2)

GACATTCAGATGACCCAATCTCCGAGCTCTTTGTCTGCGTCTGTAGGGGATAGGGTCACTATCACCTGC<u>AGATCTAG
TCAGAGCATTGTACATAATGATGGAAACACCTATTTTGAA</u>TGGTACCAACAGAAACCAGGAAAGGCACCCAAGCTTC
TCATCTATA<u>AAGTTTCCAATCGATTTTC</u>TGGTGTCCCATCCAGGTTTAGTGGCAGTGGGTCTGGGACACACTTCACC
CTCACCATCTCTTCTCTGCAGCCGGAGGATTTCGCAACCTATTACTGTTTT<u>CAAGGTTCATATGTTCCTCTCACG</u>TT
CGGTCAAGGCACCAAGGTGGAAATCAAAggtggaggcggttcaggcggaggtggctctGAAGTGCAACTGGTGGAGT
CTGGGGGAGGCTTAGTGCAGCCTGGAGGAAGCTTGAGACTCTCCTGTGCAGCCTCTGGATTCACTTTCAGT<u>AGCTTT
GGAATGCACT</u>GGGTTCGCCAGGCTCCAGGGAAGGGACTCGAGTGGGTCGCA<u>TACATTAATGGTGGCAGTAGTACCAT
CTTCTATGCAAACGCAGTGAAGGGC</u>CGATTCACCATCTCCAGAGATAATGCCAAGAACACCCTGTACCTGCAAATGA
ATTCTCTGAGGGCTGAGGACACGGCCGTGTATTACTGTGCAAGA<u>TATGCTAGTTACGGAGGGGGTGCTATGGACTAT</u>
TGGGGCCAAGGCACCCTGGTCACAGTCTCCTCAggtggaggcggttcaggcggaggtggctctggcggtggcggatc
cggaggcggaggttccggaggtggcggaagtGACATTCAGATGACCCAATCTCCGAGCTCTTTGTCTGCGTCTGTAG
GGGATAGGGTCACTATCACCTGC<u>AGATCTAGTCAGAGCATTGTACATAATGATGGAAACACCTATTTTGAA</u>TGGTAC
CAACAGAAACCAGGAAAGGCACCCAAGCTTCTCATCTATA<u>AAGTTTCCAATCGATTTTC</u>TGGTGTCCCATCCAGGTT
TAGTGGCAGTGGGTCTGGGACACACTTCACCCTCACCATCTCTTCTCTGCAGCCGGAGGATTTCGCAACCTATTACT
GTTTT<u>CAAGGTTCATATGTTCCTCTCACG</u>TTCGGTCAAGGCACCAAGGTGGAAATCAAAggtggaggcggttcaggc
ggaggtggctctGAAGTGCAACTGGTGGAGTCTGGGGGAGGCTTAGTGCAGCCTGGAGGAAGCTTGAGACTCTCCTG
TGCAGCCTCTGGATTCACTTTCAGT<u>AGCTTTGGAATGCACT</u>GGGTTCGCCAGGCTCCAGGGAAGGGACTCGAGTGGG
TCGCA<u>TACATTAATGGTGGCAGTAGTACCATCTTCTATGCAAACGCAGTGAAGGGC</u>CGATTCACCATCTCCAGAGAT
AATGCCAAGAACACCCTGTACCTGCAAATGAATTCTCTGAGGGCTGAGGACACGGCCGTGTATTACTGTGCAAGA<u>TA
TGCTAGTTACGGAGGGGGTGCTATGGACTAT</u>TGGGGCCAAGGCACCCTGGTCACAGTCTCCTCAggtggaggcggtt
ccgcggccgcaGAGTCCAAATATGGTCCCCCATGCCCACCATGCCCAGCACCTGAGTTCCTGGGGGGACCATCAGTC
TTCCTGTTCCCCCCAAAACCCAAGGACACTCTCATGATCTCCCGGACCCCTGAGGTCACGTGCGTGGTGGTGGACGT
GAGCCAGGAAGACCCCGAGGTCCAGTTCAACTGGTACGTGGATGGCGTGGAGGTGCATAATGCCAAGACAAAGCCGC
GGGAGGAGCAGTTCAACAGCACGTACCGTGTGGTCAGCGTCCTCACCGTCCTGCACCAGGACTGGCTGAACGGCAAG
GAGTACAAGTGCAAGGTCTCCAACAAAGGCCTCCCGTCCTCCATCGAGAAAACCATCTCCAAAGCCAAAGGGCAGCC
CCGAGAGCCACAGGTGTACACCCTGCCCCCATCCCAGGAGGAGATGACCAAGAACCAGGTCAGCCTGACCTGCCTGG
TCAAAGGCTTCTACCCCAGCGACATCGCCGTGGAGTGGGAGAGCAATGGGCAGCCGGAGAACAACTACAAGACCACG
CCTCCCGTGCTGGACTCCGACGGCTCCTTCTTCCTCTACAGCAGGCTAACCGTGGACAAGAGCAGGTGGCAGGAGGG
GAATGTCTTCATGCTCCGTGATGCATGAGGCTCTGCACAACCACTACACAGAAGAGCCTCTCCCTGTCTCTGG
GTAAATGA Amino acid sequence of h15A7H V2-V3-g4pFc (SEQ ID NO: 3)

EVQLVESGGGLVQPGGSLRLSCAASGFTFS<u>SFGMHW</u>VRQAPGKGLEWVA<u>YINGGSSTIFYANAVKG</u>RFTISRDNAKN
TLYLQMNSLRAEDTAVYYCAR<u>YASYGGGAMDY</u>WGQGTLVTVSSggggsggggsggggsggggsggggsDIQMTQSPS
SLSASVGDRVTITC<u>RSSQSIVHNDGNTYFE</u>WYQQKPGKAPKLLIY<u>KVSNRFS</u>GVPSRFSGSGSGTHFTLTISSLQPE
DFATYYC<u>FQGSYVPLT</u>FGCGTKVEIKastgsDIQMTQSPSSLSASVGDRVTITC<u>RSSQSIVHNDGNTYFE</u>WYQQKPG
KAPKLLIY<u>KVSNRFS</u>GVPSRFSGSGSGTHFTLTISSLQPEDFATYYC<u>FQGSYVPLT</u>FGQGTKVEIKggggsggggsg
gggsggggsggggsEVQLVESGGGLVQPGGSLRLSCAASGFTFS<u>SFGMHW</u>VRQAPGKGLEWVA<u>YINGGSSTIFYANA
VKG</u>RFTISRDNAKNTLYLQMNSLRAEDTAVYYCAR<u>YASYGGGAMDY</u>WGQGTLVTVSSggggsaaaESKYGPPCPPCP
APEFLGGPSVFLFPPKPKDTLMISRTPEVTCVVVDVSQEDPEVQFNWYVDGVEVHNAKTKPREEQFNSTYRVVSVLT
VLHQDWLNGKEYKCKVSNKGLPSSIEKTISKAKGQPREPQVYTLPPSQEEMTKNQVSLTCLVKGFYPSDIAVEWESN
GQPENNYKTTPPVLDSDGSFFLYSRLTVDKSRWQEGNVFSCSVMHEALHNHYTQKSLSLSLGK cDNA sequence of h15A7H V2-V3-g4pFc (SEQ ID NO: 4)

GAAGTGCAACTGGTGGAGTCTGGGGGAGGCTTAGTGCAGCCTGGAGGAAGCTTGAGACTCTCCTGTGCAGCCTCTGG
ATTCACTTTCAGT<u>AGCTTTGGAATGCACT</u>GGGTTCGCCAGGCTCCAGGGAAGGGTCTCGAGTGGGTCGCA<u>TACATTA
ATGGTGGCAGTAGTACCATCTTCTATGCAAACGCAGTGAAGGGC</u>CGATTCACCATCTCCAGAGATAATGCCAAGAAC
ACCCTGTACCTGCAAATGAATTCTCTGAGGGCTGAGGACACGGCCGTGTATTACTGTGCAAGA<u>TATGCTAGTTACGG
AGGGGGTGCTATGGACTAT</u>TGGGGCCAAGGCACCCTGGTCACAGTCTCCTCAggtggaggcggttcaggcggaggtg
gctctggcggtggcggatccggaggcggaggttccggaggtggcggaagtGACATTCAGATGACCCAATCTCCGAGC
TCTTTGTCTGCGTCTGTAGGGGATAGGGTCACTATCACCTGC<u>AGATCTAGTCAGAGCATTGTACATAATGATGGAAA
CACCTATTTTGAA</u>TGGTACCAACAGAAACCAGGAAAGGCACCCAAGCTTCTCATCTATA<u>AAGTTTCCAATCGATTTT
C</u>TGGTGTCCCATCCAGGTTTAGTGGCAGTGGGTCTGGGACACACTTCACCCTCACCATCTCTTCTCTGCAGCCGGAG
GATTTCGCAACCTATTACTGTTTT<u>CAAGGTTCATATGTTCCTCTCACG</u>TTCGGTTGTGGCACCAAGGTGGAAATCAA
AgcttcaaccggttcaGACATTCAGATGACCCAATCTCCGAGCTCTTTGTCTGCGTCTGTAGGGGATAGGGTCACTA
TCACCTGC<u>ACATCTACTCACACCATTCTACATAATCATCCAAACACCTATTTTCAAT</u>CCTACCAACAAACCAGGA
AAGGCACCCAAGCTTCTCATCTATA<u>AAGTTTCCAATCGATTTTC</u>TGGTGTCCCATCCAGGTTTAGTGGCAGTGGGTC
TGGGACACACTTCACCCTCACCATCTCTTCTCTGCAGCCGGAGGATTTCGCAACCTATTACTGTTTT<u>CAAGGTTCAT
ATGTTCCTCTCACG</u>TTCGGTCAAGGCACCAAGGTGGAAATCAAAggtggaggcggttcaggcggaggtggctctggc
ggtggcggatccggaggcggaggttccggaggtggcggaagtGAAGTGCAACTGGTGGAGTCTGGGGGAGGCTTAGT
GCAGCCTGGAGGAAGCTTGAGACTCTCCTGTGCAGCCTCTGGATTCACTTTCAGT<u>AGCTTTGGAATGCACT</u>GGGTTC
GCCAGGCTCCAGGGAAGGGACTCGAGTGGGTCGCA<u>TACATTAATGGTGGCAGTAGTACCATCTTCTATGCAAACGCA
GTGAAGGGC</u>CGATTCACCATCTCCAGAGATAATGCCAAGAACACCCTGTACCTGCAAATGAATTCTCTGAGGGCTGA
GGACACGGCCGTGTATTACTGTGCAAGA<u>TATGCTAGTTACGGAGGGGGTGCTATGGACTAT</u>TGGGGCCAAGGCACCC -continued TGGTCACAGTCTCCTCAggaggcggaggttccgcggccgcaGAGTCCAAATATGGTCCCCCATGCCCACCATGCCCA
GCACCTGAGTTCCTGGGGGGACCATCAGTCTTCCTGTTCCCCCCAAAACCCAAGGACACTCTCATGATCTCCCGGAC
CCCTGAGGTCACGTGCGTGGTGGTGGACGTGAGCCAGGAAGACCCCGAGGTCCAGTTCAACTGGTACGTGGATGGCG
TGGAGGTGCATAATGCCAAGACAAAGCCGCGGGAGGAGCAGTTCAACAGCACGTACCGTGTGGTCAGCGTCCTCACC
GTCCTGCACCAGGACTGGCTGAACGGCAAGGAGTACAAGTGCAAGGTCTCCAACAAAGGCCTCCCGTCCTCCATCGA
GAAAACCATCTCCAAAGCCAAAGGGCAGCCCCGAGAGCCACAGGTGTACACCCTGCCCCCATCCCAGGAGGAGATGA
CCAAGAACCAGGTCAGCCTGACCTGCCTGGTCAAAGGCTTCTACCCCAGCGACATCGCCGTGGAGTGGGAGAGCAAT
GGGCAGCCGGAGAACAACTACAAGACCACGCCTCCCGTGCTGGACTCCGACGGCTCCTTCTTCCTCTACAGCAGGCT
AACCGTGGACAAGAGCAGGTGGCAGGAGGGGAATGTCTTCTCATGCTCCGTGATGCATGAGGCTCTGCACAACCACT
ACACACAGAAGAGCCTCTCCCTGTCTCTGGGTAAATGA Amino acid sequence of h15A7H V4-V2-g4pFc
(SEQ ID NO: 5)
DIQMTQSPSSLSASVGDRVTITC<u>RSSQSIVHNDGNTYFE</u>WYQQKPGKAPKLLIY<u>KVSNRFS</u>GVPSRFSGSGSGTHFT
LTISSLQPEDFATYYC<u>FQGSYVPLT</u>FGCGTKVEIKggggsggggsggggsggggsggggsEVQLVESGGGLVQPGGS
LRLSCAASGFTFS<u>SFGMH</u>WVRQAPGKCLEWVA<u>YINGGSSTIFYANAVKG</u>RFTISRDNAKNTLYLQMNSLRAEDTAVY
YCAR<u>YASYGGGAMDY</u>WGQGTLVTVSSastgsEVQLVESGGGLVQPGGSLRLSCAASGFTFS<u>SFGMH</u>WVRQAPGKCLE
WVA<u>YINGGSSTIFYANAVKG</u>RFTISRDNAKNTLYLQMNSLRAEDTAVYYCAR<u>YASYGGGAMDY</u>WGQGTLVTVSSggg
gsggggsggggsggggsggggsDIQMTQSPSSLSASVGDRVTITC<u>RSSQSIVHNDGNTYFE</u>WYQQKPGKAPKLLIY<u>K
VSNRFS</u>GVPSRFSGSGSGTHFTLTISSLQPEDFATYYC<u>FQGSYVPLT</u>FGCGTKVEIKggggsaaaESKYGPPCPPCP
APEFLGGPSVFLFPPKPKDTLMISRTPEVTCVVVDVSQEDPEVQFNWYVDGVEVHNAKTKPREEQFNSTYRVVSVLT
VLHQDWLNGKEYKCKVSNKGLPSSIEKTISKAKGQPREPQVYTLPPSQEEMTKNQVSLTCLVKGFYPSDIAVEWESN
GQPENNYKTTPPVLDSDGSFFLYSRLTVDKSRWQEGNVFSCSVMHEALHNHYTQKSLSLSLGK cDNA sequence of h15A7H V4-V2-g4pFc
(SEQ ID NO: 6)
GACATTCAGATGACCCAATCTCCGAGCTCTTTGTCTGCGTCTGTAGGGGATAGGGTCACTATCACCTGC<u>AGATCTAG
TCAGAGCATTGTACATAATGATGGAAACACCTATTTTGAATGG</u>TACCAACAGAAACCAGGAAAGGCACCCAAGCTTC
TCATCTATA<u>AAGTTTCCAATCGATTTTCT</u>GGTGTCCCATCCAGGTTTAGTGGCAGTGGGTCTGGGACACACTTCACC
CTCACCATCTCTTCTCTGCAGCCGGAGGATTTCGCAACCTATTACTGT<u>TTTCAAGGTTCATATGTTCCTCTCAC</u>GTT
CGGTTGTGGCACCAAGGTGGAAATCAAAggtggaggcggttcaggcggaggtggctctggcggtggcggatccggag
gcggaggttccggaggtggcggaagtGAAGTGCAACTGGTGGAGTCTGGGGGAGGCTTAGTGCAGCCTGGAGGAAGC
TTGAGACTCTCCTGTGCAGCCTCTGGATTCACTTTCAGT<u>AGCTTTGGAATGCAC</u>TGGGTTCGCCAGGCTCCAGGGAA
GTGTCTCGAGTGGGTCGCA<u>TACATTAATGGTGGCAGTAGTACCATCTTCTATGCAAACGCAGTGAAGGGC</u>CGATTCA
CCATCTCCAGAGATAATGCCAAGAACACCCTGTACCTGCAAATGAATTCTCTGAGGGCTGAGGACACGGCCGTGTAT
TACTGTGCAAGA<u>TATGCTAGTTACGGAGGGGGTGCTATGGACTAT</u>TGGGGCCAAGGCACCCTGGTCACAGTCTCCTC
AgcttcaaccggttcaGAAGTGCAACTGGTGGAGTCTGGGGGAGGCTTAGTGCAGCCTGGAGGAAGCTTGAGACTCT
CCTGTGCAGCCTCTGGATTCACTTTCAGT<u>AGCTTTGGAATGCAC</u>TGGGTTCGCCAGGCTCCAGGGAAGTGTCTCGAG
TGGGTCGCA<u>TACATTAATGGTGGCAGTAGTACCATCTTCTATGCAAACGCAGTGAAGGGC</u>CGATTCACCATCTCCAG
AGATAATGCCAAGAACACCCTGTACCTGCAAATGAATTCTCTGAGGGCTGAGGACACGGCCGTGTATTACTGTGCAA
GA<u>TATGCTAGTTACGGAGGGGGTGCTATGGACTAT</u>TGGGGCCAAGGCACCCTGGTCACAGTCTCCTCAggtggaggc
ggttcaggcggaggtggctctggcggtggcggatccggaggcggaggttccggaggtggcggaagtGACATTCAGAT
GACCCAATCTCCGAGCTCTTTGTCTGCGTCTGTAGGGGATAGGGTCACTATCACCTGC<u>AGATCTAGTCAGAGCATTG
TACATAATGATGGAAACACCTATTTTGAATGG</u>TACCAACAGAAACCAGGAAAGGCACCCAAGCTTCTCATCTATA<u>AA
GTTTCCAATCGATTTTCT</u>GGTGTCCCATCCAGGTTTAGTGGCAGTGGGTCTGGGACACACTTCACCCTCACCATCTC
TTCTCTGCAGCCGGAGGATTTCGCAACCTATTACTGT<u>TTTCAAGGTTCATATGTTCCTCTCAC</u>GTTCGGTTGTGGCA
CCAAGGTGGAAATCAAAggaggcggaggttccgcggccgcaGAGTCCAAATATGGTCCCCCATGCCCACCATGCCCA
GCACCTGAGTTCCTGGGGGGACCATCAGTCTTCCTGTTCCCCCCAAAACCCAAGGACACTCTCATGATCTCCCGGAC
CCCTGAGGTCACGTGCGTGGTGGTGGACGTGAGCCAGGAAGACCCCGAGGTCCAGTTCAACTGGTACGTGGATGGCG
TGGAGGTGCATAATGCCAAGACAAAGCCGCGGGAGGAGCAGTTCAACAGCACGTACCGTGTGGTCAGCGTCCTCACC
GTCCTGCACCAGGACTGGCTGAACGGCAAGGAGTACAAGTGCAAGGTCTCCAACAAAGGCCTCCCGTCCTCCATCGA
GAAAACCATCTCCAAAGCCAAAGGGCAGCCCCGAGAGCCACAGGTGTACACCCTGCCCCCATCCCAGGAGGAGATGA
CCAAGAACCAGGTCAGCCTGACCTGCCTGGTCAAAGGCTTCTACCCCAGCGACATCGCCGTGGAGTGGGAGAGCAAT
GGGCAGCCGGAGAACAACTACAAGACCACGCCTCCCGTGCTGGACTCCGACGGCTCCTTCTTCCTCTACAGCAGGCT
AACCGTGGACAAGAGCAGGTGGCAGGAGGGGAATGTCTTCTCATGCTCCGTGATGCATGAGGCTCTGCACAACCACT
ACACACAGAAGAGCCTCTCCCTGTCTCTGGGTAAATGA Amino acid sequence of h15A7H scFv$_2$-LC-IgG4p Light chain
(SEQ ID NO: 7)
EVQLVESGGGLVQPGGSLRLSCAASGFTFS<u>SFGMH</u>WVRQAPGKCLEWVA<u>YINGGSSTIFYANAVKG</u>RFTISRDNAKN
TLYLQMNSLRAEDTAVY<u>YCARYASYGGGAMDY</u>WGQGTLVTVSSggggsggggsggggsggggsggggsDIQMTQSPS
SLSASVGDRVTITC<u>RSSQSIVHNDGNTYFE</u>WYQQKPGKAPKLLIY<u>KVSNRFS</u>GVPSRFSGSGSGTHFTLTISSLQPE
DFATYYC<u>FQGSYVPLT</u>FGCGTKVEIKastgsggggsDIQMTQSPSSLSASVGDRVTITC<u>RSSQSIVHNDGNTYFE</u>WY
QQKPGKAPKLLIY<u>KVSNRFS</u>GVPSRFSGSGSGTHFTLTISSLQPEDFATYYC<u>FQGSYVPLT</u>FGQGTKVEIKRTVAAP
SVFIFPPSDEQLKSGTASVVCLLNNFYPREAKVQWKVDNALQSGNSQESVTEQDSKDSTYSLSSTLTLSKADYEKHK
VYACEVTHQGLSSPVTKSFNRGEC cDNA sequence of h15A7H scFv$_2$-LC-IgG4p Light chain
(SEQ ID NO: 8)
GAAGTGCAACTGGTGGAGTCTGGGGGAGGCTTAGTGCAGCCTGGAGGAAGCTTGAGACTCTCCTGTGCAGCCTCTGG
ATTCACTTTCAGT<u>AGCTTTGGAATGCAC</u>TGGGTTCGCCAGGCTCCAGGGAAGTGTCTCGAGTGGGTCGCA<u>TACATTA
ATGGTGGCAGTAGTACCATCTTCTATGCAAACGCAGTGAAGGGC</u>CGATTCACCATCTCCAGAGATAATGCCAAGAAC
ACCCTGTACCTGCAAATGAATTCTCTGAGGGCTGAGGACACGGCCGTGTATTACTGTGCAAGA<u>TATGCTAGTTACGG
AGGGGGTGCTATGGACTAT</u>TGGGGCCAAGGCACCCTGGTCACAGTCTCCTCAggtggaggcggttcaggcggaggtg
gctctggcggtggcggatccggaggcggaggttccggaggtggcggaagtGACATTCAGATGACCCAATCTCCGAGC
TCTTTGTCTGCGTCTGTAGGGGATAGGGTCACTATCACCTGC<u>AGATCTAGTCAGAGCATTGTACATAATGATGGAAA
CACCTATTTTGAATGG</u>TACCAACAGAAACCAGGAAAGGCACCCAAGCTTCTCATCTATA<u>AAGTTTCCAATCGATTTT
CT</u>GGTGTCCCATCCAGGTTTAGTGGCAGTGGGTCTGGGACACACTTCACCCTCACCATCTCTTCTCTGCAGCCGGAG
GATTTCGCAACCTATTACTGT<u>TTTCAAGGTTCATATGTTCCTCTCAC</u>GTTCGGTTGTGGCACCAAGGTGGAAATCAA
AgcttcaaccggttcaggaggtggcggaagtGACATTCAGATGACCCAATCTCCGAGCTCTTTGTCTGCGTCTGTAG
GGGATAGGGTCACTATCACCTGC<u>AGATCTAGTCAGAGCATTGTACATAATGATGGAAACACCTATTTTGAATGG</u>TAC -continued CAACAGAAACCAGGAAAGGCACCCAAGCTTCTCATCTATAAAGTTTCCAATCGATTTTCTGGTGTCCCATCCAGGTT
TAGTGGCAGTGGGTCTGGGACACACTTCACCCTCACCATCTCTTCTGCAGCCGGAGGATTTCGCAACCTATTACT
GTTTTCAAGGTTCATATGTTCCTCTCACGTTCGGTCAAGGCACCAAGGTGGAAATCAAACGAACTGTGGCTGCACCA
TCTGTCTTCATCTTCCCGCCATCTGATGAGCAGTTGAAATCTGGAACTGCCTCTGTTGTGTGCCTGCTGAATAACTT
CTATCCCAGAGAGGCCAAAGTACAGTGGAAGGTGGATAACGCCCTCCAATGGGTAACTCCCAGGAGAGTGTCACAG
AGCAGGACAGCAAGGACAGCACCTACAGCCTCAGCAGCACCCTGACGCTGAGCAAAGCAGACTACGAGAAACACAAA
GTCTACGCCTGCGAAGTCACCCATCAGGGCCTGAGCTCGCCCGTCACAAAGAGCTTCAACAGGGGAGAGTGTTAG Amino acid sequence of h15A7H LC-scFv$_2$-IgG4p light chain
(SEQ ID NO: 9)
DIQMTQSPSSLSASVGDRVTITC<u>RSSQSIVHNDGNTYFE</u>WYQQKPGKAPKLLIY<u>KVSNRFS</u>GVPSRFSGSGSGTHFT
LTISSLQPEDFATYYC<u>FQGSYVPLT</u>FGQGTKVEIKRTVAAPSVFIFPPSDEQLKSGTASVVCLLNNFYPREAKVQWK
VDNALQSGNSQESVTEQDSKDSTYSLSSTLTLSKADYEKHKVYACEVTHQGLSSPVTKSFNRGECggggsggggsEV
QLVESGGGLVQPGGSLRLSCAASGFTFS<u>SFGMH</u>WVRQAPGKCLEWVA<u>YINGGSSTIFYANAVKG</u>RFTISRDNAKNTL
YLQMNSLRAEDTAVYYCAR<u>YASYGGGAMDY</u>WGQGTLVTVSSggggsggggsggggsggggsggggsDIQMTQSPSSL
SASVGDRVTITC<u>RSSQSIVHNDGNTYFE</u>WYQQKPGKAPKLLIY<u>KVSNRFS</u>GVPSRFSGSGSGTHFTLTISSLQPEDF
ATYYC<u>FQGSYVPLT</u>FGCGTKVEIKAAAHHHHHHHHH cDNA sequence of h15A7H LC-scFv$_2$-IgG4p light chain
(SEQ ID NO: 10)
GACATTCAGATGACCCAATCTCCGAGCTCTTTGTCTGCGTCTGTAGGGGATAGGGTCACTATCACCTGC<u>AGATCTAG
TCAGAGCATTGTACATAATGATGGAAACACCTATTTTGAA</u>TGGTACCAACAGAAACCAGGAAAGGCACCCAAGCTTC
TCATCTAT<u>AAAGTTTCCAATCGATTTTCT</u>GGTGTCCCATCCAGGTTTAGTGGCAGTGGGTCTGGGACACACTTCACC
CTCACCATCTCTTCTGCAGCCGGAGGATTTCGCAACCTATTACTGTTTTCAAGGTTCATATGTTCCTCTCACGTT
CGGTCAAGGCACCAAGGTGGAAATCAAACGAACTGTGGCTGCACCATCTGTCTTCATCTTCCCGCCATCTGATGAGC
AGTTGAAATCTGGAACTGCCTCTGTTGTGTGCCTGCTGAATAACTTCTATCCCAGAGAGGCCAAAGTACAGTGGAAG
GTGGATAACGCCCTCCAATGGGTAACTCCCAGGAGAGTGTCACAGAGCAGGACAGCAAGGACAGCACCTACAGCCT
CAGCAGCACCCTGACGCTGAGCAAAGCAGACTACGAGAAACACAAAGTCTACGCCTGCGAAGTCACCCATCAGGGCC
TGAGCTCGCCCGTCACAAAGAGCTTCAACAGGGGAGAGTGTggtgg<u>aggcggttcaggcggaggtggctct</u>GAAGTG
CAACTGGTGGAGTCTGGGGGAGGCTTAGTGCAGCCTGGAGGAAGCTTGAGACTCTCCTGTGCAGCCTCTGGATTCAC
TTTCAGT<u>AGCTTTGGAATGCAC</u>TGGGTTCGCCAGGCTCCAGGGAAGGTGTCTCGAGTGGGTCGCA<u>TACATTAATGGT
GCAGTAGTACCATCTTCTATGCAAACGCAGTGAAGG</u>GCCGATTCACCATCTCCAGAGATAATGCCAAGAACACCCTG
TACCTGCAAATGAATTCTCTGAGGGCTGAGGACACGGCCGTGTATTACTGTGCAAGA<u>TATGCTAGTTACGGAGGGGG
TGCTATGGACTAT</u>TGGGGCCAAGGCACCCTGGTCACAGTCTCCTCAggtggaggcggttcaggcggaggtggctctg
gcggtggcggatccggaggcggaggttccggaggtggcggaagtGACATTCAGATGACCCAATCTCCGAGCTCTTTG
TCTGCGTCTGTAGGGGATAGGGTCACTATCACCTGC<u>AGATCTAGTCAGAGCATTGTACATAATGATGGAAACACCTA
TTTTGAA</u>TGGTACCAACAGAAACCAGGAAAGGCACCC<u>AAGCTT</u>CTCATCTAT<u>AAAGTTTCCAATCGATTTTCT</u>GGTG
TCCCATCCAGGTTTAGTGGCAGTGGGTCTGGGACACACTTCACCCTCACCATCTCTTCTGCAGCCGGAGGATTTC
GCAACCTATTACTGT<u>TTTCAAGGTTCATATGTTCCTCTCACG</u>TTCGGTTGTGGCACCAAGGTGGAAATCAAAGCGGC
CGCACATCATCATCATCATCACCACCACCACTAG Amino acid sequence of h15A7H scFv$_2$-LC-IgG4p and h15A7 LC-ScFv$_2$-IgG4p heavy chain
(SEQ ID NO: 11)
EVQLVESGGGLVQPGGSLRLSCAASGFTFS<u>SFGMH</u>WVRQAPGKGLEWVA<u>YINGGSSTIFYANAVKG</u>RFTISRDNAKN
TLYLQMNSLRAEDTAVYYCAR<u>YASYGGGAMDY</u>WGQGTLVTVSSASTKGPSVFPLAPCSRSTSESTAALGCLVKDYFP
EPVTVSWNSGALTSGVHTFPAVLQSSGLYSLSSVVTVPSSSLGTKTYTCNVDHKPSNTKVDKRVESKYGPPCPPCPA
PEFLGGPSVFLFPPKPKDTLMISRTPEVTCVVVDVSQEDPEVQFNWYVDGVEVHNAKTKPREEQFNSTYRVVSVLTV
LHQDWLNGKEYKCKVSNKGLPSSIEKTISKAKGQPREPQVYTLPPSQEEMTKNQVSLTCLVKGFYPSDIAVEWESNG
QPENNYKTTPPVLDSDGSFFLYSRLTVDKSRWQEGNVFSCSVMHEALHNHYTQKSLSLSLGK cDNA sequence of h15A7H scFv$_2$-LC-IgG4p and h15A7 LC-scFv$_2$-IgG4p heavy chain
(SEQ ID NO: 12)
GAAGTGCAACTGGTGGAGTCTGGGGGAGGCTTAGTGCAGCCTGGAGGAAGCTTGAGACTCTCCTGTGCAGCCTCTGG
ATTCACTTTCAGT<u>AGCTTTGGAATGCAC</u>TGGGTTCGCCAGGCTCCAGGGAAGGGACTCGAGTGGGTCGCA<u>TACATTA
ATGGTGCAGTAGTACCATCTTCTATGCAAACGCAGTGAAGG</u>GCCGATTCACCATCTCCAGAGATAATGCCAAGAAC
ACCCTGTACCTGCAAATGAATTCTCTGAGGGCTGAGGACACGGCCGTGTATTACTGTGCAAGA<u>TATGCTAGTTACGG
AGGGGGTGCTATGGACTAT</u>TGGGGCCAAGGCACCCTGGTCACAGTCTCCTCAGCTTCCACCAAGGGCCCATCCGTCT
TCCCCCTGGCGCCCTGCTCCAGGAGCACCTCCGAGAGCACAGCCGCCCTGGGCTGCCTGGTCAAGGACTACTTCCCC
GAACCGGTGACGGTGTCGTGGAACTCAGGCGCCCTGACCAGCGGCGTGCACACCTTCCCGGCTGTCCTACAGTCCTC
AGGACTCTACTCCCTCAGCAGCGTGGTGACCGTGCCCTCCAGCAGCTTGGGCACGAAGACCTACACCTGCAACGTAG
ATCACAAGCCCAGCAACACCAAGGTGGACAAGAGAGTTGAGTCCAAATATGGTCCCCCATGCCCACCATGCCCAGCA
CCTGAGTTCCTGGGGGGACCATCAGTCTTCCTGTTCCCCCCAAAACCCAAGGACACTCTCATGATCTCCCGGACCCC
TGAGGTCACGTGCGTGGTGGTGGACGTGAGCCAGGAAGACCCCGAGGTCCAGTTCAACTGGTACGTGGATGGCGTGG
AGGTGCATAATGCCAAGACAAAGCCGCGGGAGGAGCAGTTCAACAGCACGTACCGTGTGGTCAGCGTCCTCACCGTC
CTGCACCAGGACTGGCTGAACGGCAAGGAGTACAAGTGCAAGGTCTCCAACAAAGGCCTCCCGTCCTCCATCGAGAA
AACCATCTCCAAAGCCAAAGGGCAGCCCCGAGAGCCACAGGTGTACACCCTGCCCCCATCCCAGGAGGAGATGACCA
AGAACCAGGTCAGCCTGACCTGCCTGGTCAAAGGCTTCTACCCCAGCGACATCGCCGTGGAGTGGGAGAGCAATGGG
CAGCCGGAGAACAACTACAAGACCACGCCTCCCGTGCTGGACTCCGACGGCTCCTTCTTCCTCTACAGCAGGCTAAC
CGTGGACAAGAGCAGGTGGCAGGAGGGGAATGTCTTCTCATGCTCCGTGATGCATGAGGCTCTGCACAACCACTACA
CACAGAAGAGCCTCTCCCTGTCTCTGGGTAAATGA Amino acid sequence of h15A7H scFv$_4$-crIgG4p light chain
(SEQ ID NO: 13)
EVQLVESGGGLVQPGGSLRLSCAASGFTFS<u>SFGMH</u>WVRQAPGKCLEWVA<u>YINGGSSTIFYANAVKG</u>RFTISRDNAKN
TLYLQMNSLRAEDTAVYYCAR<u>YASYGGGAMDY</u>WGQGTLVTVSSggggsggggsggggsggggsggggsDIQMTQSPS
SLSASVGDRVTITC<u>RSSQSIVHNDGNTYFE</u>WYQQKPGKAPKLLIY<u>KVSNRFS</u>GVPSRFSGSGSGTHFTLTISSLQPE
DFATYYC<u>FQGSYVPLT</u>FGCGTKVEIKRTVAAPSVFIFPPSDEQLKSGTASVVCLLNNFYPREAKVQWKVDNALQSGN
SQESVTEQDSKDSTYSLSSTLTLSKADYEKHKVYACEVTHQGLSSPVTKSFNRGEC cDNA sequence of h15A7H scFv$_4$-crIgG4p light chain
(SEQ ID NO: 14)

-continued

```
GAAGTGCAACTGGTGGAGTCTGGGGGAGGCTTAGTGCAGCCTGGAGGAAGCTTGAGACTCTCCTGTGCAGCCTCTGG
ATTCACTTTCAGTAGCTTTGGAATGCACTGGGTTCGCCAGGCTCCAGGGAAGTGTCTCGAGTGGGTCGCATACATTA
ATGGTGGCAGTAGTACCATCTTCTATGCAAACGCAGTGAAGGGCCGATTCACCATCTCCAGAGATAATGCCAAGAAC
ACCCTGTACCTGCAAATGAATTCTCTGAGGGCTGAGGACACGGCCGTGTATTACTGTGCAAGATATGCTAGTTACGG
AGGGGGTGCTATGGACTATTGGGGCCAAGGCACCCTGGTCACAGTCTCCTCAggtggaggcggttcaggcggaggtg
gctctggcggtggcggatccggaggcggaggttccggaggtggcggaagtGACATTCAGATGACCCAATCTCCGAGC
TCTTTGTCTGCGTCTGTAGGGGATAGGGTCACTATCACCTGCAGATCTAGTCAGAGCATTGTACATAATGATGGAAA
CACCTATTTTGAATGGTACCAACAGAAACCAGGAAAGGCACCCAAGCTTCTCATCTATAAAGTTTCCAATCGATTTT
CTGGTGTCCCATCCAGGTTTAGTGGCAGTGGGTCTGGGACACACTTCACCCTCACCATCTCTTCTCTGCAGCCGGAG
GATTTCGCAACCTATTACTGTTTTCAAGGTTCATATGTTCCTCTCACGTTCGGTTGTGGCACCAAGGTGGAAATCAA
ACGAACTGTGGCTGCACCATCTGTCTTCATCTTCCCGCCATCTGATGAGCAGTTGAAATCTGGAACTGCCTCTGTTG
TGTGCCTGCTGAATAACTTCTATCCCAGAGAGGCCAAAGTACAGTGGAAGGTGGATAACGCCCTCCAATCGGGTAAC
TCCCAGGAGAGTGTCACAGAGCAGGACAGCAAGGACAGCACCTACAGCCTCAGCAGCACCCTGACGCTGAGCAAAGC
AGACTACGAGAAACACAAAGTCTACGCCTGCGAAGTCACCCATCAGGGCCTGAGCTCGCCCGTCACAAAGAGCTTCA
ACAGGGGAGAGTGTTAG
```

Amino acid sequence of h15A7H scFv$_4$-crIgG4p heavy chain
(SEQ ID NO: 15)

```
EVQLVESGGGLVQPGGSLRLSCAASGFTFSSFGMHWVRQAPGKCLEWVAYINGGSSTIFYANAVKGRFTISRDNAKN
TLYLQMNSLRAEDTAVYYCARYASYGGGAMDYWGQGTLVTVSSggggsggggsggggsggggsggggsDIQMTQSPS
SLSASVGDRVTITCRSSQSIVHNDGNTYFEWYQQKPGKAPKLLIYKVSNRFSGVPSRFSGSGSGTHFTLTISSLQPE
DFATYYCFQGSYVPLTFGCGTKVEIKASTKGPSVFPLAPCSRSTSESTAALGCLVKDYFPEPVTVSWNSGALTSGVH
TFPAVLQSSGLYSLSSVVTVPSSSLGTKTYTCNVDHKPSNTKVDKRVESKYGPPCPPCPAPEFLGGPSVFLFPPKPK
DTLMISRTPEVTCVVVDVSQEDPEVQFNWYVDGVEVHNAKTKPREEQFNSTYRVVSVLTVLHQDWLNGKEYKCKVSN
KGLPSSIEKTISKAKGQPREPQVYTLPPSQEEMTKNQVSLTCLVKGFYPSDIAVEWESNGQPENNYKTTPPVLDSDG
SFFLYSRLTVDKSRWQEGNVFSCSVMHEALHNHYTQKSLSLSLGK
``` cDNA sequence of h15A7H scFv$_4$-crIgG4p heavy chain
(SEQ ID NO: 16)

```
GAAGTGCAACTGGTGGAGTCTGGGGGAGGCTTAGTGCAGCCTGGAGGAAGCTTGAGACTCTCCTGTGCAGCCTCTGG
ATTCACTTTCAGTAGCTTTGGAATGCACTGGGTTCGCCAGGCTCCAGGGAAGTGTCTCGAGTGGGTCGCATACATTA
ATGGTGGCAGTAGTACCATCTTCTATGCAAACGCAGTGAAGGGCCGATTCACCATCTCCAGAGATAATGCCAAGAAC
ACCCTGTACCTGCAAATGAATTCTCTGAGGGCTGAGGACACGGCCGTGTATTACTGTGCAAGATATGCTAGTTACGG
AGGGGGTGCTATGGACTATTGGGGCCAAGGCACCCTGGTCACAGTCTCCTCAggtggaggcggttcaggcggaggtg
gctctggcggtggcggatccggaggcggaggttccggaggtggcggaagtGACATTCAGATGACCCAATCTCCGAGC
TCTTTGTCTGCGTCTGTAGGGGATAGGGTCACTATCACCTGCAGATCTAGTCAGAGCATTGTACATAATGATGGAAA
CACCTATTTTGAATGGTACCAACAGAAACCAGGAAAGGCACCCAAGCTTCTCATCTATAAAGTTTCCAATCGATTTT
CTGGTGTCCCATCCAGGTTTAGTGGCAGTGGGTCTGGGACACACTTCACCCTCACCATCTCTTCTCTGCAGCCGGAG
GATTTCGCAACCTATTACTGTTTTCAAGGTTCATATGTTCCTCTCACGTTCGGTTGTGGCACCAAGGTGGAAATCAA
AGCTTCCACCAAGGGCCCATCCGTCTTCCCCCTGGCGCCCTGCTCCAGGAGCACCTCCGAGAGCACAGCCGCCCTGG
GCTGCCTGGTCAAGGACTACTTCCCCGAACCGGTGACGGTGTCGTGGAACTCAGGCGCCCTGACCAGCGGCGTGCAC
ACCTTCCCGGCTGTCCTACAGTCCTCAGGACTCTACTCCCTCAGCAGCGTGGTGACCGTGCCCTCCAGCAGCTTGGG
CACGAAGACCTACACCTGCAACGTAGATCACAAGCCCAGCAACACCAAGGTGGACAAGAGAGTTGAGTCCAAATATG
GTCCCCCATGCCCACCATGCCCAGCACCTGAGTTCCTGGGGGGACCATCAGTCTTCCTGTTCCCCCCAAAACCCAAG
GACACTCTCATGATCTCCCGGACCCCTGAGGTCACGTGCGTGGTGGTGGACGTGAGCCAGGAAGACCCCGAGGTCCA
GTTCAACTGGTACGTGGATGGCGTGGAGGTGCATAATGCCAAGACAAAGCCGCGGGAGGAGCAGTTCAACAGCACGT
ACCGTGTGGTCAGCGTCCTCACCGTCCTGCACCAGGACTGGCTGAACGGCAAGGAGTACAAGTGCAAGGTCTCCAAC
AAAGGCCTCCCGTCCTCCATCGAGAAAACCATCTCCAAAGCCAAAGGGCAGCCCCGAGAGCCACAGGTGTACACCCT
GCCCCCATCCCAGGAGGAGATGACCAAGAACCAGGTCAGCCTGACCTGCCTGGTCAAAGGCTTCTACCCCAGCGACA
TCGCCGTGGAGTGGGAGAGCAATGGGCAGCCGGAGAACAACTACAAGACCACGCCTCCCGTGCTGGACTCCGACGGC
TCCTTCTTCCTCTACAGCAGGCTAACCGTGGACAAGAGCAGGTGGCAGGAGGGGAATGTCTTCTCATGCTCCGTGAT
GCATGAGGCTCTGCACAACCACTACACACAGAAGAGCCTCTCCCTGTCTCTGGGTAAATGA
```

Amino acid sequence of h15A7H CDR-H1
(SEQ ID NO: 17)

SFGMH

Amino acid sequence of h15A7H CDR-H2
(SEQ ID NO: 18)

YINGGSSTIFYANAVKG

Amino acid sequence of h15A7H CDR-H3
(SEQ ID NO: 19)

YASYGGGAMDY

Amino acid sequence of h15A7H CDR-L1
(SEQ ID NO: 20)

RSSQSIVHNDGNTYFE

Amino acid sequence of h15A7H CDR-L2
(SEQ ID NO: 21)

KVSNRFS

Amino acid sequence of h15A7H CDR-L3
(SEQ ID NO: 22)

FQGSYVPLT

Amino acid sequence of h15A7H VH
(SEQ ID NO: 23)

```
EVQLVESGGGLVQPGGSLRLSCAASGFTESSFGMHWVRQAPGKGLEWVAYINGGSSTIFYANAVKGRFTISRDNAKN
TLYLQMNSLRAEDTAVYYCARYASYGGGAMDYWGQGTLVTVSS
```

-continued

Amino acid sequence of h15A7H VL
(SEQ ID NO: 24)
DIQMTQSPSSLSASVGDRVTITCRSSQSIVHNDGNTYFEWYQQKPGKAPKLLIYKVSNRFSGVPSRFSGSGSGTHFT
LTISSLQPEDFATYYCFQGSYVPLTFGQGTKVEIK Amino acid sequence of linker sequence repeat
(SEQ ID NO: 25)
ggggs Amino acid sequence of linker with Fc
(SEQ ID NO: 26)
ggggsaaa Amino acid sequence of taFv linker
(SEQ ID NO: 27)
astgs Amino acid sequence of scFv light chain linker
(SEQ ID NO: 28)
astgsggggs Amino acid sequence of h15A7H VH G44C
(SEQ ID NO: 29)
EVQLVESGGGLVQPGGSLRLSCAASGFTESSFGMHWVRQAPGKCLEWVAYINGGSSTIFYANAVKGRFTISRDNAKN
TLYLQMNSLRAEDTAVYYCARYASYGGGAMDYWGQGTLVTVSS Amino acid sequence of h15A7H VL Q100C
(SEQ ID NO: 30)
DIQMTQSPSSLSASVGDRVTITCRSSQSIVHNDGNTYFEWYQQKPGKAPKLLIYKVSNRFSGVPSRFSGSGSGTHFT
LTISSLQPEDFATYYCFQGSYVPLTFGCGTKVEIK Amino acid sequence of human PSGL-1
(SEQ ID NO: 31)
MPLQLLLLLILLGPGNSLQLWDTWADEAEKALGPLLARDRRQATEYEYLDYDFLPETEPPEMLRNSTDTT
PLTGPGTPESTTVEPAARRSTGLDAGGAVTELTTELANMGNLSTDSAAMEIQTTQPAATEAQTTQPVPTE
AQTTPLAATEAQTTRLTATEAQTTPLAATEAQTTPPAATEAQTTQPTGLEAQTTAPAAMEAQTTAPAAME
AQTTPPAAMEAQTTQTTAMEAQTTAPEATEAQTTQPTATEAQTTPLAAMEALSTEPSATEALSMEPTTKR
GLFIPFSVSSVTHKGIPMAASNLSVNYPVGAPDHISVKQCLLAILILALVATIFFVCTVVLAVRLSRKGH
MYPVRNYSPTEMVCISSLLPDGGEGPSATANGGLSKAKSPGLTPEPREDREGDDLTLHSFLP Amino acid sequence of shorter human PSGL-1 variant
(SEQ ID NO: 32)
MPLQLLLLLILLGPGNSLQLWDTWADEAEKALGPLLARDRRQATEYEYLDYDFLPETEPPEMLRNSTDTT
PLTGPGTPESTTVEPAARRSTGLDAGGAVTELTTELANMGNLSTDSAAMEIQTTQPAATEAQTTPLAATE
AQTTRLTATEAQTTPLAATEAQTTPPAATEAQTTQPTGLEAQTTAPAAMEAQTTAPAAMEAQTTPPAAME
AQTTQTTAMEAQTTAPEATEAQTTQPTATEAQTTPLAAMEALSTEPSATEALSMEPTTKRGLFIPFSVSS
VTHKGIPMAASNLSVNYPVGAPDHISVKQCLLAILILALVATIFFVCTVVLAVRLSRKGHMYPVRNYSPT
EMVCISSLLPDGGEGPSATANGGLSKAKSPGLTPEPREDREGDDLTLHSFLP

---

What is claimed is:

1. A tetravalent antibody that specifically binds to human PSGL-1, the tetravalent antibody comprising a dimer of two monomers, wherein each monomer of the dimer comprises a single-chain polypeptide comprising, from N-terminus to C-terminus:
   (a) a first light chain variable (VL) domain;
   (b) a first linker sequence, wherein the first linker sequence has 5-12 amino acids;
   (c) a first heavy chain variable (VH) domain;
   (d) a second linker sequence, wherein the second linker sequence has two, three, four, or five repeats of the amino acid sequence of GGGGS (SEQ ID NO:25);
   (e) a second VL domain;
   (f) a third linker sequence, wherein the third linker sequence has 5-12 amino acids;
   (g) a second VH domain;
   (h) a fourth linker sequence, wherein the fourth linker sequence has 5-12 amino acids; and
   (i) an antibody Fc domain,
wherein each of the first and the second VL domains comprises (i) a CDR-L1 comprising the amino acid sequence of SEQ ID NO:20; (ii) a CDR-L2 comprising the amino acid sequence of SEQ ID NO:21; and (iii) a CDR-L3 comprising the amino acid sequence of SEQ ID NO:22; wherein each of the first and the second VH domains comprises (i) a CDR-H1 comprising the amino acid sequence of SEQ ID NO:17; (ii) a CDR-H2 comprising the amino acid sequence of SEQ ID NO:18; and (iii) a CDR-H3 comprising the amino acid sequence of SEQ ID NO:19; wherein the first VL domain forms a VH-VL binding unit with the second VH domain, and the first VH domain forms a VH-VL binding unit with the second VL domain; and wherein each of the two VH-VL binding units is specific for human PSGL-1.

2. The tetravalent antibody of claim 1, wherein each of the two VH domains comprises the amino acid sequence of SEQ ID NO:23.

3. The tetravalent antibody of claim 1, wherein each of the two VH domains comprises the amino acid sequence of SEQ ID NO:29.

4. The tetravalent antibody of claim 1, wherein each of the two VL domains comprises the amino acid sequence of SEQ ID NO:24.

5. The tetravalent antibody of claim 1, wherein each of the two VL domains comprises the amino acid sequence of SEQ ID NO:30.

6. The tetravalent antibody of claim 1, wherein the first and the third linker sequences both have two repeats of SEQ ID NO:25.

7. The tetravalent antibody of claim 1, wherein the second linker sequence has five repeats of SEQ ID NO:25.

8. The tetravalent antibody of claim 1, wherein the fourth linker sequence has the amino acid sequence of SEQ ID NO:26.

9. The tetravalent antibody of claim 1, wherein each of the two single-chain polypeptides comprises the amino acid sequence of SEQ ID NO:1.

10. The tetravalent antibody of claim 9, wherein each of the two single-chain polypeptides is encoded by a polynucleotide comprising the polynucleotide sequence of SEQ ID NO:2.

11. A tetravalent antibody that specifically binds to human PSGL-1, the tetravalent antibody comprising a dimer of two monomers, wherein each monomer of the dimer comprises a single-chain polypeptide comprising, from N-terminus to C-terminus:
   (a) a first heavy chain variable (VH) domain;
   (b) a first linker sequence, wherein the first linker sequence has two, three, four, or five repeats of the amino acid sequence of GGGGS (SEQ ID NO:25);
   (c) a first light chain variable (VL) domain;
   (d) a second linker sequence, wherein the second linker sequence has 5-12 amino acids;
   (e) a second VL domain;
   (f) a third linker sequence, wherein the third linker sequence has two, three, four, or five repeats of the amino acid sequence of GGGGS (SEQ ID NO:25);
   (g) a second VH domain;
   (h) a fourth linker sequence, wherein the fourth linker sequence has 5-12 amino acids; and
   (i) an antibody Fc domain,
wherein each of the first and the second VL domains comprises (i) a CDR-L1 comprising the amino acid sequence of SEQ ID NO:20; (ii) a CDR-L2 comprising the amino acid sequence of SEQ ID NO:21; and (iii) a CDR-L3 comprising the amino acid sequence of SEQ ID NO:22; wherein each of the first and the second VH domains comprises (i) a CDR-H1 comprising the amino acid sequence of SEQ ID NO:17; (ii) a CDR-H2 comprising the amino acid sequence of SEQ ID NO:18; and (iii) a CDR-H3 comprising the amino acid sequence of SEQ ID NO:19; wherein each of the first and the second VL domains forms a VH-VL binding unit with a corresponding VH domain of the first and the second VH domains; and wherein each of the two VH-VL binding units is specific for human PSGL-1.

12. The tetravalent antibody of claim 11, wherein each of the two VH domains comprises the amino acid sequence of SEQ ID NO:23.

13. The tetravalent antibody of claim 11, wherein each of the two VH domains comprises the amino acid sequence of SEQ ID NO:29.

14. The tetravalent antibody of claim 11, wherein each of the two VL domains comprises the amino acid sequence of SEQ ID NO:24.

15. The tetravalent antibody of claim 11, wherein each of the two VL domains comprises the amino acid sequence of SEQ ID NO:30.

16. The tetravalent antibody of claim 11, wherein the first and the third linker sequences both have five repeats of SEQ ID NO:25.

17. The tetravalent antibody of claim 11, wherein the second linker sequence has the amino acid sequence of SEQ ID NO:27.

18. The tetravalent antibody of claim 11, wherein the fourth linker sequence has the amino acid sequence of SEQ ID NO:26.

19. The tetravalent antibody of claim 11, wherein each of the two single-chain polypeptides comprises the amino acid sequence of SEQ ID NO:3.

20. The tetravalent antibody of claim 19, wherein each of the two single-chain polypeptides is encoded by a polynucleotide comprising the polynucleotide sequence of SEQ ID NO:4.

21. A tetravalent antibody that specifically binds to human PSGL-1, the tetravalent antibody comprising a dimer of two monomers, wherein each monomer of the dimer comprises an antibody heavy chain and an antibody light chain;
  wherein the antibody light chain comprises, from N-terminus to C-terminus:
    (i) a first heavy chain variable (VH) domain,
    (ii) a first linker sequence, wherein the first linker sequence has two, three, four, or five repeats of the amino acid sequence of GGGGS (SEQ ID NO:25),
    (iii) a first light chain variable (VL) domain,
    (iv) a second linker sequence, wherein the second linker sequence has 5-12 amino acids,
    (v) a second VL domain, and
    (vi) a light chain constant (CL) domain;
  wherein the antibody heavy chain comprises:
    (i) a second VH domain, and
    (ii) a heavy chain constant region comprising a first heavy chain constant region (CH1) domain, an antibody hinge region, an second heavy chain constant region (CH2) domain, and a third heavy chain constant region (CH3) domain;
  wherein each of the first and the second VL domains comprises (i) a CDR-L1 comprising the amino acid sequence of SEQ ID NO:20; (ii) a CDR-L2 comprising the amino acid sequence of SEQ ID NO:21; and (iii) a CDR-L3 comprising the amino acid sequence of SEQ ID NO:22; wherein each of the first and the second VH domains comprises (i) a CDR-H1 comprising the amino acid sequence of SEQ ID NO:17; (ii) a CDR-H2 comprising the amino acid sequence of SEQ ID NO:18; and (iii) a CDR-H3 comprising the amino acid sequence of SEQ ID NO:19; wherein each of the first and the second VL domains forms a VH-VL binding unit with a corresponding VH domain of the first and the second VH domains; and wherein each of the two VH-VL binding units is specific for human PSGL-1.

22. The tetravalent antibody of claim 21, wherein the first and the second VH domains each comprise the amino acid sequence of SEQ ID NO:23.

23. The tetravalent antibody of claim 21, wherein the first and the second VH domains each comprise the amino acid sequence of SEQ ID NO:29.

24. The tetravalent antibody of claim 21, wherein the first and the second VL domains each comprise the amino acid sequence of SEQ ID NO:24.

25. The tetravalent antibody of claim 21, wherein the first and the second VL domains each comprise the amino acid sequence of SEQ ID NO:30.

26. The tetravalent antibody of claim 21, wherein the CL domain is a kappa CL domain.

27. The tetravalent antibody of claim 21, wherein the first linker sequence has five repeats of SEQ ID NO:25.

28. The tetravalent antibody of claim 21, wherein the second linker sequence has the amino acid sequence of SEQ ID NO:28.

29. The tetravalent antibody of claim 21, wherein the antibody light chain comprises the amino acid sequence of SEQ ID NO:7.

30. The tetravalent antibody of claim 29, wherein the antibody light chain is encoded by a polynucleotide comprising the polynucleotide sequence of SEQ ID NO:8.

31. The tetravalent antibody of claim 21, wherein the antibody heavy chain comprises the amino acid sequence of SEQ ID NO:11.

32. The tetravalent antibody of claim 31, wherein the antibody heavy chain is encoded by a polynucleotide comprising the polynucleotide sequence of SEQ ID NO:12.

33. The tetravalent antibody of claim 1, wherein the antibody Fc domain is a human antibody Fc domain.

34. The tetravalent antibody of claim 33, wherein the antibody Fc domain is a human IgG4 Fc domain.

35. The tetravalent antibody of claim 34, wherein the human IgG4 Fc domain comprises a hinge region sequence comprising one or more amino acid substitutions that result in reduced IgG4 shuffling, as compared to an IgG4 hinge region lacking the one or more amino acid substitutions.

36. The tetravalent antibody of claim 34, wherein the human IgG4 Fc domain comprises a hinge region sequence comprising a serine to proline substitution at amino acid 228, numbering according to EU index.

37. An isolated polynucleotide encoding the tetravalent antibody of claim 1.

38. The isolated polynucleotide of claim 37, wherein the isolated polynucleotide comprises the polynucleotide sequence of SEQ ID NO:2.

39. A vector comprising the isolated polynucleotide of claim 37.

40. An isolated host cell comprising the polynucleotide of claim 37.

41. A method of producing a tetravalent antibody comprising culturing the host cell of claim 40 so that the tetravalent antibody is produced.

42. The method of claim 41, further comprising recovering the tetravalent antibody from the host cell.

43. A pharmaceutical composition comprising the tetravalent antibody of claim 1 and a pharmaceutically acceptable carrier.

44. A kit comprising the tetravalent antibody of claim 1 and an optional pharmaceutically acceptable carrier.

45. A method of treating a T-cell mediated inflammatory disease, the method comprising administering to a subject in need thereof a therapeutically effective amount of the tetravalent antibody of claim 1.

46. A method for treating an individual in need of a transfusion or transplantation, comprising administering to the individual a therapeutically effective amount of the tetravalent antibody of claim 1 concurrently with or after the transfusion or transplantation.

47. The method of claim 45, wherein the T-cell mediated inflammatory disease is an autoimmune disease.

48. The method of claim 45, wherein the T-cell mediated inflammatory disease is selected from the group consisting of psoriasis, psoriatic arthritis, rheumatoid arthritis, Crohn's disease, ankylosing spondylitis, type I diabetes, ulcerative colitis, multiple sclerosis, allergy, atopic dermatitis, asthma, and graft versus host disease (GVHD).

49. The method of claim 48, wherein the psoriasis is plaque psoriasis, chronic plaque psoriasis, guttate psoriasis, inverse psoriasis, pustular psoriasis, or erythrodermic psoriasis.

50. The method of claim 46, wherein the transplantation is a transplantation of a tissue selected from the group consisting of bone marrow, kidney, heart, liver, neuronal tissue, lung, pancreas, skin, and intestine.

51. The method of claim 46, wherein the transfusion is a transfusion comprising one or more of white blood cells, red blood cells, and platelets.

52. The tetravalent antibody of claim 11, wherein the antibody Fc domain is a human IgG4 Fc domain.

53. The tetravalent antibody of claim 52, wherein the human IgG4 Fc domain comprises a hinge region sequence comprising a serine to proline substitution at amino acid 228, numbering according to EU index.

54. An isolated polynucleotide encoding the tetravalent antibody of claim 11.

55. The isolated polynucleotide of claim 54, wherein the isolated polynucleotide comprises the polynucleotide sequence of SEQ ID NO:4.

56. A vector comprising the isolated polynucleotide of claim 54.

57. An isolated host cell comprising the polynucleotide of claim 54.

58. A method of producing a tetravalent antibody comprising culturing the host cell of claim 57 so that the tetravalent antibody is produced.

59. The method of claim 58, further comprising recovering the tetravalent antibody from the host cell.

60. A pharmaceutical composition comprising the tetravalent antibody of claim 11 and a pharmaceutically acceptable carrier.

61. A kit comprising the tetravalent antibody of claim 11 and an optional pharmaceutically acceptable carrier.

62. A method of treating a T-cell mediated inflammatory disease, the method comprising administering to a subject in need thereof a therapeutically effective amount of the tetravalent antibody of claim 11.

63. A method for treating an individual in need of a transfusion or transplantation, comprising administering to the individual a therapeutically effective amount of the tetravalent antibody of claim 11 concurrently with or after the transfusion or transplantation.

64. The method of claim 62, wherein the T-cell mediated inflammatory disease is an autoimmune disease.

65. The method of claim 62, wherein the T-cell mediated inflammatory disease is selected from the group consisting of psoriasis, psoriatic arthritis, rheumatoid arthritis, Crohn's disease, ankylosing spondylitis, type I diabetes, ulcerative colitis, multiple sclerosis, allergy, atopic dermatitis, asthma, and graft versus host disease (GVHD).

66. The method of claim 65, wherein the psoriasis is plaque psoriasis, chronic plaque psoriasis, guttate psoriasis, inverse psoriasis, pustular psoriasis, or erythrodermic psoriasis.

67. The method of claim 63, wherein the transplantation is a transplantation of a tissue selected from the group consisting of bone marrow, kidney, heart, liver, neuronal tissue, lung, pancreas, skin, and intestine.

68. The method of claim 63, wherein the transfusion is a transfusion comprising one or more of white blood cells, red blood cells, and platelets.

69. The tetravalent antibody of claim 21, wherein the heavy chain constant region comprises a human IgG4 Fc domain.

70. The tetravalent antibody of claim 69, wherein the human IgG4 Fc domain comprises a hinge region sequence comprising a serine to proline substitution at amino acid 228, numbering according to EU index.

71. An isolated polynucleotide comprising the polynucleotide sequence of SEQ ID NO:8.

72. An isolated polynucleotide comprising the polynucleotide sequence of SEQ ID NO:12.

73. An isolated polynucleotide encoding the tetravalent antibody of claim 21, wherein the isolated polynucleotide comprises the polynucleotide sequence of SEQ ID NO:8 and the polynucleotide sequence of SEQ ID NO:12.

74. A vector comprising the isolated polynucleotide of claim 73.

75. An isolated host cell comprising the polynucleotide of claim 73.

76. A method of producing a tetravalent antibody comprising culturing the host cell of claim 75 so that the tetravalent antibody is produced.

77. The method of claim 76, further comprising recovering the tetravalent antibody from the host cell.

78. A pharmaceutical composition comprising the tetravalent antibody of claim 21 and a pharmaceutically acceptable carrier.

79. A kit comprising the tetravalent antibody of claim 21 and an optional pharmaceutically acceptable carrier.

80. A method of treating a T-cell mediated inflammatory disease, the method comprising administering to a subject in need thereof a therapeutically effective amount of the tetravalent antibody of claim 21.

81. A method for treating an individual in need of a transfusion or transplantation, comprising administering to the individual a therapeutically effective amount of the tetravalent antibody of claim 21 concurrently with or after the transfusion or transplantation.

82. The method of claim 80, wherein the T-cell mediated inflammatory disease is an autoimmune disease.

83. The method of claim 80, wherein the T-cell mediated inflammatory disease is selected from the group consisting of psoriasis, psoriatic arthritis, rheumatoid arthritis, Crohn's disease, ankylosing spondylitis, type I diabetes, ulcerative colitis, multiple sclerosis, allergy, atopic dermatitis, asthma, and graft versus host disease (GVHD).

84. The method of claim 83, wherein the psoriasis is plaque psoriasis, chronic plaque psoriasis, guttate psoriasis, inverse psoriasis, pustular psoriasis, or erythrodermic psoriasis.

85. The method of claim 81, wherein the transplantation is a transplantation of a tissue selected from the group consisting of bone marrow, kidney, heart, liver, neuronal tissue, lung, pancreas, skin, and intestine.

86. The method of claim 81, wherein the transfusion is a transfusion comprising one or more of white blood cells, red blood cells, and platelets.

87. A tetravalent antibody that specifically binds to human PSGL-1, the tetravalent antibody comprising a dimer of two monomers, wherein each monomer of the dimer comprises a single-chain polypeptide comprising, from N-terminus to C-terminus:
  (a) a first light chain variable (VL) domain;
  (b) a first linker sequence, wherein the first linker sequence has 5-12 amino acids;
  (c) a first heavy chain variable (VH) domain;
  (d) a second linker sequence, wherein the second linker sequence has two, three, four, or five repeats of the amino acid sequence of GGGGS (SEQ ID NO:25);
  (e) a second VL domain;
  (f) a third linker sequence, wherein the third linker sequence has 5-12 amino acids;
  (g) a second VH domain;
  (h) a fourth linker sequence, wherein the fourth linker sequence has 5-12 amino acids; and
  (i) an antibody Fc domain,
wherein each of the first and the second VL domains comprises an amino acid sequence having at least 90% sequence identity to SEQ ID NO:24 or SEQ ID NO:30; wherein each of the first and the second VH domains comprises an amino acid sequence having at least 90% sequence identity to SEQ ID NO:23 or SEQ ID NO:29; wherein the first VL domain forms a VH-VL binding unit with the second VH domain, and the first VH domain forms a VH-VL binding unit with the second VL domain; and wherein each of the two VH-VL binding units is specific for human PSGL-1.

88. The tetravalent antibody of claim 87, wherein the first and the second VL domains each comprise (i) a CDR-L1 comprising the amino acid sequence of SEQ ID NO:20; (ii) a CDR-L2 comprising the amino acid sequence of SEQ ID NO:21; and (iii) a CDR-L3 comprising the amino acid sequence of SEQ ID NO:22.

89. The tetravalent antibody of claim 87, wherein the first and the second VH domains each comprise (i) a CDR-H1 comprising the amino acid sequence of SEQ ID NO:17; (ii) a CDR-H2 comprising the amino acid sequence of SEQ ID NO:18; and (iii) a CDR-H3 comprising the amino acid sequence of SEQ ID NO:19.

90. The tetravalent antibody of claim 87, wherein the first and the third linker sequences both have two repeats of SEQ ID NO:25.

91. The tetravalent antibody of claim 87, wherein the second linker sequence has five repeats of SEQ ID NO:25.

92. The tetravalent antibody of claim 87, wherein the fourth linker sequence has the amino acid sequence of SEQ ID NO:26.

93. The tetravalent antibody of claim 87, wherein the antibody Fc domain is a human antibody Fc domain.

94. The tetravalent antibody of claim 93, wherein the antibody Fc domain is a human IgG4 Fc domain.

95. The tetravalent antibody of claim 94, wherein the human IgG4 Fc domain comprises a hinge region sequence comprising (a) one or more amino acid substitutions that result in reduced IgG4 shuffling, as compared to an IgG4 hinge region lacking the one or more amino acid substitutions, or (b) a serine to proline substitution at amino acid 228, numbering according to EU index.

96. An isolated polynucleotide encoding the tetravalent antibody of claim 87.

97. A vector comprising the isolated polynucleotide of claim 96.

98. An isolated host cell comprising the polynucleotide of claim 96.

99. A method of producing a tetravalent antibody comprising culturing the host cell of claim 98 so that the tetravalent antibody is produced.

100. A pharmaceutical composition comprising the tetravalent antibody of claim 87 and a pharmaceutically acceptable carrier.

101. A method of treating a T-cell mediated inflammatory disease, the method comprising administering to a subject in need thereof a therapeutically effective amount of the tetravalent antibody of claim 87.

102. The method of claim 101, wherein the T-cell mediated inflammatory disease is an autoimmune disease.

103. The method of claim 101, wherein the T-cell mediated inflammatory disease is selected from the group consisting of psoriasis, psoriatic arthritis, rheumatoid arthritis, Crohn's disease, ankylosing spondylitis, type I diabetes, ulcerative colitis, multiple sclerosis, allergy, atopic dermatitis, asthma, and graft versus host disease (GVHD).

104. A method for treating an individual in need of a transfusion or transplantation, comprising administering to the individual a therapeutically effective amount of the tetravalent antibody of claim 87 concurrently with or after the transfusion or transplantation.

105. The method of claim 104, wherein the transplantation is a transplantation of a tissue selected from the group consisting of bone marrow, kidney, heart, liver, neuronal tissue, lung, pancreas, skin, and intestine.

106. The method of claim 104, wherein the transfusion is a transfusion comprising one or more of white blood cells, red blood cells, and platelets.

107. A tetravalent antibody that specifically binds to human PSGL-1, the tetravalent antibody comprising a dimer of two monomers, wherein each monomer of the dimer comprises a single-chain polypeptide comprising, from N-terminus to C-terminus:

(a) a first heavy chain variable (VH) domain;
(b) a first linker sequence, wherein the first linker sequence has two, three, four, or five repeats of the amino acid sequence of GGGGS (SEQ ID NO:25);
(c) a first light chain variable (VL) domain;
(d) a second linker sequence, wherein the second linker sequence has 5-12 amino acids;
(e) a second VL domain;
(f) a third linker sequence, wherein the third linker sequence has two, three, four, or five repeats of the amino acid sequence of GGGGS (SEQ ID NO:25);
(g) a second VH domain;
(h) a fourth linker sequence, wherein the fourth linker sequence has 5-12 amino acids; and
(i) an antibody Fc domain,
wherein each of the first and the second VL domains comprises an amino acid sequence having at least 90% sequence identity to SEQ ID NO:24 or SEQ ID NO:30; wherein each of the first and the second VH domains comprises an amino acid sequence having at least 90% sequence identity to SEQ ID NO:23 or SEQ ID NO:29; wherein each of the first and the second VL domains forms a VH-VL binding unit with a corresponding VH domain of the first and the second VH domains; and wherein each of the two VH-VL binding units is specific for human PSGL-1.

108. The tetravalent antibody of claim 107, wherein the first and the second VL domains each comprise (i) a CDR-L1 comprising the amino acid sequence of SEQ ID NO:20; (ii) a CDR-L2 comprising the amino acid sequence of SEQ ID NO:21; and (iii) a CDR-L3 comprising the amino acid sequence of SEQ ID NO:22.

109. The tetravalent antibody of claim 107, wherein the first and the second VH domains each comprise (i) a CDR-H1 comprising the amino acid sequence of SEQ ID NO:17; (ii) a CDR-H2 comprising the amino acid sequence of SEQ ID NO:18; and (iii) a CDR-H3 comprising the amino acid sequence of SEQ ID NO:19.

110. The tetravalent antibody of claim 107, wherein the first and the third linker sequences both have five repeats of SEQ ID NO:25.

111. The tetravalent antibody of claim 107, wherein the second linker sequence has the amino acid sequence of SEQ ID NO:27.

112. The tetravalent antibody of claim 107, wherein the fourth linker sequence has the amino acid sequence of SEQ ID NO:26.

113. The tetravalent antibody of claim 107, wherein the antibody Fc domain is a human antibody Fc domain.

114. The tetravalent antibody of claim 113, wherein the antibody Fc domain is a human IgG4 Fc domain.

115. The tetravalent antibody of claim 114, wherein the human IgG4 Fc domain comprises a hinge region sequence comprising (a) one or more amino acid substitutions that result in reduced IgG4 shuffling, as compared to an IgG4 hinge region lacking the one or more amino acid substitutions, or (b) a serine to proline substitution at amino acid 228, numbering according to EU index.

116. An isolated polynucleotide encoding the tetravalent antibody of claim 107.

117. A vector comprising the isolated polynucleotide of claim 116.

118. A host cell comprising the polynucleotide of claim 116.

119. A method of producing a tetravalent antibody comprising culturing the host cell of claim 118 so that the tetravalent antibody is produced.

120. A pharmaceutical composition comprising the tetravalent antibody of claim 107 and a pharmaceutically acceptable carrier.

121. A method of treating a T-cell mediated inflammatory disease, the method comprising administering to a subject in need thereof a therapeutically effective amount of the tetravalent antibody of claim 107.

122. The method of claim 121, wherein the T-cell mediated inflammatory disease is an autoimmune disease.

123. The method of claim 121, wherein the T-cell mediated inflammatory disease is selected from the group consisting of psoriasis, psoriatic arthritis, rheumatoid arthritis, Crohn's disease, ankylosing spondylitis, type I diabetes, ulcerative colitis, multiple sclerosis, allergy, atopic dermatitis, asthma, and graft versus host disease (GVHD).

124. A method for treating an individual in need of a transfusion or transplantation, comprising administering to the individual a therapeutically effective amount of the tetravalent antibody of claim 107 concurrently with or after the transfusion or transplantation.

125. The method of claim 124, wherein the transplantation is a transplantation of a tissue selected from the group consisting of bone marrow, kidney, heart, liver, neuronal tissue, lung, pancreas, skin, and intestine.

126. The method of claim 124, wherein the transfusion is a transfusion comprising one or more of white blood cells, red blood cells, and platelets.

127. A tetravalent antibody that specifically binds to human PSGL-1, the tetravalent antibody comprising a dimer of two monomers, wherein each monomer of the dimer comprises an antibody heavy chain and an antibody light chain;
  wherein the antibody light chain comprises, from N-terminus to C-terminus:
    (i) a first heavy chain variable (VH) domain,
    (ii) a first linker sequence, wherein the first linker sequence has two, three, four, or five repeats of the amino acid sequence of GGGGS (SEQ ID NO:25),
    (iii) a first light chain variable (VL) domain,
    (iv) a second linker sequence, wherein the second linker sequence has 5-12 amino acids,
    (v) a second VL domain, and
    (vi) a light chain constant (CL) domain;
  wherein the antibody heavy chain comprises:
    (i) a second VH domain, and
    (ii) a heavy chain constant region comprising a first heavy chain constant region (CH1) domain, an antibody hinge region, an second heavy chain constant region (CH2) domain, and a third heavy chain constant region (CH3) domain;
  wherein each of the first and the second VL domains comprises an amino acid sequence having at least 90% sequence identity to SEQ ID NO:24 or SEQ ID NO:30;
  wherein each of the first and the second VH domains comprises an amino acid sequence having at least 90% sequence identity to SEQ ID NO:23 or SEQ ID NO:29;
  wherein each of the first and the second VL domains forms a VH-VL binding unit with a corresponding VH domain of the first and the second VH domains; and
  wherein each of the two VH-VL binding units is specific for human PSGL-1.

128. The tetravalent antibody of claim 127, wherein the first and the second VL domains each comprise (i) a CDR-L1 comprising the amino acid sequence of SEQ ID NO:20; (ii) a CDR-L2 comprising the amino acid sequence of SEQ ID NO:21; and (iii) a CDR-L3 comprising the amino acid sequence of SEQ ID NO:22.

129. The tetravalent antibody of claim 127, wherein the first and the second VH domains each comprise (i) a CDR-H1 comprising the amino acid sequence of SEQ ID NO:17; (ii) a CDR-H2 comprising the amino acid sequence of SEQ ID NO:18; and (iii) a CDR-H3 comprising the amino acid sequence of SEQ ID NO:19.

130. The tetravalent antibody of claim 127, wherein the CL domain is a kappa CL domain.

131. The tetravalent antibody of claim 127, wherein the first linker sequence has five repeats of SEQ ID NO:25.

132. The tetravalent antibody of claim 127, wherein the second linker sequence has the amino acid sequence of SEQ ID NO:28.

133. The tetravalent antibody of claim 127, wherein the antibody Fc domain is a human antibody Fc domain.

134. The tetravalent antibody of claim 133, wherein the antibody Fc domain is a human IgG4 Fc domain.

135. The tetravalent antibody of claim 134, wherein the human IgG4 Fc domain comprises a hinge region sequence comprising (a) one or more amino acid substitutions that result in reduced IgG4 shuffling, as compared to an IgG4 hinge region lacking the one or more amino acid substitutions, or (b) a serine to proline substitution at amino acid 228, numbering according to EU index.

136. An isolated polynucleotide encoding the tetravalent antibody of claim 127.

137. A vector comprising the isolated polynucleotide of claim 136.

138. An isolated host cell comprising the polynucleotide of claim 136.

139. A method of producing a tetravalent antibody comprising culturing the host cell of claim 138 so that the tetravalent antibody is produced.

140. A pharmaceutical composition comprising the tetravalent antibody of claim 127 and a pharmaceutically acceptable carrier.

141. A method of treating a T-cell mediated inflammatory disease, the method comprising administering to a subject in need thereof a therapeutically effective amount of the tetravalent antibody of claim 127.

142. The method of claim 141, wherein the T-cell mediated inflammatory disease is an autoimmune disease.

143. The method of claim 141, wherein the T-cell mediated inflammatory disease is selected from the group consisting of psoriasis, psoriatic arthritis, rheumatoid arthritis, Crohn's disease, ankylosing spondylitis, type I diabetes, ulcerative colitis, multiple sclerosis, allergy, atopic dermatitis, asthma, and graft versus host disease (GVHD).

144. A method for treating an individual in need of a transfusion or transplantation, comprising administering to the individual a therapeutically effective amount of the tetravalent antibody of claim 127 concurrently with or after the transfusion or transplantation.

145. The method of claim 144, wherein the transplantation is a transplantation of a tissue selected from the group consisting of bone marrow, kidney, heart, liver, neuronal tissue, lung, pancreas, skin, and intestine.

146. The method of claim 144, wherein the transfusion is a transfusion comprising one or more of white blood cells, red blood cells, and platelets.

147. The tetravalent antibody of claim 11, wherein one of the first and the second VH domains comprises the amino acid sequence of SEQ ID NO:23, and the other of the first and the second VH domains comprises the amino acid sequence of SEQ ID NO:29.

148. The tetravalent antibody of claim 11, wherein one of the first and the second VL domains comprises the amino acid sequence of SEQ ID NO:24, and the other of the first and the second VL domains comprises the amino acid sequence of SEQ ID NO:30.

149. The tetravalent antibody of claim 21, wherein one of the first and the second VH domains comprises the amino acid sequence of SEQ ID NO:23, and the other of the first and the second VH domains comprises the amino acid sequence of SEQ ID NO:29.

150. The tetravalent antibody of claim 21, wherein one of the first and the second VL domains comprises the amino acid sequence of SEQ ID NO:24, and the other of the first and the second VL domains comprises the amino acid sequence of SEQ ID NO:30.

* * * * *

SEQUENCE LISTING

<160> NUMBER OF SEQ ID NOS: 36

<210> SEQ ID NO 1
<211> LENGTH: 746
<212> TYPE: PRT
<213> ORGANISM: Artificial Sequence
<220> FEATURE:
<223> OTHER INFORMATION: Synthetic Construct

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Val His Asn
            20                  25                  30

Asp Gly Asn Thr Tyr Phe Glu Trp Tyr Gln Gln Lys Pro Gly Lys Ala
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr His Phe Thr Leu Thr Ile
65                  70                  75                  80

```
Ser Ser Leu Gln Pro Glu Asp Phe Ala Thr Tyr Tyr Cys Phe Gln Gly
            85                  90                  95

Ser Tyr Val Pro Leu Thr Phe Gly Gln Gly Thr Lys Val Glu Ile Lys
        100                 105                 110

Gly Gly Gly Gly Ser Gly Gly Gly Ser Glu Val Gln Leu Val Glu
    115                 120                 125

Ser Gly Gly Gly Leu Val Gln Pro Gly Gly Ser Leu Arg Leu Ser Cys
    130                 135                 140

Ala Ala Ser Gly Phe Thr Phe Ser Ser Phe Gly Met His Trp Val Arg
145                 150                 155                 160

Gln Ala Pro Gly Lys Gly Leu Glu Trp Val Ala Tyr Ile Asn Gly Gly
                165                 170                 175

Ser Ser Thr Ile Phe Tyr Ala Asn Ala Val Lys Gly Arg Phe Thr Ile
                180                 185                 190

Ser Arg Asp Asn Ala Lys Asn Thr Leu Tyr Leu Gln Met Asn Ser Leu
    195                 200                 205

Arg Ala Glu Asp Thr Ala Val Tyr Tyr Cys Ala Arg Tyr Ala Ser Tyr
210                 215                 220

Gly Gly Gly Ala Met Asp Tyr Trp Gly Gln Gly Thr Leu Val Thr Val
225                 230                 235                 240

Ser Ser Gly Gly Gly Gly Ser Gly Gly Gly Gly Ser Gly Gly Gly Gly
                245                 250                 255

Ser Gly Gly Gly Gly Ser Gly Gly Gly Gly Ser Asp Ile Gln Met Thr
                260                 265                 270

Gln Ser Pro Ser Ser Leu Ser Ala Ser Val Gly Asp Arg Val Thr Ile
    275                 280                 285

Thr Cys Arg Ser Ser Gln Ser Ile Val His Asn Asp Gly Asn Thr Tyr
    290                 295                 300

Phe Glu Trp Tyr Gln Gln Lys Pro Gly Lys Ala Pro Lys Leu Leu Ile
305                 310                 315                 320

Tyr Lys Val Ser Asn Arg Phe Ser Gly Val Pro Ser Arg Phe Ser Gly
                325                 330                 335

Ser Gly Ser Gly Thr His Phe Thr Leu Thr Ile Ser Ser Leu Gln Pro
                340                 345                 350

Glu Asp Phe Ala Thr Tyr Tyr Cys Phe Gln Gly Ser Tyr Val Pro Leu
            355                 360                 365

Thr Phe Gly Gln Gly Thr Lys Val Glu Ile Lys Gly Gly Gly Gly Ser
    370                 375                 380

Gly Gly Gly Gly Ser Glu Val Gln Leu Val Glu Ser Gly Gly Gly Leu
385                 390                 395                 400

Val Gln Pro Gly Gly Ser Leu Arg Leu Ser Cys Ala Ala Ser Gly Phe
        405                 410                 415

Thr Phe Ser Ser Phe Gly Met His Trp Val Arg Gln Ala Pro Gly Lys
        420                 425                 430

Gly Leu Glu Trp Val Ala Tyr Ile Asn Gly Gly Ser Ser Thr Ile Phe
        435                 440                 445

Tyr Ala Asn Ala Val Lys Gly Arg Phe Thr Ile Ser Arg Asp Asn Ala
        450                 455                 460

Lys Asn Thr Leu Tyr Leu Gln Met Asn Ser Leu Arg Ala Glu Asp Thr
465                 470                 475                 480

Ala Val Tyr Tyr Cys Ala Arg Tyr Ala Ser Tyr Gly Gly Gly Ala Met
                485                 490                 495
```

Asp Tyr Trp Gly Gln Gly Thr Leu Val Thr Val Ser Ser Gly Gly Gly
                500                 505                 510

Gly Ser Ala Ala Ala Glu Ser Lys Tyr Gly Pro Pro Cys Pro Pro Cys
        515                 520                 525

Pro Ala Pro Glu Phe Leu Gly Gly Pro Ser Val Phe Leu Phe Pro Pro
        530                 535                 540

Lys Pro Lys Asp Thr Leu Met Ile Ser Arg Thr Pro Glu Val Thr Cys
545                 550                 555                 560

Val Val Val Asp Val Ser Gln Glu Asp Pro Glu Val Gln Phe Asn Trp
                565                 570                 575

Tyr Val Asp Gly Val Glu Val His Asn Ala Lys Thr Lys Pro Arg Glu
        580                 585                 590

Glu Gln Phe Asn Ser Thr Tyr Arg Val Val Ser Val Leu Thr Val Leu
        595                 600                 605

His Gln Asp Trp Leu Asn Gly Lys Glu Tyr Lys Cys Lys Val Ser Asn
        610                 615                 620

Lys Gly Leu Pro Ser Ser Ile Glu Lys Thr Ile Ser Lys Ala Lys Gly
625                 630                 635                 640

Gln Pro Arg Glu Pro Gln Val Tyr Thr Leu Pro Pro Ser Gln Glu Glu
                645                 650                 655

Met Thr Lys Asn Gln Val Ser Leu Thr Cys Leu Val Lys Gly Phe Tyr
        660                 665                 670

Pro Ser Asp Ile Ala Val Glu Trp Glu Ser Asn Gly Gln Pro Glu Asn
        675                 680                 685

Asn Tyr Lys Thr Thr Pro Pro Val Leu Asp Ser Asp Gly Ser Phe Phe
        690                 695                 700

Leu Tyr Ser Arg Leu Thr Val Asp Lys Ser Arg Trp Gln Glu Gly Asn
705                 710                 715                 720

Val Phe Ser Cys Ser Val Met His Glu Ala Leu His Asn His Tyr Thr
                725                 730                 735

Gln Lys Ser Leu Ser Leu Ser Leu Gly Lys
        740                 745

<210> SEQ ID NO 2
<211> LENGTH: 2241
<212> TYPE: DNA
<213> ORGANISM: Artificial Sequence
<220> FEATURE:
<223> OTHER INFORMATION: Synthetic Construct

<400> SEQUENCE: 2

```
gacattcaga tgacccaatc tccgagctct tgtctgcgt ctgtagggga tagggtcact      60
atcacctgca gatctagtca gagcattgta cataatgatg aaacacccta ttttgaatgg    120
taccaacaga aaccaggaaa ggcacccaag cttctcatct ataaagtttc caatcgattt    180
tctggtgtcc catccaggtt tagtggcagt gggtctggga cacttcac cctcaccatc      240 tcttctctgc agccggagga tttcgcaacc tattactgtt tcaaggttc atatgttcct    300 ctcacgttcg gtcaaggcac caaggtggaa atcaaggtg gaggcggttc aggcggaggt    360
ggctctgaag tgcaactggt ggagtctggg ggaggcttag tgcagcctgg aggaagcttg    420
agactctcct gtgcagcctc tggattcact ttcagtagct ttggaatgca ctgggttcgc    480
caggctccag gaagggact cgagtgggtc gcatacatta tggtggcag tagtaccatc    540 ttctatgcaa acgcagtgaa gggccgattc accatctcca gagataatgc caagaacacc    600
ctgtacctgc aaatgaattc tctgagggct gaggacacgg ccgtgtatta ctgtgcaaga    660
```

-continued

```
tatgctagtt acggaggggg tgctatggac tattggggcc aaggcaccct ggtcacagtc      720
tcctcaggtg gaggcggttc aggcggaggt ggctctggcg gtggcggatc cggaggcgga      780
ggttccggag gtggcggaag tgacattcag atgacccaat ctccgagctc tttgtctgcg      840
tctgtagggg atagggtcac tatcacctgc agatctagtc agagcattgt acataatgat      900
ggaaacacct attttgaatg gtaccaacag aaaccaggaa aggcacccaa gcttctcatc      960
tataaagttt ccaatcgatt ttctggtgtc ccatccaggt ttagtggcag tgggtctggg     1020
acacacttca ccctcaccat ctcttctctg cagccggagg atttcgcaac ctattactgt     1080
tttcaaggtt catatgttcc tctcacgttc ggtcaaggca ccaaggtgga atcaaaggt      1140 ggaggcggtt caggcggagg tggctctgaa gtgcaactgg tggagtctgg gggaggctta     1200
gtgcagcctg gaggaagctt gagactctcc tgtgcagcct ctggattcac tttcagtagc     1260
tttggaatgc actgggttcg ccaggctcca gggaagggac tcgagtgggt cgcatacatt     1320
aatggtggca gtagtaccat cttctatgca aacgcagtga agggccgatt caccatctcc     1380
agagataatg ccaagaacac cctgtacctg caaatgaatt ctctgagggc tgaggacacg     1440
gccgtgtatt actgtgcaag atatgctagt tacggagggg gtgctatgga ctattgggc      1500 caaggcaccc tggtcacagt ctcctcagga ggcggaggtt ccgcggccgc agagtccaaa     1560
tatggtcccc catgcccacc atgcccagca cctgagttcc tggggggacc atcagtcttc     1620
ctgttccccc caaaacccaa ggacactctc atgatctccc ggacccctga ggtcacgtgc     1680
gtggtggtgg acgtgagcca ggaagacccc gaggtccagt tcaactggta cgtggatggc     1740
gtggaggtgc ataatgccaa gacaaagccg cgggaggagc agttcaacag cacgtaccgt     1800
gtggtcagcg tcctcaccgt cctgcaccag gactggctga acggcaagga gtacaagtgc     1860
aaggtctcca acaaaggcct cccgtcctcc atcgagaaaa ccatctccaa agccaaaggg     1920
cagccccgag agccacaggt gtacaccctg cccccatccc aggaggagat gaccaagaac     1980
caggtcagcc tgacctgcct ggtcaaaggc ttctacccca gcgacatcgc cgtggagtgg     2040
gagagcaatg ggcagccgga gaacaactac aagaccacgc ctcccgtgct ggactccgac     2100
ggctccttct tcctctacag caggctaacc gtggacaaga gcaggtggca ggaggggaat     2160
gtcttctcat gctccgtgat gcatgaggct ctgcacaacc actacacaca gaagagcctc     2220
tccctgtctc tgggtaaatg a                                               2241
```

<210> SEQ ID NO 3
<211> LENGTH: 756
<212> TYPE: PRT
<213> ORGANISM: Artificial Sequence
<220> FEATURE:
<223> OTHER INFORMATION: Synthetic Construct

<400> SEQUENCE: 3

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Cys Leu Glu Trp Val
        35                  40                  45

Ala Tyr Ile Asn Gly Gly Ser Ser Thr Ile Phe Tyr Ala Asn Ala Val
    50                  55                  60

Lys Gly Arg Phe Thr Ile Ser Arg Asp Asn Ala Lys Asn Thr Leu Tyr
65                  70                  75                  80
```

-continued

```
Leu Gln Met Asn Ser Leu Arg Ala Glu Asp Thr Ala Val Tyr Tyr Cys
                 85                  90                  95
Ala Arg Tyr Ala Ser Tyr Gly Gly Gly Ala Met Asp Tyr Trp Gly Gln
            100                 105                 110
Gly Thr Leu Val Thr Val Ser Gly Gly Gly Ser Gly Gly Gly
        115                 120                 125
Gly Ser Gly Gly Gly Ser Gly Gly Gly Ser Gly Gly Gly
    130                 135                 140
Ser Asp Ile Gln Met Thr Gln Ser Pro Ser Ser Leu Ser Ala Ser Val
145                 150                 155                 160
Gly Asp Arg Val Thr Ile Thr Cys Arg Ser Ser Gln Ser Ile Val His
                165                 170                 175
Asn Asp Gly Asn Thr Tyr Phe Glu Trp Tyr Gln Gln Lys Pro Gly Lys
            180                 185                 190
Ala Pro Lys Leu Leu Ile Tyr Lys Val Ser Asn Arg Phe Ser Gly Val
        195                 200                 205
Pro Ser Arg Phe Ser Gly Ser Gly Ser Gly Thr His Phe Thr Leu Thr
    210                 215                 220
Ile Ser Ser Leu Gln Pro Glu Asp Phe Ala Thr Tyr Tyr Cys Phe Gln
225                 230                 235                 240
Gly Ser Tyr Val Pro Leu Thr Phe Gly Cys Gly Thr Lys Val Glu Ile
                245                 250                 255
Lys Ala Ser Thr Gly Ser Asp Ile Gln Met Thr Gln Ser Pro Ser Ser
            260                 265                 270
Leu Ser Ala Ser Val Gly Asp Arg Val Thr Ile Thr Cys Arg Ser Ser
        275                 280                 285
Gln Ser Ile Val His Asn Asp Gly Asn Thr Tyr Phe Glu Trp Tyr Gln
    290                 295                 300
Gln Lys Pro Gly Lys Ala Pro Lys Leu Leu Ile Tyr Lys Val Ser Asn
305                 310                 315                 320
Arg Phe Ser Gly Val Pro Ser Arg Phe Ser Gly Ser Gly Ser Gly Thr
                325                 330                 335
His Phe Thr Leu Thr Ile Ser Ser Leu Gln Pro Glu Asp Phe Ala Thr
            340                 345                 350
Tyr Tyr Cys Phe Gln Gly Ser Tyr Val Pro Leu Thr Phe Gly Gln Gly
        355                 360                 365
Thr Lys Val Glu Ile Lys Gly Gly Gly Gly Ser Gly Gly Gly Gly Ser
    370                 375                 380
Gly Gly Gly Gly Ser Gly Gly Gly Ser Gly Gly Gly Gly Ser Glu
385                 390                 395                 400
Val Gln Leu Val Glu Ser Gly Gly Leu Val Gln Pro Gly Gly Ser
                405                 410                 415
Leu Arg Leu Ser Cys Ala Ala Ser Gly Phe Thr Phe Ser Ser Phe Gly
            420                 425                 430
Met His Trp Val Arg Gln Ala Pro Gly Lys Gly Leu Glu Trp Val Ala
        435                 440                 445
Tyr Ile Asn Gly Gly Ser Ser Thr Ile Phe Tyr Ala Asn Ala Val Lys
    450                 455                 460
Gly Arg Phe Thr Ile Ser Arg Asp Asn Ala Lys Asn Thr Leu Tyr Leu
465                 470                 475                 480
Gln Met Asn Ser Leu Arg Ala Glu Asp Thr Ala Val Tyr Tyr Cys Ala
                485                 490                 495
```

```
Arg Tyr Ala Ser Tyr Gly Gly Gly Ala Met Asp Tyr Trp Gly Gln Gly
                500                 505                 510

Thr Leu Val Thr Val Ser Ser Gly Gly Gly Ser Ala Ala Ala Glu
        515                 520                 525

Ser Lys Tyr Gly Pro Pro Cys Pro Pro Cys Pro Ala Pro Glu Phe Leu
    530                 535                 540

Gly Gly Pro Ser Val Phe Leu Phe Pro Pro Lys Pro Lys Asp Thr Leu
545                 550                 555                 560

Met Ile Ser Arg Thr Pro Glu Val Thr Cys Val Val Val Asp Val Ser
                565                 570                 575

Gln Glu Asp Pro Glu Val Gln Phe Asn Trp Tyr Val Asp Gly Val Glu
            580                 585                 590

Val His Asn Ala Lys Thr Lys Pro Arg Glu Glu Gln Phe Asn Ser Thr
        595                 600                 605

Tyr Arg Val Val Ser Val Leu Thr Val Leu His Gln Asp Trp Leu Asn
    610                 615                 620

Gly Lys Glu Tyr Lys Cys Lys Val Ser Asn Lys Gly Leu Pro Ser Ser
625                 630                 635                 640

Ile Glu Lys Thr Ile Ser Lys Ala Lys Gly Gln Pro Arg Glu Pro Gln
                645                 650                 655

Val Tyr Thr Leu Pro Pro Ser Gln Glu Glu Met Thr Lys Asn Gln Val
            660                 665                 670

Ser Leu Thr Cys Leu Val Lys Gly Phe Tyr Pro Ser Asp Ile Ala Val
        675                 680                 685

Glu Trp Glu Ser Asn Gly Gln Pro Glu Asn Asn Tyr Lys Thr Thr Pro
    690                 695                 700

Pro Val Leu Asp Ser Asp Gly Ser Phe Phe Leu Tyr Ser Arg Leu Thr
705                 710                 715                 720

Val Asp Lys Ser Arg Trp Gln Glu Gly Asn Val Phe Ser Cys Ser Val
                725                 730                 735

Met His Glu Ala Leu His Asn His Tyr Thr Gln Lys Ser Leu Ser Leu
            740                 745                 750

Ser Leu Gly Lys
        755

<210> SEQ ID NO 4
<211> LENGTH: 2271
<212> TYPE: DNA
<213> ORGANISM: Artificial Sequence
<220> FEATURE:
<223> OTHER INFORMATION: Synthetic Construct

<400> SEQUENCE: 4
gaagtgcaac tggtggagtc tgggggaggc ttagtgcagc ctggaggaag cttgagactc    60
tcctgtgcag cctctggatt cactttcagt agctttggaa tgcactgggt tcgccaggct   120
ccagggaagt gtctcgagtg gtcgcatac attaatggtg gcagtagtac catcttctat   180
gcaaacgcag tgaagggccg attcaccatc tccagagata tgccaagaa caccctgtac   240 ctgcaaatga attctctgag ggctgaggac acggccgtgt attactgtgc aagatatgct   300
agttacggag gggtgctat ggactattgg ggccaaggca ccctggtcac agtctcctca   360
ggtggaggcg gttcaggcgg aggtggctct ggcggtggcg gatccggagg cggaggttcc   420
ggaggtggcg gaagtgacat tcagatgacc caatctccga gctctttgtc tgcgtctgta   480
ggggataggg tcactatcac ctgcagatct agtcagagca ttgtacataa tgatggaaac   540
```

```
acctatttg aatggtacca acagaaacca ggaaaggcac ccaagcttct catctataaa    600
gtttccaatc gattttctgg tgtcccatcc aggtttagtg gcagtgggtc tgggacacac    660
ttcaccctca ccatctcttc tctgcagccg gaggatttcg caacctatta ctgttttcaa    720
ggttcatatg ttcctctcac gttcggttgt ggcaccaagg tggaaatcaa agcttcaacc    780
ggttcagaca ttcagatgac ccaatctccg agctctttgt ctgcgtctgt aggggatagg    840
gtcactatca cctgcagatc tagtcagagc attgtacata tgatggaaa cacctatttt    900
gaatggtacc aacagaaacc aggaaaggca cccaagcttc tcatctataa agtttccaat    960
cgattttctg gtgtcccatc caggtttagt ggcagtgggt ctgggacaca cttcaccctc   1020
accatctctt ctctgcagcc ggaggatttc gcaacctatt actgttttca aggttcatat   1080
gttcctctca cgttcggtca aggcaccaag gtggaaatca aggtggagg cggttcaggc    1140
ggaggtggct ctggcggtgg cggatccgga ggcggaggtt ccggaggtgg cggaagtgaa   1200
gtgcaactgg tggagtctgg gggaggctta gtgcagcctg gaggaagctt gagactctcc   1260
tgtgcagcct ctggattcac tttcagtagc tttggaatgc actgggttcg ccaggctcca   1320
gggaagggac tcgagtgggt cgcatacatt aatggtggca gtagtaccat cttctatgca   1380
aacgcagtga agggccgatt caccatctcc agagataatg ccaagaacac cctgtacctg   1440
caaatgaatt ctctgagggc tgaggacacg gccgtgtatt actgtgcaag atatgctagt   1500
tacgaggggg gtgctatgga ctattgggc caaggcaccc tggtcacagt ctcctcagga   1560
ggcggaggtt ccgcggccgc agagtccaaa tatggtcccc catgcccacc atgcccagca   1620
cctgagttcc tggggggacc atcagtcttc ctgttccccc caaaacccaa ggacactctc   1680
atgatctccc ggacccctga ggtcacgtgc gtggtggtgg acgtgagcca ggaagacccc   1740
gaggtccagt tcaactggta cgtggatggc gtggaggtgc ataatgccaa gacaaagccg   1800
cgggaggagc agttcaacag cacgtaccgt gtggtcagcg tcctcaccgt cctgcaccag   1860
gactggctga acggcaagga gtacaagtgc aaggtctcca acaaaggcct cccgtcctcc   1920
atcgagaaaa ccatctccaa agccaaaggg cagccccgag agccacaggt gtacaccctg   1980
cccccatccc aggaggagat gaccaagaac caggtcagcc tgacctgcct ggtcaaaggc   2040
ttctacccca gcgacatcgc cgtggagtgg gagagcaatg ggcagccgga gaacaactac   2100
aagaccacgc ctcccgtgct ggactccgac ggctccttct cctctacag caggctaacc   2160
gtggacaaga gcaggtggca ggaggggaat gtcttctcat gctccgtgat gcatgaggct   2220
ctgcacaacc actacacaca gaagagcctc tccctgtctc tgggtaaatg a            2271
```

<210> SEQ ID NO 5
<211> LENGTH: 756
<212> TYPE: PRT
<213> ORGANISM: Artificial Sequence
<220> FEATURE:
<223> OTHER INFORMATION: Synthetic Construct

<400> SEQUENCE: 5

```
Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Val His Asn
            20                  25                  30

Asp Gly Asn Thr Tyr Phe Glu Trp Tyr Gln Gln Lys Pro Gly Lys Ala
        35                  40                  45

Pro Lys Leu Leu Ile Tyr Lys Val Ser Asn Arg Phe Ser Gly Val Pro
    50                  55                  60
```

```
Ser Arg Phe Ser Gly Ser Gly Ser Gly Thr His Phe Thr Leu Thr Ile
 65                  70                  75                  80

Ser Ser Leu Gln Pro Glu Asp Phe Ala Thr Tyr Tyr Cys Phe Gln Gly
                 85                  90                  95

Ser Tyr Val Pro Leu Thr Phe Gly Cys Gly Thr Lys Val Glu Ile Lys
            100                 105                 110

Gly Gly Gly Gly Ser Gly Gly Gly Ser Gly Gly Gly Ser Gly
        115                 120                 125

Gly Gly Gly Ser Gly Gly Gly Ser Glu Val Gln Leu Val Glu Ser
130                 135                 140

Gly Gly Gly Leu Val Gln Pro Gly Gly Ser Leu Arg Leu Ser Cys Ala
145                 150                 155                 160

Ala Ser Gly Phe Thr Phe Ser Ser Phe Gly Met His Trp Val Arg Gln
                165                 170                 175

Ala Pro Gly Lys Cys Leu Glu Trp Val Ala Tyr Ile Asn Gly Gly Ser
            180                 185                 190

Ser Thr Ile Phe Tyr Ala Asn Ala Val Lys Gly Arg Phe Thr Ile Ser
        195                 200                 205

Arg Asp Asn Ala Lys Asn Thr Leu Tyr Leu Gln Met Asn Ser Leu Arg
210                 215                 220

Ala Glu Asp Thr Ala Val Tyr Tyr Cys Ala Arg Tyr Ala Ser Tyr Gly
225                 230                 235                 240

Gly Gly Ala Met Asp Tyr Trp Gly Gln Gly Thr Leu Val Thr Val Ser
                245                 250                 255

Ser Ala Ser Thr Gly Ser Glu Val Gln Leu Val Glu Ser Gly Gly Gly
            260                 265                 270

Leu Val Gln Pro Gly Gly Ser Leu Arg Leu Ser Cys Ala Ala Ser Gly
        275                 280                 285

Phe Thr Phe Ser Ser Phe Gly Met His Trp Val Arg Gln Ala Pro Gly
290                 295                 300

Lys Cys Leu Glu Trp Val Ala Tyr Ile Asn Gly Gly Ser Ser Thr Ile
305                 310                 315                 320

Phe Tyr Ala Asn Ala Val Lys Gly Arg Phe Thr Ile Ser Arg Asp Asn
                325                 330                 335

Ala Lys Asn Thr Leu Tyr Leu Gln Met Asn Ser Leu Arg Ala Glu Asp
            340                 345                 350

Thr Ala Val Tyr Tyr Cys Ala Arg Tyr Ala Ser Tyr Gly Gly Gly Ala
        355                 360                 365

Met Asp Tyr Trp Gly Gln Gly Thr Leu Val Thr Val Ser Ser Gly Gly
370                 375                 380

Gly Gly Ser Gly Gly Gly Ser Gly Gly Gly Ser Gly Gly Gly
385                 390                 395                 400

Gly Ser Gly Gly Gly Ser Asp Ile Gln Met Thr Gln Ser Pro Ser
            405                 410                 415

Ser Leu Ser Ala Ser Val Gly Asp Arg Val Thr Ile Thr Cys Arg Ser
            420                 425                 430

Ser Gln Ser Ile Val His Asn Asp Gly Asn Thr Tyr Phe Glu Trp Tyr
        435                 440                 445

Gln Gln Lys Pro Gly Lys Ala Pro Lys Leu Leu Ile Tyr Lys Val Ser
    450                 455                 460

Asn Arg Phe Ser Gly Val Pro Ser Arg Phe Ser Gly Ser Gly Ser Gly
465                 470                 475                 480
```

Thr His Phe Thr Leu Thr Ile Ser Ser Leu Gln Pro Glu Asp Phe Ala
            485                 490                 495

Thr Tyr Tyr Cys Phe Gln Gly Ser Tyr Val Pro Leu Thr Phe Gly Cys
        500                 505                 510

Gly Thr Lys Val Glu Ile Lys Gly Gly Gly Ser Ala Ala Ala Glu
        515                 520                 525

Ser Lys Tyr Gly Pro Pro Cys Pro Pro Cys Pro Ala Pro Glu Phe Leu
    530                 535                 540

Gly Gly Pro Ser Val Phe Leu Phe Pro Pro Lys Pro Lys Asp Thr Leu
545                 550                 555                 560

Met Ile Ser Arg Thr Pro Glu Val Thr Cys Val Val Val Asp Val Ser
                565                 570                 575

Gln Glu Asp Pro Glu Val Gln Phe Asn Trp Tyr Val Asp Gly Val Glu
            580                 585                 590

Val His Asn Ala Lys Thr Lys Pro Arg Glu Glu Gln Phe Asn Ser Thr
        595                 600                 605

Tyr Arg Val Val Ser Val Leu Thr Val Leu His Gln Asp Trp Leu Asn
610                 615                 620

Gly Lys Glu Tyr Lys Cys Lys Val Ser Asn Lys Gly Leu Pro Ser Ser
625                 630                 635                 640

Ile Glu Lys Thr Ile Ser Lys Ala Lys Gly Gln Pro Arg Glu Pro Gln
                645                 650                 655

Val Tyr Thr Leu Pro Pro Ser Gln Glu Glu Met Thr Lys Asn Gln Val
            660                 665                 670

Ser Leu Thr Cys Leu Val Lys Gly Phe Tyr Pro Ser Asp Ile Ala Val
        675                 680                 685

Glu Trp Glu Ser Asn Gly Gln Pro Glu Asn Asn Tyr Lys Thr Thr Pro
    690                 695                 700

Pro Val Leu Asp Ser Asp Gly Ser Phe Phe Leu Tyr Ser Arg Leu Thr
705                 710                 715                 720

Val Asp Lys Ser Arg Trp Gln Glu Gly Asn Val Phe Ser Cys Ser Val
                725                 730                 735

Met His Glu Ala Leu His Asn His Tyr Thr Gln Lys Ser Leu Ser Leu
            740                 745                 750

Ser Leu Gly Lys
        755

<210> SEQ ID NO 6
<211> LENGTH: 2271
<212> TYPE: DNA
<213> ORGANISM: Artificial Sequence
<220> FEATURE:
<223> OTHER INFORMATION: Synthetic Construct

<400> SEQUENCE: 6
gacattcaga tgacccaatc tccgagctct ttgtctgcgt ctgtagggga tagggtcact      60
atcacctgca gatctagtca gagcattgta cataatgatg aaacacctta ttttgaatgg     120
taccaacaga aaccaggaaa ggcacccaag cttctcatct ataaagtttc caatcgattt     180
tctggtgtcc catccaggtt tagtggcagt gggtctggga cacacttcac cctcaccatc     240
tcttctctgc agccggagga tttcgcaacc tattactgtt ttcaaggttc atatgttcct     300
ctcacgttcg gttgtggcac caaggtggaa atcaaaggtg gaggcggttc aggcggaggt     360
ggctctggcg gtggcggatc cggaggcgga ggttccggag gtggcggaag tgaagtgcaa     420
ctggtggagt ctgggggagg cttagtgcag cctggaggaa gcttgagact ctcctgtgca     480

```
gcctctggat tcactttcag tagctttgga atgcactggg ttcgccaggc tccagggaag    540
tgtctcgagt gggtcgcata cattaatggt ggcagtagta ccatcttcta tgcaaacgca    600
gtgaagggcc gattcaccat ctccagagat aatgccaaga acaccctgta cctgcaaatg    660
aattctctga gggctgagga cacggccgtg tattactgtg caagatatgc tagttacgga    720
gggggtgcta tggactattg gggccaaggc accctggtca cagtctcctc agcttcaacc    780
ggttcagaag tgcaactggt ggagtctggg ggaggcttag tgcagcctgg aggaagcttg    840
agactctcct gtgcagcctc tggattcact ttcagtagct ttggaatgca ctgggttcgc    900
caggctccag gaagtgtctc gagtgggtc gcatacatta atggtggcag tagtaccatc    960
ttctatgcaa acgcagtgaa gggccgattc accatctcca gagataatgc caagaacacc   1020
ctgtacctgc aaatgaattc tctgagggct gaggacacgg ccgtgtatta ctgtgcaaga   1080
tatgctagtt acggagggg tgctatggac tattggggcc aaggcaccct ggtcacagtc   1140
tcctcaggtg gaggcggttc aggcggaggt ggctctggcg gtggcggatc cggaggcgga   1200
ggttccggag gtggcggaag tgacattcag atgacccaat ctccgagctc tttgtctgcg   1260
tctgtagggg atagggtcac tatcacctgc agatctagtc agagcattgt acataatgat   1320
ggaaacacct attttgaatg gtaccaacag aaaccaggaa aggcacccaa gcttctcatc   1380
tataaagttt ccaatcgatt ttctggtgtc ccatccaggt ttagtggcag tgggtctggg   1440
acacacttca ccctcaccat ctcttctctg cagccggagg atttcgcaac ctattactgt   1500
tttcaaggtt catatgttcc tctcacgttc ggttgtggca ccaaggtgga atcaaagga    1560 ggcggaggtt ccgcggccgc agagtccaaa tatggtcccc catgcccacc atgcccagca   1620
cctgagttcc tggggggacc atcagtcttc ctgttccccc caaaacccaa ggacactctc   1680
atgatctccc ggacccctga ggtcacgtgc gtggtggtgg acgtgagcca ggaagacccc   1740
gaggtccagt tcaactggta cgtggatggc gtggaggtgc ataatgccaa gacaaagccg   1800
cgggaggagc agttcaacag cacgtaccgt gtggtcagcg tcctcaccgt cctgcaccag   1860
gactggctga acggcaagga gtacaagtgc aaggtctcca acaaaggcct cccgtcctcc   1920
atcgagaaaa ccatctccaa agccaaaggg cagccccgag agccacaggt gtacaccctg   1980
cccccatccc aggaggagat gaccaagaac caggtcagcc tgacctgcct ggtcaaaggc   2040
ttctacccca gcgacatcgc cgtggagtgg gagagcaatg ggcagccgga gaacaactac   2100
aagaccacgc ctcccgtgct ggactccgac ggctccttct tcctctacag caggctaacc   2160
gtggacaaga gcaggtggca ggaggggaat gtcttctcat gctccgtgat gcatgaggct   2220
ctgcacaacc actacacaca gaagagcctc tccctgtctc tgggtaaatg a            2271
```

<210> SEQ ID NO 7
<211> LENGTH: 486
<212> TYPE: PRT
<213> ORGANISM: Artificial Sequence
<220> FEATURE:
<223> OTHER INFORMATION: Synthetic Construct

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Cys Leu Glu Trp Val
        35                  40                  45

```
Ala Tyr Ile Asn Gly Gly Ser Thr Ile Phe Tyr Ala Asn Ala Val
 50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Tyr Ala Ser Tyr Gly Gly Ala Met Asp Tyr Trp Gly Gln
            100                 105                 110

Gly Thr Leu Val Thr Val Ser Ser Gly Gly Gly Ser Gly Gly Gly
            115                 120                 125

Gly Ser Gly Gly Gly Ser Gly Gly Gly Ser Gly Gly Gly Gly
    130                 135                 140

Ser Asp Ile Gln Met Thr Gln Ser Pro Ser Ser Leu Ser Ala Ser Val
145                 150                 155                 160

Gly Asp Arg Val Thr Ile Thr Cys Arg Ser Ser Gln Ser Ile Val His
                165                 170                 175

Asn Asp Gly Asn Thr Tyr Phe Glu Trp Tyr Gln Gln Lys Pro Gly Lys
                180                 185                 190

Ala Pro Lys Leu Leu Ile Tyr Lys Val Ser Asn Arg Phe Ser Gly Val
            195                 200                 205

Pro Ser Arg Phe Ser Gly Ser Gly Ser Gly Thr His Phe Thr Leu Thr
    210                 215                 220

Ile Ser Ser Leu Gln Pro Glu Asp Phe Ala Thr Tyr Tyr Cys Phe Gln
225                 230                 235                 240

Gly Ser Tyr Val Pro Leu Thr Phe Gly Cys Gly Thr Lys Val Glu Ile
                245                 250                 255

Lys Ala Ser Thr Gly Ser Gly Gly Gly Ser Asp Ile Gln Met Thr
                260                 265                 270

Gln Ser Pro Ser Ser Leu Ser Ala Ser Val Gly Asp Arg Val Thr Ile
    275                 280                 285

Thr Cys Arg Ser Ser Gln Ser Ile Val His Asn Asp Gly Asn Thr Tyr
    290                 295                 300

Phe Glu Trp Tyr Gln Gln Lys Pro Gly Lys Ala Pro Lys Leu Leu Ile
305                 310                 315                 320

Tyr Lys Val Ser Asn Arg Phe Ser Gly Val Pro Ser Arg Phe Ser Gly
                325                 330                 335

Ser Gly Ser Gly Thr His Phe Thr Leu Thr Ile Ser Ser Leu Gln Pro
            340                 345                 350

Glu Asp Phe Ala Thr Tyr Tyr Cys Phe Gln Gly Ser Tyr Val Pro Leu
            355                 360                 365

Thr Phe Gly Gln Gly Thr Lys Val Glu Ile Lys Arg Thr Val Ala Ala
    370                 375                 380

Pro Ser Val Phe Ile Phe Pro Pro Ser Asp Glu Gln Leu Lys Ser Gly
385                 390                 395                 400

Thr Ala Ser Val Val Cys Leu Leu Asn Asn Phe Tyr Pro Arg Glu Ala
                405                 410                 415

Lys Val Gln Trp Lys Val Asp Asn Ala Leu Gln Ser Gly Asn Ser Gln
            420                 425                 430

Glu Ser Val Thr Glu Gln Asp Ser Lys Asp Ser Thr Tyr Ser Leu Ser
            435                 440                 445

Ser Thr Leu Thr Leu Ser Lys Ala Asp Tyr Glu Lys His Lys Val Tyr
    450                 455                 460
```

Ala Cys Glu Val Thr His Gln Gly Leu Ser Ser Pro Val Thr Lys Ser
465                 470                 475                 480

Phe Asn Arg Gly Glu Cys
                485

<210> SEQ ID NO 8
<211> LENGTH: 1461
<212> TYPE: DNA
<213> ORGANISM: Artificial Sequence
<220> FEATURE:
<223> OTHER INFORMATION: Synthetic Construct

<400> SEQUENCE: 8

```
gaagtgcaac tggtggagtc tgggggaggc ttagtgcagc ctggaggaag cttgagactc      60
tcctgtgcag cctctggatt cactttcagt agctttggaa tgcactgggt tcgccaggct     120
ccagggaagt gtctcgagtg ggtcgcatac attaatggtg cagtagtac catcttctat      180
gcaaacgcag tgaagggccg attcaccatc tccagagata tgccaagaa caccctgtac      240
ctgcaaatga attctctgag ggctgaggac acggccgtgt attactgtgc aagatatgct     300
agttacggag gggtgctat ggactattgg ggccaaggca ccctggtcac agtctcctca      360
ggtggaggcg gttcaggcgg aggtggctct ggcggtggcg gatccggagg cggaggttcc     420
ggaggtggcg gaagtgacat tcagatgacc caatctccga gctctttgtc tgcgtctgta     480
ggggataggg tcactatcac ctgcagatct agtcagagca ttgtacataa tgatggaaac     540
acctatttg aatggtacca acagaaacca ggaaaggcac ccaagcttct catctataaa     600
gtttccaatc gattttctgg tgtcccatcc aggtttagtg gcagtgggtc tgggacacac     660
ttcacccctca ccatctcttc tctgcagccg aggatttcg caacctatta ctgttttcaa     720
ggttcatatg ttcctctcac gttcggttgt ggcaccaagg tggaaatcaa agcttcaacc     780
ggttcaggag gtggcggaag tgacattcag atgacccaat ctccgagctc tttgtctgcg     840
tctgtagggg atagggtcac tatcacctgc agatctagtc agagcattgt acataatgat     900
ggaaacacct atttgaatg gtaccaacag aaaccaggaa aggcacccaa gcttctcatc     960
tataaagttt ccaatcgatt ttctggtgtc ccatccaggt ttagtggcag tgggtctggg    1020
acacacttca ccctcaccat ctcttctctg cagccggagg atttcgcaac ctattactgt    1080
ttcaaggtt catatgttcc tctcacgttc ggtcaaggca ccaaggtgga aatcaaacga    1140
actgtggctg caccatctgt cttcatcttc ccgccatctg atgagcagtt gaaatctgga    1200
actgcctctg ttgtgtgcct gctgaataac ttctatccca gagaggccaa agtacagtgg    1260
aaggtggata acgccctcca atcgggtaac tcccaggaga gtgtcacaga gcaggacagc    1320
aaggacagca cctacagcct cagcagcacc ctgacgctga gcaaagcaga ctacgagaaa    1380
cacaaagtct acgcctgcga agtcacccat cagggcctga gctcgcccgt cacaaagagc    1440
ttcaacaggg gagagtgtta g                                              1461
```

<210> SEQ ID NO 9
<211> LENGTH: 499
<212> TYPE: PRT
<213> ORGANISM: Artificial Sequence
<220> FEATURE:
<223> OTHER INFORMATION: Synthetic Construct

<400> SEQUENCE: 9

Asp Ile Gln Met Thr Gln Ser Pro Ser Ser Leu Ser Ala Ser Val Gly
1               5                   10                  15

```
Asp Arg Val Thr Ile Thr Cys Arg Ser Ser Gln Ser Ile His Asn
                20                  25                  30

Asp Gly Asn Thr Tyr Phe Glu Trp Tyr Gln Gln Lys Pro Gly Lys Ala
            35                  40                  45

Pro Lys Leu Leu Ile Tyr Lys Val Ser Asn Arg Phe Ser Gly Val Pro
        50                  55                  60

Ser Arg Phe Ser Gly Ser Gly Ser Gly Thr His Phe Thr Leu Thr Ile
65                  70                  75                  80

Ser Ser Leu Gln Pro Glu Asp Phe Ala Thr Tyr Tyr Cys Phe Gln Gly
                85                  90                  95

Ser Tyr Val Pro Leu Thr Phe Gly Gln Gly Thr Lys Val Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys Gly Gly Gly Gly Ser
210                 215                 220

Gly Gly Gly Gly Ser Glu Val Gln Leu Val Glu Ser Gly Gly Gly Leu
225                 230                 235                 240

Val Gln Pro Gly Gly Ser Leu Arg Leu Ser Cys Ala Ala Ser Gly Phe
                245                 250                 255

Thr Phe Ser Ser Phe Gly Met His Trp Val Arg Gln Ala Pro Gly Lys
            260                 265                 270

Cys Leu Glu Trp Val Ala Tyr Ile Asn Gly Gly Ser Ser Thr Ile Phe
        275                 280                 285

Tyr Ala Asn Ala Val Lys Gly Arg Phe Thr Ile Ser Arg Asp Asn Ala
290                 295                 300

Lys Asn Thr Leu Tyr Leu Gln Met Asn Ser Leu Arg Ala Glu Asp Thr
305                 310                 315                 320

Ala Val Tyr Tyr Cys Ala Arg Tyr Ala Ser Tyr Gly Gly Gly Ala Met
                325                 330                 335

Asp Tyr Trp Gly Gln Gly Thr Leu Val Thr Val Ser Ser Gly Gly Gly
            340                 345                 350

Gly Ser Gly Gly Gly Gly Ser Gly Gly Gly Gly Ser Gly Gly Gly Gly
        355                 360                 365

Ser Gly Gly Gly Gly Ser Asp Ile Gln Met Thr Gln Ser Pro Ser Ser
370                 375                 380

Leu Ser Ala Ser Val Gly Asp Arg Val Thr Ile Thr Cys Arg Ser Ser
385                 390                 395                 400

Gln Ser Ile Val His Asn Asp Gly Asn Thr Tyr Phe Glu Trp Tyr Gln
                405                 410                 415

Gln Lys Pro Gly Lys Ala Pro Lys Leu Leu Ile Tyr Lys Val Ser Asn
            420                 425                 430

Arg Phe Ser Gly Val Pro Ser Arg Phe Ser Gly Ser Gly Ser Gly Thr
```

His Phe Thr Leu Thr Ile Ser Ser Leu Gln Pro Glu Asp Phe Ala Thr
450                 455                 460

Tyr Tyr Cys Phe Gln Gly Ser Tyr Val Pro Leu Thr Phe Gly Cys Gly
465                 470                 475                 480

Thr Lys Val Glu Ile Lys Ala Ala Ala His His His His His His
                485                 490                 495

His His His

<210> SEQ ID NO 10
<211> LENGTH: 1500
<212> TYPE: DNA
<213> ORGANISM: Artificial Sequence
<220> FEATURE:
<223> OTHER INFORMATION: Synthetic Construct

<400> SEQUENCE: 10

```
gacattcaga tgacccaatc tccgagctct tgtctgcgt ctgtaggga tagggtcact      60
atcacctgca gatctagtca gagcattgta cataatgatg aaacaccta ttttgaatgg    120
taccaacaga aaccaggaaa ggcacccaag cttctcatct ataaagtttc caatcgattt   180
tctggtgtcc catccaggtt agtggcagt gggtctggga cacacttcac cctcaccatc    240
tcttctctgc agccggagga tttcgcaacc tattactgtt ttcaaggttc atatgttcct   300
ctcacgttcg gtcaaggcac caaggtggaa atcaaacgaa ctgtggctgc accatctgtc   360
ttcatcttcc cgccatctga tgagcagttg aaatctggaa ctgcctctgt tgtgtgcctg   420
ctgaataact tctatcccag agaggccaaa gtacagtgga aggtggataa cgccctccaa   480
tcgggtaact cccaggagag tgtcacagag caggacagca aggacagcac ctacagcctc   540
agcagcaccc tgacgctgag caaagcagac tacgagaaac acaaagtcta cgcctgcgaa   600
gtcacccatc agggcctgag ctcgcccgtc acaaagagct caacaggggg agagtgtggt   660
ggaggcggtt caggcggagg tggctctgaa gtgcaactgg tggagtctgg gggaggctta   720
gtgcagcctg gaggaagctt gagactctcc tgtgcagcct ctggattcac tttcagtagc   780
tttggaatgc actgggttcg ccaggctcca gggaagtgtc tcgagtgggt cgcatacatt   840
aatggtggca gtagtaccat cttctatgca aacgcagtga agggccgatt caccatctcc   900
agagataatg ccaagaacac cctgtacctg caaatgaatt ctctgagggc tgaggacacg   960
gccgtgtatt actgtgcaag atatgctagt tacggagggg gtgctatgga ctattgggc   1020
caaggcaccc tggtcacagt ctcctcaggt ggaggcggtt caggcggagg tggctctggc  1080
ggtggcggat ccggaggcgg aggttccgga ggtggcggaa gtgacattca gatgacccaa  1140
tctccgagct ctttgtctgc gtctgtaggg atagggtca ctatcacctg cagatctagt   1200
cagagcattg tacataatga tggaaacacc tattttgaat ggtaccaaca gaaaccagga   1260
aaggcaccca gcttctcat ctataaagtt tccaatcgat tttctggtgt cccatccagg   1320
tttagtggca gtgggtctgg gacacacttc accctcacca tctcttctct gcagccggag  1380
gatttcgcaa cctattactg tttttcaaggt tcatatgttc ctctcacgtt cggttgtggc  1440
accaaggtgg aaatcaaagc ggccgcacat catcatcatc atcaccacca ccactag    1500
```

<210> SEQ ID NO 11
<211> LENGTH: 447
<212> TYPE: PRT
<213> ORGANISM: Artificial Sequence
<220> FEATURE:

<223> OTHER INFORMATION: Synthetic Construct

<400> SEQUENCE: 11

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Phe
             20                  25                  30

Gly Met His Trp Val Arg Gln Ala Pro Gly Lys Gly Leu Glu Trp Val
         35                  40                  45

Ala Tyr Ile Asn Gly Ser Ser Thr Ile Phe Tyr Ala Asn Ala Val
     50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Tyr Ala Ser Tyr Gly Gly Ala Met Asp Tyr Trp Gly Gln
             100                 105                 110

Gly Thr Leu Val Thr Val Ser Ser Ala Ser Thr Lys Gly Pro Ser Val
             115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                 165                 170                 175

Leu Gln Ser Ser Gly Leu Tyr Ser Leu Ser Ser Val Val Thr Val Pro
             180                 185                 190

Ser Ser Ser Leu Gly Thr Lys Thr Tyr Thr Cys Asn Val Asp His Lys
             195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                 245                 250                 255

Pro Glu Val Thr Cys Val Val Asp Val Ser Gln Glu Asp Pro Glu
             260                 265                 270

Val Gln Phe Asn Trp Tyr Val Asp Gly Val Glu Val His Asn Ala Lys
             275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                 325                 330                 335

Ser Lys Ala Lys Gly Gln Pro Arg Glu Pro Gln Val Tyr Thr Leu Pro
             340                 345                 350

Pro Ser Gln Glu Glu Met Thr Lys Asn Gln Val Ser Leu Thr Cys Leu
             355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400
```

Asp Gly Ser Phe Phe Leu Tyr Ser Arg Leu Thr Val Asp Lys Ser Arg
        405                 410                 415

Trp Gln Glu Gly Asn Val Phe Ser Cys Ser Val Met His Glu Ala Leu
    420                 425                 430

His Asn His Tyr Thr Gln Lys Ser Leu Ser Leu Ser Leu Gly Lys
    435                 440                 445

<210> SEQ ID NO 12
<211> LENGTH: 1344
<212> TYPE: DNA
<213> ORGANISM: Artificial Sequence
<220> FEATURE:
<223> OTHER INFORMATION: Synthetic Construct

<400> SEQUENCE: 12

```
gaagtgcaac tggtggagtc tgggggaggc ttagtgcagc ctggaggaag cttgagactc      60
tcctgtgcag cctctggatt cactttcagt agctttggaa tgcactgggt tcgccaggct     120
ccagggaagg gactcgagtg gtcgcatac attaatggtg cagtagtac catcttctat       180
gcaaacgcag tgaagggccg attcaccatc tccagagata tgccaagaa caccctgtac      240
ctgcaaatga attctctgag ggctgaggac acggccgtgt attactgtgc aagatatgct     300
agttacggag gggtgctat ggactattgg ggccaaggca ccctggtcac agtctcctca      360
gcttccacca agggcccatc cgtcttcccc ctggcgccct gctccaggag cacctccgag     420
agcacagccg ccctgggctg cctggtcaag gactacttcc ccgaaccggt gacggtgtcg     480
tggaactcag gcgccctgac cagcggcgtg cacaccttcc cggctgtcct acagtcctca     540
ggactctact ccctcagcag cgtggtgacc gtgccctcca gcagcttggg cacgaagacc     600
tacacctgca acgtagatca caagcccagc aacaccaagg tggacaagag agttgagtcc     660
aaatatggtc ccccatgccc accatgccca gcacctgagt tcctgggggg accatcagtc     720
ttcctgttcc ccccaaaacc caaggacact ctcatgatct cccggacccc tgaggtcacg     780
tgcgtggtgg tggacgtgag ccaggaagac cccgaggtcc agttcaactg gtacgtggat     840
ggcgtggagg tgcataatgc caagacaaag ccgcggagg agcagttcaa cagcacgtac      900
cgtgtggtca gcgtcctcac cgtcctgcac caggactggc tgaacggcaa ggagtacaag     960
tgcaaggtct ccaacaaagg cctcccgtcc tccatcgaga aaaccatctc caaagccaaa    1020
gggcagcccc gagagccaca ggtgtacacc ctgcccccat cccaggagga gatgaccaag    1080
aaccaggtca gcctgacctg cctggtcaaa ggcttctacc ccagcgacat cgccgtggag    1140
tgggagagca atgggcagcc ggagaacaac tacaagacca cgcctcccgt gctggactcc    1200
gacggctcct tcttcctcta cagcaggcta accgtggaca agagcaggtg gcaggagggg    1260
aatgtcttct catgctccgt gatgcatgag gctctgcaca accactacac acagaagagc    1320
ctctccctgt ctctgggtaa atga                                           1344
```

<210> SEQ ID NO 13
<211> LENGTH: 364
<212> TYPE: PRT
<213> ORGANISM: Artificial Sequence
<220> FEATURE:
<223> OTHER INFORMATION: Synthetic Construct

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe

```
            20                  25                  30
Gly Met His Trp Val Arg Gln Ala Pro Gly Lys Cys Leu Glu Trp Val
         35                  40                  45
Ala Tyr Ile Asn Gly Gly Ser Ser Thr Ile Phe Tyr Ala Asn Ala Val
 50                  55                  60
Lys Gly Arg Phe Thr Ile Ser Arg Asp Asn Ala Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Tyr Ala Ser Tyr Gly Gly Ala Met Asp Tyr Trp Gly Gln
             100                 105                 110
Gly Thr Leu Val Thr Val Ser Gly Gly Gly Gly Ser Gly Gly Gly
             115                 120                 125
Gly Ser Gly Gly Gly Ser Gly Gly Gly Ser Gly Gly Gly Gly
             130                 135                 140
Ser Asp Ile Gln Met Thr Gln Ser Pro Ser Ser Leu Ser Ala Ser Val
145                 150                 155                 160
Gly Asp Arg Val Thr Ile Thr Cys Arg Ser Ser Gln Ser Ile Val His
                 165                 170                 175
Asn Asp Gly Asn Thr Tyr Phe Glu Trp Tyr Gln Lys Pro Gly Lys
             180                 185                 190
Ala Pro Lys Leu Leu Ile Tyr Lys Val Ser Asn Arg Phe Ser Gly Val
             195                 200                 205
Pro Ser Arg Phe Ser Gly Ser Gly Ser Gly Thr His Phe Thr Leu Thr
         210                 215                 220
Ile Ser Ser Leu Gln Pro Glu Asp Phe Ala Thr Tyr Tyr Cys Phe Gln
225                 230                 235                 240
Gly Ser Tyr Val Pro Leu Thr Phe Gly Cys Gly Thr Lys Val Glu Ile
             245                 250                 255
Lys Arg Thr Val Ala Ala Pro Ser Val Phe Ile Phe Pro Pro Ser Asp
             260                 265                 270
Glu Gln Leu Lys Ser Gly Thr Ala Ser Val Val Cys Leu Leu Asn Asn
         275                 280                 285
Phe Tyr Pro Arg Glu Ala Lys Val Gln Trp Lys Val Asp Asn Ala Leu
         290                 295                 300
Gln Ser Gly Asn Ser Gln Glu Ser Val Thr Glu Gln Asp Ser Lys Asp
305                 310                 315                 320
Ser Thr Tyr Ser Leu Ser Ser Thr Leu Thr Leu Ser Lys Ala Asp Tyr
             325                 330                 335
Glu Lys His Lys Val Tyr Ala Cys Glu Val Thr His Gln Gly Leu Ser
             340                 345                 350
Ser Pro Val Thr Lys Ser Phe Asn Arg Gly Glu Cys
             355                 360
```

<210> SEQ ID NO 14
<211> LENGTH: 1095
<212> TYPE: DNA
<213> ORGANISM: Artificial Sequence
<220> FEATURE:
<223> OTHER INFORMATION: Synthetic Construct

<400> SEQUENCE: 14
gaagtgcaac tggtggagtc tgggggaggc ttagtgcagc ctggaggaag cttgagactc      60
tcctgtgcag cctctggatt cactttcagt agctttggaa tgcactgggt tcgccaggct     120

```
ccagggaagt gtctcgagtg ggtcgcatac attaatggtg gcagtagtac catcttctat    180
gcaaacgcag tgaagggccg attcaccatc tccagagata atgccaagaa cacccctgtac   240 ctgcaaatga attctctgag ggctgaggac acggccgtgt attactgtgc aagatatgct    300
agttacggag ggggtgctat ggactattgg ggccaaggca ccctggtcac agtctcctca    360
ggtggaggcg gttcaggcgg aggtggctct ggcggtggcg gatccggagg cggaggttcc    420
ggaggtggcg gaagtgacat tcagatgacc caatctccga gctctttgtc tgcgtctgta    480
ggggataggg tcactatcac ctgcagatct agtcagagca ttgtacataa tgatggaaac    540 acctatttg  aatggtacca acagaaacca ggaaaggcac ccaagcttct catctataaa    600
gtttccaatc gattttctgg tgtcccatcc aggtttagtg gcagtgggtc tgggacacac    660 ttcacccctca ccatctcttc tctgcagccg aggatttcg caacctatta ctgttttcaa   720
ggttcatatg ttcctctcac gttcggttgt ggcaccaagg tggaaatcaa acgaactgtg    780
gctgcaccat ctgtcttcat cttcccgcca tctgatgagc agttgaaatc tggaactgcc    840
tctgttgtgt gcctgctgaa taacttctat cccagagagg ccaaagtaca gtggaaggtg    900
gataacgccc tccaatcggg taactcccag gagagtgtca cagagcagga cagcaaggac    960
agcacctaca gcctcagcag caccctgacg ctgagcaaag cagactacga gaaacacaaa   1020
gtctacgcct gcgaagtcac ccatcagggc ctgagctcgc ccgtcacaaa gagcttcaac    1080
aggggagagt gttag                                                    1095
```

<210> SEQ ID NO 15
<211> LENGTH: 584
<212> TYPE: PRT
<213> ORGANISM: Artificial Sequence
<220> FEATURE:
<223> OTHER INFORMATION: Synthetic Construct

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Cys Leu Glu Trp Val
        35                  40                  45

Ala Tyr Ile Asn Gly Gly Ser Thr Ile Phe Tyr Ala Asn Ala Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Ala Ser Tyr Gly Gly Gly Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Ser Gly Gly Gly Ser Gly Gly Gly
    130                 135                 140

Ser Asp Ile Gln Met Thr Gln Ser Pro Ser Ser Leu Ser Ala Ser Val
145                 150                 155                 160

Gly Asp Arg Val Thr Ile Thr Cys Arg Ser Ser Gln Ser Ile Val His
                165                 170                 175

Asn Asp Gly Asn Thr Tyr Phe Glu Trp Tyr Gln Gln Lys Pro Gly Lys
            180                 185                 190

-continued

```
Ala Pro Lys Leu Leu Ile Tyr Lys Val Ser Asn Arg Phe Ser Gly Val
            195                 200                 205

Pro Ser Arg Phe Ser Gly Ser Gly Ser Gly Thr His Phe Thr Leu Thr
    210                 215                 220

Ile Ser Ser Leu Gln Pro Glu Asp Phe Ala Thr Tyr Tyr Cys Phe Gln
225                 230                 235                 240

Gly Ser Tyr Val Pro Leu Thr Phe Gly Cys Gly Thr Lys Val Glu Ile
                245                 250                 255

Lys Ala Ser Thr Lys Gly Pro Ser Val Phe Pro Leu Ala Pro Cys Ser
                260                 265                 270

Arg Ser Thr Ser Glu Ser Thr Ala Ala Leu Gly Cys Leu Val Lys Asp
            275                 280                 285

Tyr Phe Pro Glu Pro Val Thr Val Ser Trp Asn Ser Gly Ala Leu Thr
        290                 295                 300

Ser Gly Val His Thr Phe Pro Ala Val Leu Gln Ser Ser Gly Leu Tyr
305                 310                 315                 320

Ser Leu Ser Ser Val Val Thr Val Pro Ser Ser Ser Leu Gly Thr Lys
                325                 330                 335

Thr Tyr Thr Cys Asn Val Asp His Lys Pro Ser Asn Thr Lys Val Asp
            340                 345                 350

Lys Arg Val Glu Ser Lys Tyr Gly Pro Pro Cys Pro Pro Cys Pro Ala
        355                 360                 365

Pro Glu Phe Leu Gly Gly Pro Ser Val Phe Leu Phe Pro Pro Lys Pro
    370                 375                 380

Lys Asp Thr Leu Met Ile Ser Arg Thr Pro Glu Val Thr Cys Val Val
385                 390                 395                 400

Val Asp Val Ser Gln Glu Asp Pro Glu Val Gln Phe Asn Trp Tyr Val
                405                 410                 415

Asp Gly Val Glu Val His Asn Ala Lys Thr Lys Pro Arg Glu Glu Gln
                420                 425                 430

Phe Asn Ser Thr Tyr Arg Val Val Ser Val Leu Thr Val Leu His Gln
        435                 440                 445

Asp Trp Leu Asn Gly Lys Glu Tyr Lys Cys Lys Val Ser Asn Lys Gly
    450                 455                 460

Leu Pro Ser Ser Ile Glu Lys Thr Ile Ser Lys Ala Lys Gly Gln Pro
465                 470                 475                 480

Arg Glu Pro Gln Val Tyr Thr Leu Pro Pro Ser Gln Glu Glu Met Thr
                485                 490                 495

Lys Asn Gln Val Ser Leu Thr Cys Leu Val Lys Gly Phe Tyr Pro Ser
            500                 505                 510

Asp Ile Ala Val Glu Trp Glu Ser Asn Gly Gln Pro Glu Asn Asn Tyr
        515                 520                 525

Lys Thr Thr Pro Pro Val Leu Asp Ser Asp Gly Ser Phe Phe Leu Tyr
    530                 535                 540

Ser Arg Leu Thr Val Asp Lys Ser Arg Trp Gln Glu Gly Asn Val Phe
545                 550                 555                 560

Ser Cys Ser Val Met His Glu Ala Leu His Asn His Tyr Thr Gln Lys
                565                 570                 575

Ser Leu Ser Leu Ser Leu Gly Lys
            580

<210> SEQ ID NO 16
<211> LENGTH: 1755
```

<212> TYPE: DNA
<213> ORGANISM: Artificial Sequence
<220> FEATURE:
<223> OTHER INFORMATION: Synthetic Construct

<400> SEQUENCE: 16

```
gaagtgcaac tggtggagtc tgggggaggc ttagtgcagc ctggaggaag cttgagactc      60
tcctgtgcag cctctggatt cactttcagt agctttggaa tgcactgggt tcgccaggct     120
ccagggaagt gtctcgagtg gtcgcatac attaatggtg gcagtagtac catcttctat     180
gcaaacgcag tgaagggccg attcaccatc tccagagata atgccaagaa caccctgtac     240
ctgcaaatga attctctgag ggctgaggac acggccgtgt attactgtgc aagatatgct     300
agttacggag ggggtgctat ggactattgg ggccaaggca ccctggtcac agtctcctca     360
ggtggaggcg gttcaggcgg aggtggctct ggcggtggcg gatccggagg cggaggttcc     420
ggaggtggcg gaagtgacat tcagatgacc caatctccga gctctttgtc tgcgtctgta     480
ggggatagggg tcactatcac ctgcagatct agtcagagca ttgtacataa tgatggaaac     540
acctattttg aatggtacca acagaaacca ggaaaggcac ccaagcttct catctataaa     600
gtttccaatc gattttctgg tgtcccatcc aggtttagtg gcagtgggtc tgggacacac     660
ttcacccctca ccatctcttc tctgcagccg gaggatttcg caacctatta ctgttttcaa     720
ggttcatatg ttcctctcac gttcggttgt ggcaccaagg tggaaatcaa agcttccacc     780
aagggcccat ccgtcttccc cctggcgccc tgctccagga gcacctccga gagcacagcc     840
gccctgggct gcctggtcaa ggactacttc cccgaaccgg tgacggtgtc gtggaactca     900
ggcgccctga ccagcggcgt gcacaccttc ccggctgtcc tacagtcctc aggactctac     960
tccctcagca gcgtggtgac cgtgccctcc agcagcttgg gcacgaagac ctacacctgc    1020
aacgtagatc acaagcccag caacaccaag gtggacaaga gagttgagtc caaatatggt    1080
ccccccatgcc caccatgccc agcacctgag ttcctggggg gaccatcagt cttcctgttc    1140
cccccaaaac ccaaggacac tctcatgatc tcccggaccc ctgaggtcac gtgcgtggtg    1200
gtggacgtga gccaggaaga ccccgaggtc cagttcaact ggtacgtgga tggcgtggag    1260
gtgcataatg ccaagacaaa gccgcgggag gagcagttca acagcacgta ccgtgtggtc    1320
agcgtcctca ccgtcctgca ccaggactgg ctgaacggca aggagtacaa gtgcaaggtc    1380
tccaacaaag gcctcccgtc ctccatcgag aaaaccatct ccaaagccaa agggcagccc    1440
cgagagccac aggtgtacac cctgcccccca tcccaggagg agatgaccaa gaaccaggtc    1500
agcctgacct gcctggtcaa aggcttctac cccagcgaca tcgccgtgga gtgggagagc    1560
aatgggcagc cggagaacaa ctacaagacc acgcctcccg tgctggactc cgacggctcc    1620
ttcttcctct acagcaggct aaccgtggac aagagcaggt ggcaggaggg gaatgtcttc    1680
tcatgctccg tgatgcatga ggctctgcac aaccactaca cacagaagag cctctccctg    1740
tctctgggta aatga                                                     1755
```

<210> SEQ ID NO 17
<211> LENGTH: 5
<212> TYPE: PRT
<213> ORGANISM: Artificial Sequence
<220> FEATURE:
<223> OTHER INFORMATION: Synthetic Construct

<400> SEQUENCE: 17

Ser Phe Gly Met His
1               5

<210> SEQ ID NO 18
<211> LENGTH: 17
<212> TYPE: PRT
<213> ORGANISM: Artificial Sequence
<220> FEATURE:
<223> OTHER INFORMATION: Synthetic Construct

<400> SEQUENCE: 18

Tyr Ile Asn Gly Gly Ser Ser Thr Ile Phe Tyr Ala Asn Ala Val Lys
1               5                   10                  15

Gly

<210> SEQ ID NO 19
<211> LENGTH: 11
<212> TYPE: PRT
<213> ORGANISM: Artificial Sequence
<220> FEATURE:
<223> OTHER INFORMATION: Synthetic Construct

<400> SEQUENCE: 19

Tyr Ala Ser Tyr Gly Gly Gly Ala Met Asp Tyr
1               5                   10

<210> SEQ ID NO 20
<211> LENGTH: 16
<212> TYPE: PRT
<213> ORGANISM: Artificial Sequence
<220> FEATURE:
<223> OTHER INFORMATION: Synthetic Construct

<400> SEQUENCE: 20

Arg Ser Ser Gln Ser Ile Val His Asn Asp Gly Asn Thr Tyr Phe Glu
1               5                   10                  15

<210> SEQ ID NO 21
<211> LENGTH: 7
<212> TYPE: PRT
<213> ORGANISM: Artificial Sequence
<220> FEATURE:
<223> OTHER INFORMATION: Synthetic Construct

<400> SEQUENCE: 21

Lys Val Ser Asn Arg Phe Ser
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic Construct

<400> SEQUENCE: 22

Phe Gln Gly Ser Tyr Val Pro Leu Thr
1               5

<210> SEQ ID NO 23
<211> LENGTH: 120
<212> TYPE: PRT
<213> ORGANISM: Artificial Sequence
<220> FEATURE:
<223> OTHER INFORMATION: Synthetic Construct

<400> SEQUENCE: 23

Glu Val Gln Leu Val Glu Ser Gly Gly Gly Leu Val Gln Pro Gly Gly

```
             1               5                  10                 15
         Ser Leu Arg Leu Ser Cys Ala Ala Ser Gly Phe Thr Phe Ser Phe
                        20                  25                  30

Gly Met His Trp Val Arg Gln Ala Pro Gly Lys Gly Leu Glu Trp Val
                        35                  40                  45

Ala Tyr Ile Asn Gly Ser Ser Thr Ile Phe Tyr Ala Asn Ala Val
                    50                  55                  60

Lys Gly Arg Phe Thr Ile Ser Arg Asp Asn Ala Lys Asn Thr Leu Tyr
          65                  70                  75                  80

Leu Gln Met Asn Ser Leu Arg Ala Glu Asp Thr Ala Val Tyr Tyr Cys
                            85                  90                  95

Ala Arg Tyr Ala Ser Tyr Gly Gly Ala Met Asp Tyr Trp Gly Gln
                        100                 105                 110

Gly Thr Leu Val Thr Val Ser Ser
                        115                 120

<210> SEQ ID NO 24
<211> LENGTH: 112
<212> TYPE: PRT
<213> ORGANISM: Artificial Sequence
<220> FEATURE:
<223> OTHER INFORMATION: Synthetic Construct

<400> SEQUENCE: 24

Asp Ile Gln Met Thr Gln Ser Pro Ser Ser Leu Ser Ala Ser Val Gly
 1               5                  10                  15

Asp Arg Val Thr Ile Thr Cys Arg Ser Ser Gln Ser Ile Val His Asn
                20                  25                  30

Asp Gly Asn Thr Tyr Phe Glu Trp Tyr Gln Gln Lys Pro Gly Lys Ala
                35                  40                  45

Pro Lys Leu Leu Ile Tyr Lys Val Ser Asn Arg Phe Ser Gly Val Pro
         50                  55                  60

Ser Arg Phe Ser Gly Ser Gly Ser Gly Thr His Phe Thr Leu Thr Ile
 65                  70                  75                  80

Ser Ser Leu Gln Pro Glu Asp Phe Ala Thr Tyr Tyr Cys Phe Gln Gly
                    85                  90                  95

Ser Tyr Val Pro Leu Thr Phe Gly Gln Gly Thr Lys Val Glu Ile Lys
                100                 105                 110

<210> SEQ ID NO 25
<211> LENGTH: 5
<212> TYPE: PRT
<213> ORGANISM: Artificial Sequence
<220> FEATURE:
<223> OTHER INFORMATION: Synthetic Construct

<400> SEQUENCE: 25

Gly Gly Gly Gly Ser
 1               5

<210> SEQ ID NO 26
<211> LENGTH: 8
<212> TYPE: PRT
<213> ORGANISM: Artificial Sequence
<220> FEATURE:
<223> OTHER INFORMATION: Synthetic Construct

<400> SEQUENCE: 26

Gly Gly Gly Gly Ser Ala Ala Ala
 1               5
```

```
<210> SEQ ID NO 27
<211> LENGTH: 5
<212> TYPE: PRT
<213> ORGANISM: Artificial Sequence
<220> FEATURE:
<223> OTHER INFORMATION: Synthetic Construct

<400> SEQUENCE: 27

Ala Ser Thr Gly Ser
1               5

<210> SEQ ID NO 28
<211> LENGTH: 10
<212> TYPE: PRT
<213> ORGANISM: Artificial Sequence
<220> FEATURE:
<223> OTHER INFORMATION: Synthetic Construct

<400> SEQUENCE: 28

Ala Ser Thr Gly Ser Gly Gly Gly Gly Ser
1               5                   10

<210> SEQ ID NO 29
<211> LENGTH: 120
<212> TYPE: PRT
<213> ORGANISM: Artificial Sequence
<220> FEATURE:
<223> OTHER INFORMATION: Synthetic Construct

<400> SEQUENCE: 29

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Cys Leu Glu Trp Val
        35                  40                  45

Ala Tyr Ile Asn Gly Gly Ser Ser Thr Ile Phe Tyr Ala Asn Ala Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Ala Ser Tyr Gly Gly Ala Met Asp Tyr Trp Gly Gln
            100                 105                 110

Gly Thr Leu Val Thr Val Ser Ser
        115                 120

<210> SEQ ID NO 30
<211> LENGTH: 112
<212> TYPE: PRT
<213> ORGANISM: Artificial Sequence
<220> FEATURE:
<223> OTHER INFORMATION: Synthetic Construct

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Val His Asn
            20                  25                  30

Asp Gly Asn Thr Tyr Phe Glu Trp Tyr Gln Gln Lys Pro Gly Lys Ala
        35                  40                  45
```

```
Pro Lys Leu Leu Ile Tyr Lys Val Ser Asn Arg Phe Ser Gly Val Pro
    50                  55                  60

Ser Arg Phe Ser Gly Ser Gly Ser Gly Thr His Phe Thr Leu Thr Ile
65                  70                  75                  80

Ser Ser Leu Gln Pro Glu Asp Phe Ala Thr Tyr Tyr Cys Phe Gln Gly
                85                  90                  95

Ser Tyr Val Pro Leu Thr Phe Gly Cys Gly Thr Lys Val Glu Ile Lys
                100                 105                 110

<210> SEQ ID NO 31
<211> LENGTH: 412
<212> TYPE: PRT
<213> ORGANISM: Homo Sapiens

<400> SEQUENCE: 31

Met Pro Leu Gln Leu Leu Leu Leu Ile Leu Leu Gly Pro Gly Asn
1               5                   10                  15

Ser Leu Gln Leu Trp Asp Thr Trp Ala Asp Glu Ala Glu Lys Ala Leu
                20                  25                  30

Gly Pro Leu Leu Ala Arg Asp Arg Arg Gln Ala Thr Glu Tyr Glu Tyr
                35                  40                  45

Leu Asp Tyr Asp Phe Leu Pro Glu Thr Glu Pro Pro Glu Met Leu Arg
    50                  55                  60

Asn Ser Thr Asp Thr Thr Pro Leu Thr Gly Pro Gly Thr Pro Glu Ser
65                  70                  75                  80

Thr Thr Val Glu Pro Ala Ala Arg Arg Ser Thr Gly Leu Asp Ala Gly
                85                  90                  95

Gly Ala Val Thr Glu Leu Thr Thr Glu Leu Ala Asn Met Gly Asn Leu
                100                 105                 110

Ser Thr Asp Ser Ala Ala Met Glu Ile Gln Thr Thr Gln Pro Ala Ala
            115                 120                 125

Thr Glu Ala Gln Thr Thr Gln Pro Val Pro Thr Glu Ala Gln Thr Thr
        130                 135                 140

Pro Leu Ala Ala Thr Glu Ala Gln Thr Thr Arg Leu Thr Ala Thr Glu
145                 150                 155                 160

Ala Gln Thr Thr Pro Leu Ala Ala Thr Glu Ala Gln Thr Thr Pro Pro
                165                 170                 175

Ala Ala Thr Glu Ala Gln Thr Thr Gln Pro Thr Gly Leu Glu Ala Gln
                180                 185                 190

Thr Thr Ala Pro Ala Ala Met Glu Ala Gln Thr Ala Pro Ala Ala
            195                 200                 205

Met Glu Ala Gln Thr Thr Pro Pro Ala Ala Met Glu Ala Gln Thr Thr
        210                 215                 220

Gln Thr Thr Ala Met Glu Ala Gln Thr Thr Ala Pro Glu Ala Thr Glu
225                 230                 235                 240

Ala Gln Thr Thr Gln Pro Thr Ala Thr Glu Ala Gln Thr Thr Pro Leu
                245                 250                 255

Ala Ala Met Glu Ala Leu Ser Thr Glu Pro Ser Ala Thr Glu Ala Leu
                260                 265                 270

Ser Met Glu Pro Thr Thr Lys Arg Gly Leu Phe Ile Pro Phe Ser Val
            275                 280                 285

Ser Ser Val Thr His Lys Gly Ile Pro Met Ala Ala Ser Asn Leu Ser
        290                 295                 300

Val Asn Tyr Pro Val Gly Ala Pro Asp His Ile Ser Val Lys Gln Cys
```

```
                305                 310                 315                 320

Leu Leu Ala Ile Leu Ile Leu Ala Leu Val Ala Thr Ile Phe Phe Val
                325                 330                 335

Cys Thr Val Val Leu Ala Val Arg Leu Ser Arg Lys Gly His Met Tyr
                340                 345                 350

Pro Val Arg Asn Tyr Ser Pro Thr Glu Met Val Cys Ile Ser Ser Leu
                355                 360                 365

Leu Pro Asp Gly Gly Glu Gly Pro Ser Ala Thr Ala Asn Gly Gly Leu
            370                 375                 380

Ser Lys Ala Lys Ser Pro Gly Leu Thr Pro Glu Pro Arg Glu Asp Arg
385                 390                 395                 400

Glu Gly Asp Asp Leu Thr Leu His Ser Phe Leu Pro
                405                 410

<210> SEQ ID NO 32
<211> LENGTH: 402
<212> TYPE: PRT
<213> ORGANISM: Homo Sapiens

<400> SEQUENCE: 32

Met Pro Leu Gln Leu Leu Leu Leu Ile Leu Leu Gly Pro Gly Asn
1               5                   10                  15

Ser Leu Gln Leu Trp Asp Thr Trp Ala Asp Glu Ala Glu Lys Ala Leu
                20                  25                  30

Gly Pro Leu Leu Ala Arg Asp Arg Arg Gln Ala Thr Glu Tyr Glu Tyr
            35                  40                  45

Leu Asp Tyr Asp Phe Leu Pro Glu Thr Glu Pro Pro Glu Met Leu Arg
    50                  55                  60

Asn Ser Thr Asp Thr Thr Pro Leu Thr Gly Pro Gly Thr Pro Glu Ser
65                  70                  75                  80

Thr Thr Val Glu Pro Ala Ala Arg Arg Ser Thr Gly Leu Asp Ala Gly
                85                  90                  95

Gly Ala Val Thr Glu Leu Thr Thr Glu Leu Ala Asn Met Gly Asn Leu
            100                 105                 110

Ser Thr Asp Ser Ala Ala Met Glu Ile Gln Thr Thr Gln Pro Ala Ala
            115                 120                 125

Thr Glu Ala Gln Thr Thr Pro Leu Ala Ala Thr Glu Ala Gln Thr Thr
        130                 135                 140

Arg Leu Thr Ala Thr Glu Ala Gln Thr Thr Pro Leu Ala Ala Thr Glu
145                 150                 155                 160

Ala Gln Thr Thr Pro Pro Ala Ala Thr Glu Ala Gln Thr Thr Gln Pro
                165                 170                 175

Thr Gly Leu Glu Ala Gln Thr Thr Ala Pro Ala Ala Met Glu Ala Gln
            180                 185                 190

Thr Thr Ala Pro Ala Ala Met Glu Ala Gln Thr Thr Pro Pro Ala Ala
        195                 200                 205

Met Glu Ala Gln Thr Thr Gln Thr Thr Ala Met Glu Ala Gln Thr Thr
    210                 215                 220

Ala Pro Glu Ala Thr Glu Ala Gln Thr Gln Pro Thr Ala Thr Glu
225                 230                 235                 240

Ala Gln Thr Thr Pro Leu Ala Ala Met Glu Ala Leu Ser Thr Glu Pro
                245                 250                 255

Ser Ala Thr Glu Ala Leu Ser Met Glu Pro Thr Thr Lys Arg Gly Leu
            260                 265                 270
```

```
Phe Ile Pro Phe Ser Val Ser Val Thr His Lys Gly Ile Pro Met
            275                 280                 285

Ala Ala Ser Asn Leu Ser Val Asn Tyr Pro Val Gly Ala Pro Asp His
        290                 295                 300

Ile Ser Val Lys Gln Cys Leu Leu Ala Ile Leu Ile Leu Ala Leu Val
305                 310                 315                 320

Ala Thr Ile Phe Phe Val Cys Thr Val Val Leu Ala Val Arg Leu Ser
                325                 330                 335

Arg Lys Gly His Met Tyr Pro Val Arg Asn Tyr Ser Pro Thr Glu Met
                340                 345                 350

Val Cys Ile Ser Ser Leu Leu Pro Asp Gly Glu Gly Pro Ser Ala
            355                 360                 365

Thr Ala Asn Gly Gly Leu Ser Lys Ala Lys Ser Pro Gly Leu Thr Pro
        370                 375                 380

Glu Pro Arg Glu Asp Arg Glu Gly Asp Asp Leu Thr Leu His Ser Phe
385                 390                 395                 400

Leu Pro
```

<210> SEQ ID NO 33
<211> LENGTH: 25
<212> TYPE: PRT
<213> ORGANISM: Artificial Sequence
<220> FEATURE:
<223> OTHER INFORMATION: Synthetic Construct

<400> SEQUENCE: 33

```
Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25
```

<210> SEQ ID NO 34
<211> LENGTH: 10
<212> TYPE: PRT
<213> ORGANISM: Artificial Sequence
<220> FEATURE:
<223> OTHER INFORMATION: Synthetic Construct

<400> SEQUENCE: 34

```
Gly Gly Gly Gly Ser Gly Gly Gly Gly Ser
1               5                   10
```

<210> SEQ ID NO 35
<211> LENGTH: 11
<212> TYPE: PRT
<213> ORGANISM: Artificial Sequence
<220> FEATURE:
<223> OTHER INFORMATION: Synthetic Construct

<400> SEQUENCE: 35

```
Gly Gly Gly Gly Ser Gly Gly Gly Gly Ser Gly
1               5                   10
```

<210> SEQ ID NO 36
<211> LENGTH: 12
<212> TYPE: PRT
<213> ORGANISM: Artificial Sequence
<220> FEATURE:
<223> OTHER INFORMATION: Synthetic Construct

```
<400> SEQUENCE: 36

Gly Gly Gly Gly Ser Gly Gly Gly Gly Ser Gly Gly
1               5                   10
```